(12) United States Patent
Kodama et al.

(10) Patent No.: US 7,776,512 B2
(45) Date of Patent: Aug. 17, 2010

(54) POSITIVE PHOTOSENSITIVE COMPOSITION

(75) Inventors: Kunihiko Kodama, Shizuoka (JP); Toshiaki Aoai, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/362,097

(22) Filed: Jan. 29, 2009

(65) Prior Publication Data

US 2009/0148791 A1    Jun. 11, 2009

Related U.S. Application Data

(60) Continuation of application No. 11/512,173, filed on Aug. 30, 2006, which is a division of application No. 10/866,054, filed on Jun. 14, 2004, now Pat. No. 7,435,526, which is a division of application No. 09/978,103, filed on Oct. 17, 2001, now Pat. No. 6,749,987.

(30) Foreign Application Priority Data

Oct. 20, 2000  (JP)  ............................. 2000-321128
Nov. 20, 2000  (JP)  ............................. 2000-352899
Apr. 27, 2001  (JP)  ............................. 2001-132546

(51) Int. Cl.
*G03F 7/039*    (2006.01)

(52) U.S. Cl. .................... 430/270.1; 430/326; 430/921; 430/914; 430/925; 522/31; 522/57; 522/59

(58) Field of Classification Search .................. None
See application file for complete search history.

(56) References Cited

U.S. PATENT DOCUMENTS

| | | | |
|---|---|---|---|
| 5,498,820 A | | 3/1996 | Hommeltoft |
| 5,635,332 A | * | 6/1997 | Nakano et al. ........... 430/270.1 |
| 5,824,824 A | | 10/1998 | Osawa et al. |
| 5,968,713 A | * | 10/1999 | Nozaki et al. .............. 430/326 |
| 6,306,555 B1 | | 10/2001 | Schulz et al. |
| 6,692,897 B2 | | 2/2004 | Fujimori et al. |
| 6,749,987 B2 | | 6/2004 | Kodama et al. |
| 6,783,927 B2 | | 8/2004 | Yoshioka |
| 6,849,374 B2 | | 2/2005 | Cameron et al. |
| 6,855,476 B2 | | 2/2005 | Ferreira et al. |
| 6,908,722 B2 | | 6/2005 | Ebata et al. |
| 2001/0044072 A1 | | 11/2001 | Trefonas |
| 2002/0197558 A1 | | 12/2002 | Ferreira et al. |

FOREIGN PATENT DOCUMENTS

| | | |
|---|---|---|
| DE | 295 421 A5 | 10/1991 |
| EP | 0 693 468 A2 | 1/1996 |
| EP | 0985974 A1 * | 3/2000 |
| EP | 1 033 624 A1 | 9/2000 |
| EP | 1 041 442 A1 | 10/2000 |
| JP | 55106453 A | 8/1980 |
| JP | 9-12537 A | 1/1997 |
| JP | 10-007650 A | 1/1998 |
| JP | 10010715 A | 1/1998 |
| JP | 2000-275845 A | 10/2000 |
| JP | 2001-133967 A | 5/2001 |
| WO | 00/08525 A | 2/2000 |

OTHER PUBLICATIONS

CA 94:130305 for JP 55106453, Aug. 1980.
CA 69:95876 1968.
CA 68:12389 1967.
CA 55:13179 1960.
XP-002188319—Abstract of JP 08/027094 Jan. 30, 1996.
European Search Report dated Feb. 11, 2002.
CA 116:245286 abstract of DD 295421, Oct. 31, 1991.
CA 128:161008 abstract of JP 10010715, Jan. 16, 1998.
Houlihan et al., Chem. Mater. year 2000, web published date Oct. 28, 2000, vol. 12, pp. 3516-3524, American Chemical Society.
English translation of JP, 2001-133967, A (2001) from machine translation from AIPN Japan Patent Office National center for Industrial Property Information and Training, generated Jul. 9, 2008, 10 pages.
King et al. J. ORg. Chem 1996, No Month Given, vol. 61, pp. 7250-7255, American Chemical Society.
Lee et al, Journal of Photopolymer Science and Technology, vol. 13, No. 2 (2000) pp. 215-216. No month given.
AN 2000:579488 CAPLUS File, Copyright 2008 ACS on STN 2 pages Entered: Aug. 23, 2000 abstract of Lee article from Journal of Photopolymer Science and Technology (2000), 13(2), 215-216.
English translation of JP 10-007650, A (1998) from machine translation from AIPN Japan Patent Office National center for Industrial Property Information and training, generated May 14, 2008, 24 pages.
Research Disclosure No. 337007 published May 1992, 2 pages, Kenneth Mason Publications Ltd.
A Japanese Office Action dated Apr. 9, 2008.
A Japanese Office Action dated Apr. 16, 2008.

* cited by examiner

*Primary Examiner*—Cynthia Hamilton
(74) *Attorney, Agent, or Firm*—Sughrue Mion, PLLC

(57) ABSTRACT

A positive photosensitive composition comprises a compound capable of generating a specified sulfonic acid upon irradiation with one of an actinic ray and radiation and (B) a resin capable of decomposing under the action of an acid to increase the solubility in an alkali developer.

4 Claims, No Drawings

POSITIVE PHOTOSENSITIVE COMPOSITION

This is a continuation of application Ser. No. 11/512,173 filed Aug. 30, 2006, which is a divisional of application Ser. No. 10/866,054 filed Jun. 14, 2004 (now U.S. Pat. No. 7,435,526), which is a divisional of application Ser. No. 09/978,103 filed Oct. 17, 2001 (now U.S. Pat. No. 6,749,987). The entire disclosure of the prior applications, application Ser Nos. 11/512,173, 10/866,054 and 09/978,103, is hereby incorporated by reference.

FIELD OF THE INVENTION

The present invention relates to a positive photosensitive composition used in the manufacturing process of a lithographic printing plate or a semiconductor such as IC, in production of a circuit board for a liquid crystal device or a thermal head, and in the process of the other photofabrications.

BACKGROUND OF THE INVENTION

Various photosensitive compositions have been used in the manufacturing process of a lithographic printing plate, a semiconductor such as IC, in production of circuit boards for a liquid crystal device and a thermal head, and in the process of photofabrication for other devices. As the photosensitive compositions for these uses, photoresist photosensitive compositions are generally utilized, and they are broadly classified into two groups, namely the group of positive photoresist compositions and the group of negative ones.

Representatives of such positive photoresist compositions are chemical amplification resist compositions as disclosed in U.S. Pat. No. 4,491,628 and European Patent No. 249,139.

Chemical amplification positive resist compositions are materials for forming patterns on substrates. More specifically, these compositions generate acids by irradiation with actinic rays, such as far ultraviolet rays, and undergo reaction utilizing these acids as a catalyst. This reaction causes a difference in solubilities in a developer between the areas unirradiated and irradiated with the actinic rays, thereby enabling pattern formation.

Examples of such chemical amplification positive resist compositions include the combination of a compound capable of generating an acid by photolysis (hereinafter abbreviated as a photo-acid generator) and an acetal or O,N-acetal compound (JP-A-48-89003, the term "JP-A" as used herein means an "unexamined published Japanese Patent application), the combination of a photo-acid generator and an orthoester or amidoacetal compound (JP-A-51-120714), the combination of a photo-acid generator and a polymer having acetal or ketal groups on the main chain (JP-A-53-133429), the combination of a photo-acid generator and an enol ether compound (JP-A-55-12995), the combination of a photo-acid generator and an N-acylaminocarbonic acid compound (JP-A-55-126236), the combination of a photo-acid generator and a polymer having orthoester groups on the main chain (JP-A-56-17345), the combination of a photo-acid generator and a tertiary alkyl ester compound (JP-A-60-3625), the combination of a photo-acid generator and a silyl ester compound (JP-A-60-10247), and the combination of a photo-acid generator and a silyl ether compound (JP-A-60-121446). These compositions have high photosensitivity since the their quantum yields are each greater than 1 in principle.

As examples of a system which is stable upon storage at room temperature but decomposed by heating in the presence of an acid to become alkali-soluble, mention may be made of the systems obtained by combining tertiary or secondary carbon-containing (such as t-butyl or 2-cyclohexenyl) ester or carboxylic acid ester compounds and compounds capable of generating acids by exposure as described in JP-A-59-45439, JP-A-60-3625, JP-A-62-229242, JP-A-63-27829, JP-A-63-36240, JP-A-63-250642, Polym. Eng. Sce., vol. 23, p. 1012 (1983), ACS. Sym., vol. 242, p. 11 (1984), Semiconductor World, the November issue in 1987, p. 91, Macromolecules, vol. 21, p. 1475 (1988), and SPIE, vol. 920, p. 42 (1988). These systems also have high photosensitivity, and show poor absorption in the far ultraviolet region. Therefore, they can be effective in enabling the use of a light source with shorter wavelengths suitable for submicron photolithography.

The chemical-amplification positive resist compositions as mentioned above are broadly classified into two groups. One group includes three-component systems which are each constituted of an alkali-soluble resin, a compound capable of generating an acid upon exposure to radiation (photo-acid generator) and a compound having an acid-decomposable group and inhibiting dissolution of an alkali-soluble resin. The other group includes two-component systems which are each constituted of a resin having groups capable of being decomposed by reaction with an acid to become alkali-soluble and a photo-acid generator.

In such two-component or three-component positive resist of chemical amplification type, resist patterns are formed by development after thermal treatment in the presence of an acid generated from a photo-acid generator by exposure.

As mentioned above, such chemical amplification positive resist compositions can be systems suitable for a light source with shorter wavelengths enabling submicron photolithography. However, further improvements in resolution and process latitude, including exposure margin or focus depth, have been required for them.

In such systems, compounds capable of generating trifluoromethanesulfonic acid, such as triphenylsulfonium trifluoromethanesulfonate, and compounds capable of generating longer-chain fluoroalkylsulfonic acids are used as photo-acid generators.

Further, compounds capable of perfluoroalkanesulfonic acids, such as triphenylsulfonium triflate and bis(t-butylphenyl)iodonium perfluorobutanesulfonate, are also well known as photo-acid generators. A compound capable of generating a perfluorobutanesulfonic acid is described in WO 00/08525, JP-A-09-12537, JP-A-2000-275845 and EP 1041442A.

In general, perfluoroalkyl compounds have high hydrophobicity, so they are used for water-repellent coating on clothes. Therefore, the resist using an acid generator capable of generating a perfluoroalkylsulfonic acid upon irradiation with actinic rays has a low affinity for aqueous developers, and so it suffers from a sensitivity drop and scum development due to degradation in developability.

Further, the arts mentioned above cannot satisfactorily meet the current needs for photolithography and have room for improvements in resolution and process latitude, including exposure margin and focus depth.

SUMMARY OF THE INVENTION

Therefore, an object of the invention is to provide a positive photosensitive composition which can ensure high resolution and improved exposure margin in photolithography utilizing a light source for short-wavelength exposure enabling super minute patterning and a chemical-amplification positive resist.

Another object of the invention is to provide a positive resist composition enabling reduction in scum and improvement in process latitude, including exposure margin and focus depth.

The following positive resist compositions are provided as embodiments of the invention, and thereby the aforementioned objects can be attained.

(1) A positive photosensitive composition comprising:

(A) a compound capable of generating a sulfonic acid represented by formula (X) below upon irradiation with one of an actinic ray and radiation; and (B) a resin capable of decomposing under the action of an acid to increase the solubility in an alkali developer:

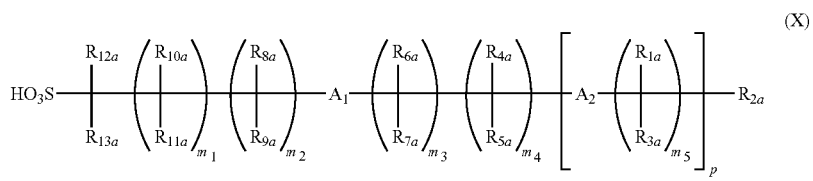

(X)

wherein $R_{1a}$ to $R_{13a}$ groups each represents a hydrogen atom, an alkyl group, a haloalkyl group, a halogen atom or a hydroxyl group; $A_1$ and $A_2$, which are the same or different, each represents a single bond or a hetero atom-containing divalent linkage group, provided that, when each of $A_1$ and $A_2$ is single bond, all of the $R_{1a}$ to $R_{13a}$ groups do not simultaneously represent a fluorine atom and all of the $R_{1a}$ to $R_{13a}$ groups do not simultaneously represent a hydrogen atom; $m_1$ to $m_5$, which are the same or different, each represents an integer of 0 to 12; and p represents an integer of 0 to 4.

(2). The positive photosensitive composition as described in item (1), wherein the sulfonic acid represented by formula (X) comprises a compound represented by formula (X'):

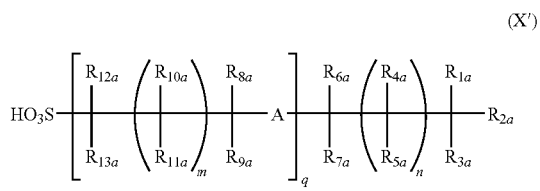

(X')

wherein $R_{1a}$ to $R_{13a}$ groups each represents a hydrogen atom, an alkyl group, a haloalkyl group, a halogen atom or a hydroxyl group; $A_1$ and $A_2$, which are the same or different, each represents a single bond or a hetero atom-containing divalent linkage group, provided that, when each of $A_1$ and $A_2$ is single bond, all of the $R_{1a}$ to $R_{13a}$ groups do not simultaneously represent a fluorine atom and all of the $R_{1a}$ to $R_{13a}$ groups do not simultaneously represent a hydrogen atom; m represents an integer of 0 to 12; n represents an integer of 0 to 12; and q represents an integer of 1 to 3.

(3). The positive photosensitive composition as described in item (1), which further comprises (C) a dissolution-inhibiting compound having a molecular weight of not more than 3,000 which contains an acid-decomposable group and can increase the solubility in an alkali developer by the action of an acid.

(4). The positive photosensitive composition as described in item (1), wherein the resin (B) contains a lactone structure.

(5). The positive photosensitive composition as described in item (1), wherein the compound (A) comprises at least one of an iodonium salt of the sulfonic acid represented by formula (X) and sulfonium salt of the sulfonic acid represented by formula (X).

(6). A positive photosensitive composition as described in item (1), wherein the compound (A) comprises at least one compound selected from compounds represented by formulae (I) to (III):

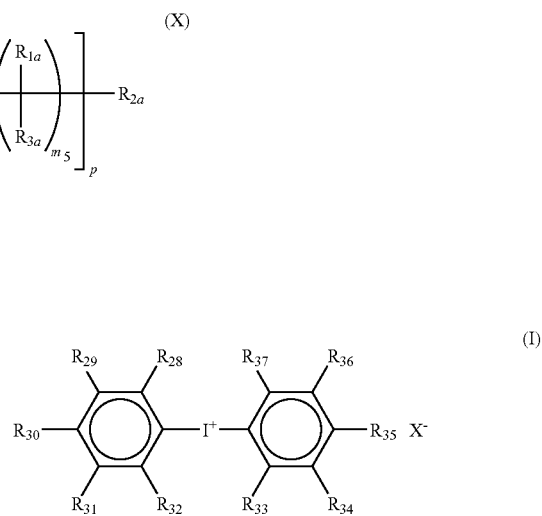

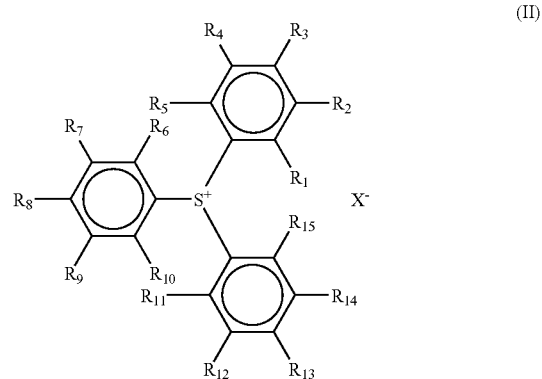

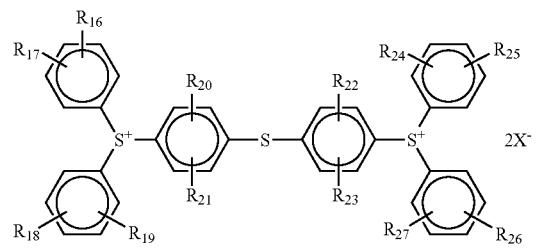

wherein $R_1$ to $R_{37}$ groups, which are the same or different, each represents a hydrogen atom, a straight-chain or branched alkyl group having 1 to 4 carbon atoms, a cycloalkyl group having 3 to 8 carbon atoms, a alkoxy group having 1 to 4 carbon atoms, a hydroxyl group, a halogen atom, or an —S—$R_{38}$ group; $R_{38}$ represents a straight-chain or branched alkyl group having 1 to 12 carbon atoms, a cycloalkyl group having 3 to 8 carbon atoms, or an aryl group having 6 to 14 carbon atoms; $X^-$ represents an anion of the sulfonic acid represented by formula (X) described above.

(7). The positive photosensitive composition as described in item (1), wherein at least one of the $R_{1a}$ to $R_{13a}$ groups in formula (X) represents a fluorine atom.

(8). The positive photosensitive composition as described in item (1), wherein the sulfonic acid represented by formula (X) comprises $CF_3CF_2$—O—$CF_2CF_2SO_3H$.

(9). The positive photosensitive composition as described in item (1), wherein the resin (B) contains at least one of a monocyclic alicyclic structure and polycyclic alicyclic structure.

(10). A positive photosensitive composition comprising:
(A) a compound capable of generating a sulfonic acid represented by formula (X) below upon irradiation with one of an actinic ray and radiation;
(C) a dissolution-inhibiting compound having a molecular weight of not more than 3,000 which contains an acid-decomposable group and can increase the solubility in an alkali developer by the action of an acid; and
(D) a resin insoluble in water and soluble in an alkali developer;

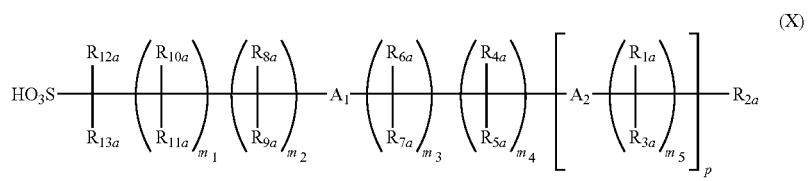

wherein $R_{1a}$ to $R_{13a}$ groups each represents a hydrogen atom, an alkyl group, a haloalkyl group, a halogen atom or a hydroxyl group; $A_1$ and $A_2$, which are the same or different, each represents a single bond or a hetero atom-containing divalent linkage group, provided that, when each of $A_1$ and $A_2$ is single bond, all of the $R_{1a}$ to $R_{13a}$ groups do not simultaneously represent a fluorine atom and all of the $R_{1a}$ to $R_{13a}$ groups do not simultaneously represent a hydrogen atom; $m_1$ to $m_5$, which are the same or different, each represents an integer of 0 to 12; and p represents an integer of 0 to 4.

(11). The positive photosensitive composition as described in item (10), wherein the sulfonic acid represented by formula (X) comprises a compound represented by formula (X'):

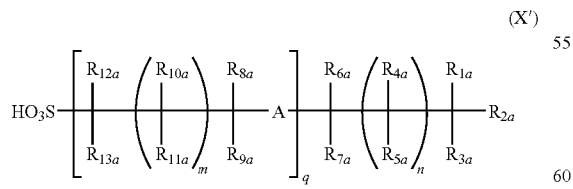

wherein $R_{1a}$ to $R_{13a}$ groups each represents a hydrogen atom, an alkyl group, a haloalkyl group, a halogen atom or a hydroxyl group; $A_1$ and $A_2$, which are the same or different, each represents a single bond or a heteroatom-containing divalent linkage group, provided that, when each of $A_1$ and $A_2$ is single bond, all of the $R_{1a}$ to $R_{13a}$ groups do not simultaneously represent a fluorine atom and all of the $R_{1a}$ to $R_{13a}$ groups do not simultaneously represent a hydrogen atom; m represents an integer of 0 to 12; n represents an integer of 0 to 12; and q represents an integer of 1 to 3.

(12). The positive photosensitive composition as described in item (10), wherein the compound (A) comprises at least one of an iodonium salt of the sulfonic acid represented by formula (X) and sulfonium salt of the sulfonic acid represented by formula (X).

(13). The positive photosensitive composition as described in item (10), wherein the compound (A) comprises at least one compound selected from compounds represented by formulae (I) to (III):

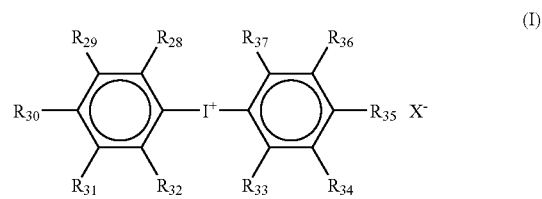

-continued

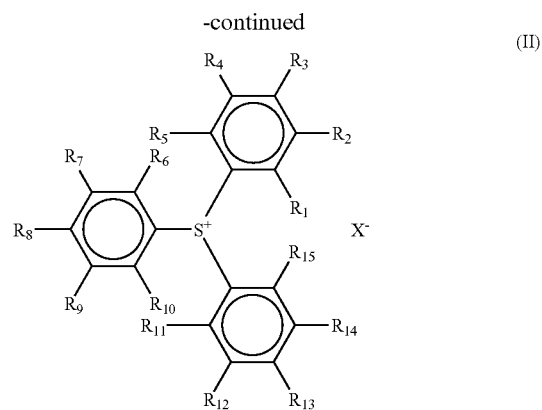

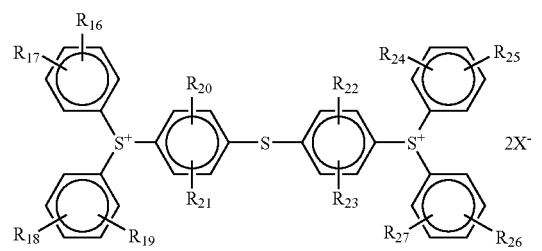

wherein $R_1$ to $R_{37}$ groups, which are the same or different, each represents a hydrogen atom, a straight-chain or branched alkyl group having 1 to 4 carbon atoms, a cycloalkyl group having 3 to 8 carbon atoms, a alkoxy group having 1 to 4 carbon atoms, a hydroxyl group, a halogen atom, or an —S—$R_{38}$ group; $R_{38}$ represents a straight-chain or branched alkyl group having 1 to 12 carbon atoms, a cycloalkyl group having 3 to 8 carbon atoms, or an aryl group having 6 to 14 carbon atoms; $X^-$ represents an anion of the sulfonic acid represented by formula (X) described above.

(14). The positive photosensitive composition as described in item (10), wherein at least one of the $R_{1a}$ to $R_{13a}$ groups in formula (X) represents a fluorine atom.

(15). The positive photosensitive composition as described in item (10), wherein the sulfonic acid represented by formula (X) comprises $CF_3CF_2$—O—$CF_2CF_2SO_3H$.

(16) The positive photosensitive composition as described in item (10), wherein the resin (D) contains at least one of a monocyclic alicyclic structure and polycyclic alicyclic structure.

(17). An iodonium or sulfonium salt compound represented by formulae (I) to (III):

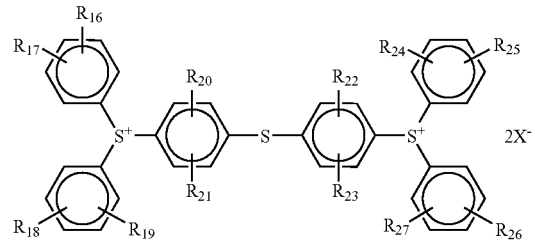

(III)

wherein $R_1$ to $R_{37}$ groups, which are the same or different, each represents a hydrogen atom, a straight-chain or branched alkyl group having 1 to 4 carbon atoms, a cycloalkyl group having 3 to 8 carbon atoms, a alkoxy group having 1 to 4 carbon atoms, a hydroxyl group, a halogen atom, or an —S—$R_{38}$ group; $R_{38}$ represents a straight-chain or branched alkyl group having 1 to 12 carbon atoms, a cycloalkyl group having 3 to 8 carbon atoms, or an aryl group having 6 to 14 carbon atoms; $X^-$ represents an anion of a sulfonic acid represented by formula (X);

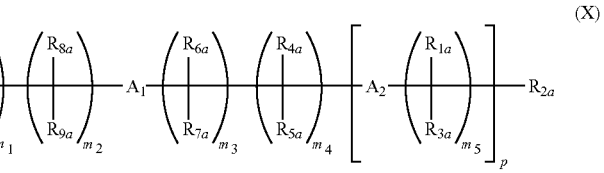

(X)

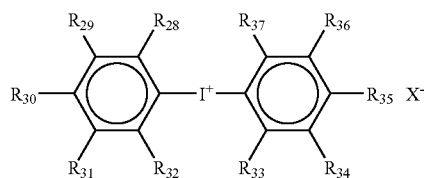

(I)

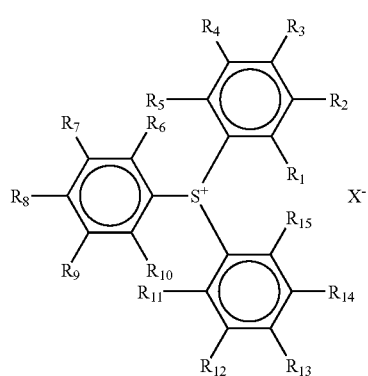

(II)

wherein $R_{1a}$ to $R_{13a}$ groups each represents a hydrogen atom, an alkyl group, a haloalkyl group, a halogen atom or a hydroxyl group; $A_1$ and $A_2$, which are the same or different, each represents a single bond or a hetero atom-containing divalent linkage group, provided that, when each of $A_1$ and $A_2$ is single bond, all of the $R_{1a}$ to $R_{13a}$ groups do not simultaneously represent a fluorine atom and all of the $R_{1a}$ to $R_{13a}$ groups do not simultaneously represent a hydrogen atom; $m_1$ to $m_5$, which are the same or different, each represents an integer of 0 to 12; and p represents an integer of 0 to 4.

(18). The iodonium or sulfonium salt compound as described in item (17), wherein the sulfonic acid represented by formula (X) is a compound represented by formula (X'):

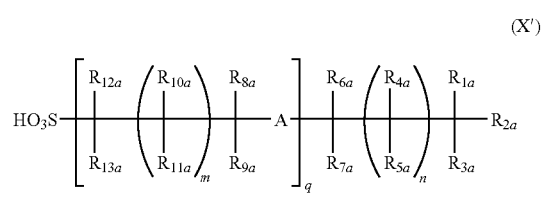

(X')

wherein $R_{1a}$ to $R_{13a}$ groups each represents a hydrogen atom, an alkyl group, a haloalkyl group, a halogen atom or a hydroxyl group; $A_1$ and $A_2$, which are the same or different, each represents a single bond or a hetero atom-containing divalent linkage group, provided that, when each of $A_1$ and $A_2$ is single bond, all of the $R_{1a}$ to $R_{13a}$ groups do not simultaneously represent a fluorine atom and all of the $R_{1a}$ to $R_{13a}$ groups do not simultaneously represent a hydrogen atom; m represents an integer of 0 to 12; n represents an integer of 0 to 12; and q represents an integer of 1 to 3.

Additionally, the present photosensitive compositions can deliver excellent resist performances even when electron beams are used as energy beams for irradiation. The irradiation with electron beams has a problem that the incident beams interact with atomic nuclei and electrons of ingredients in resist because of their electric charges, so that when electron beams is launched into a resist film a scattering phenomenon takes place to degrade a pattern profile.

Another problem of electron beams is in that, even when electron beams are irradiated in a reduced beam diameter with the intention of forming fine patterns, the area irradiated with them is broadened due to the scattering phenomenon described above and thereby the resolution is lowered.

These problems of irradiation with electron beams are, however, solved well by the present compositions.

DETAILED DESCRIPTION OF THE INVENTION

The invention includes:

1. A positive photosensitive composition comprising:
(A) a compound capable of generating a sulfonic acid represented by formula (X) above upon irradiation with one of an actinic ray and radiation; and
(B) a resin capable of decomposing under the action of an acid to increase the solubility in an alkali developer (hereinafter referred to as "the first composition"), and 2. A positive photosensitive composition comprising:
(A) a compound capable of generating a sulfonic acid represented by formula (X) below upon irradiation with one of an actinic ray and radiation;
(C) a dissolution-inhibiting compound having a molecular weight of not more than 3,000 which contains an acid-decomposable group and can increase the solubility in an alkali developer by the action of an acid; and
(D) a resin insoluble in water and soluble in an alkali developer (hereinafter referred to as "the second composition").

When the simple expression of "positive photosensitive composition" or "composition" is used hereinafter, it includes both the first composition and the second composition mentioned above.

Additionally, the term "an actinic ray and radiation" used in the invention is intended to include far ultraviolet rays (such as KrF excimer laser and ArF excimer laser), electron beams, X-rays and ion beams.

The compounds, resins and other components contained in the present positive photosensitive compositions are described below in greater detail.

[Description of Components Contained in Compositions]

<<Photo-Acid Generators>>

Photo-acid generators used in the invention are compounds capable of generating sulfonic acids represented by the foregoing formula (X) upon irradiation with actinic rays or radiation (hereinafter referred to as "Component (A)" or "sulfonic acid-generators"). Of these compounds, the compounds capable of generating sulfonic acids represented by the foregoing formula (X') are preferred over the others.

In formula (X) or (X'), the alkyl groups represented by $R_{1a}$ to $R_{13a}$ groups include alkyl groups having 1 to 12 carbon atoms, such as methyl, ethyl, propyl, n-butyl, sec-butyl and t-butyl, which may have substituent groups.

The haloalkyl groups represented by $R_{1a}$ to $R_{13a}$ groups are alkyl groups substituted with a halogen atom, and include alkyl groups having 1 to 12 carbon atoms which are substituted with at least one of fluorine atom, chlorine atom, bromine atom and iodine atom, and the preferable haloalkyl groups are alkyl groups substituted with a fluorine atom.

The halogen atoms represented by $R_{1a}$ to $R_{13a}$ groups include fluorine, chlorine and iodine atoms.

As examples of substitutents the foregoing alkyl groups may have, mention may be made of alkoxy groups having 1 to 4 carbon atoms, halogenatoms (e.g., fluorine, chlorine, iodine), aryl groups having 6 to 10 carbon atoms, alkenyl groups having 2 to 6 carbon atoms, a cyano group, a hydroxyl group, a carboxyl group, alkoxycarbonyl groups and a nitro group.

Examples of a hetero atom-containing divalent linkage group represented by $A_1$, $A_2$ or A include —O—, —S—, —CO—, —COO—, —CONR—, —SO$_2$NR—, —CONRCO—, —SO$_2$NRCO—, —SO$_2$NRSO$_2$— and —OCONR—.

Herein, R represents a hydrogen atom, or an alkyl group having 1 to 10 carbon atoms, which may be substituted with a halogen atom, a hydroxyl group or an alkoxy group. Further, R may combine with at least one of the $R_{1a}$ to $R_{13a}$ groups to form a ring. And the ring formed may contain a linkage group, such as an oxygen atom, a nitrogen atom, a sulfur atom or —CO—.

As the sulfonic acids of formula (X) or (X'), cases are suitable where at least one of the $R_{1a}$ to $R_{13a}$ groups represents a halogen atom, especially a fluorine atom. In particular, it is preferable that either the $R_{12a}$ or $R_{13a}$ group or both of these groups in formula (X) or (X') are fluorine atoms.

Of these sulfonic acids, $CF_3(CF_2)_k[A(CF_2)_{k'}]_qSO_3H$, $CF_3(CF_2)_k(CH_2)_{k'}SO_3H$, $CH_3(CH_2)_k(CF_2)_{k'}SO_3H$ (wherein k is an integer of 0 to 12, k' is an integer of 1 to 12, and A and q respectively have the same meanings as the above) and compounds represented by the following formula are preferred over the others, especially $CF_3CF_2$—O—$CF_2CF_2SO_3H$ is preferable:

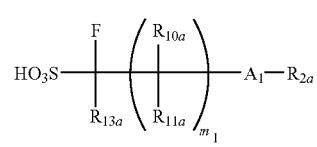

Herein, $m_1$ is an integer of 0 to 3, preferably 0 or 1, and $A_1$ preferably represents a single bond, —O—, —CONR— or —COO—.

Further, it is preferable that the number of fluorine atoms contained in the sulfonic acid of formula (X) be not more than 20, preferably not more than 15, particularly preferably not more than 9. Furthermore, in view of improvement in affinity of the acid generator for water, it is preferable that the number of fluorine atoms contained in the sulfonic acid is smaller than that of hydrogen atoms.

As Component (A) of the present invention, sulfonium or iodonium salts of sulfonic acids represented by the foregoing formula (X) are suitable from the viewpoints of sensitivity and resolution.

The sulfonium salts are more suitable, and they enable further improvement in storage stability.

Specifically, compounds having structures represented by the following formulae (I) to (III) are preferred as Component (A):

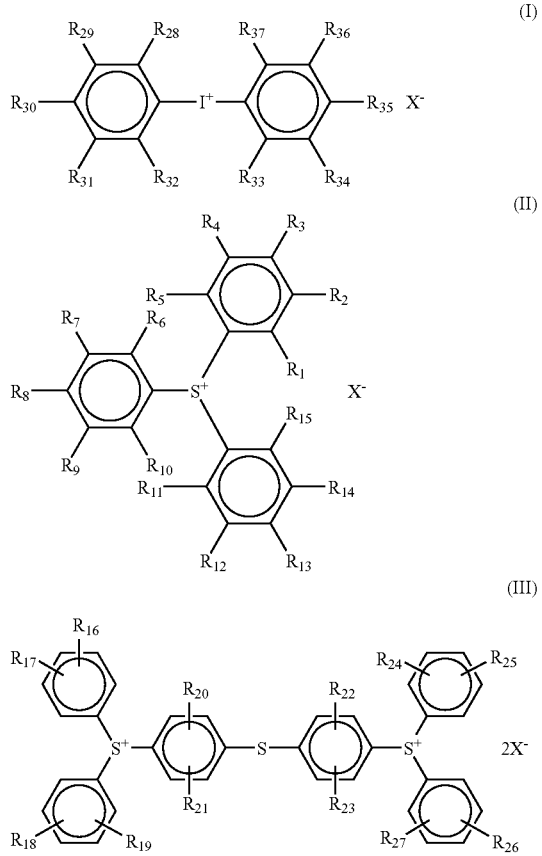

wherein $R_1$ to $R_{37}$ groups each represent a hydrogen atom, a straight-chain, branched or cyclic alkyl group, a straight-chain, branched or cyclic alkoxy group, a hydroxyl group, a halogen atom or an —S—$R_{38}$ group, $R_{38}$ represents a straight-chain, branched or cyclic alkyl group or an aryl group, and $X^-$ represents an anion of sulfonic acid represented by formula (X).

As examples of a straight-chain or branched alkyl group represented by $R_1$ to $R_{38}$ groups each, mention may be made of alkyl groups having 1 to 4 carbon atoms, including methyl, ethyl, propyl, n-butyl, sec-butyl and t-butyl groups, which each may have a substituent group.

As examples of a cyclic alkyl group represented by $R_1$ to $R_{38}$ groups each, mention may be made of cycloalkyl groups having 3 to 8 carbon atoms, including cyclopropyl, cyclopentyl and cyclohexyl groups, which each may have a substituent group.

As examples of an alkoxy group represented by $R_1$ to $R_{37}$ groups each, mention may be made of alkoxy groups having 1 to 4 carbon atoms, including methoxy, ethoxy, hydroxyethoxy, propoxy, n-butoxy, isobutoxy, sec-butoxy and t-butoxy groups.

As examples of a halogen atom represented by $R_1$ to $R_{37}$ groups each, mention may be made of fluorine, chlorine, bromine and iodine atoms.

As examples of an aryl group represented by $R_{38}$, mention may be made of unsubstituted or substituted aryl groups having 6 to 14 carbon atoms, including phenyl, tolyl, methoxyphenyl and naphthyl groups.

As examples of a substituent group which each of the groups as recited above may have, mention may be made of alkoxy groups having 1 to 4 carbon atoms, halogen atoms (e.g., fluorine, chlorine, iodine), aryl groups having 6 to 10 carbon atoms, alkenyl groups having 2 to 6 carbon atoms, a cyano group, a hydroxyl group, a carboxyl group, alkoxycarbonyl groups and a nitro group.

Every iodonium compound of formula (I) and sulfonium compound of formula (II) or (III) which can be used in the invention contains as counter anion $X^-$ an anion of sulfonic acid represented by formula (X).

Such an anion is an anion (—$SO_3^-$) formed by departure of a hydrogen atom from the sulfonic acid group (—$SO_3H$).

In addition, aromatic ring-free sulfonium salts and phenacyl sulfonium salts are also suitable as Component (A).

As examples of such aromatic ring-free sulfonium salts, mention may be made of salts containing sulfonium represented by the following formula (IV) as their cation:

wherein $R^{1b}$ to $R^{3b}$ groups independently represent an organic group having no aromatic ring. The term "aromatic ring" used herein is intended to include hetero atom-containing aromatic rings also.

The number of carbon atoms contained in the aromatic ring-free organic group as each of the $R^{1b}$ to $R^{3b}$ groups is generally from 1 to 30, preferably from 1 to 20.

Specifically, it is preferable that $R^{1b}$ to $R^{3b}$ groups each represent an alkyl group, a 2-oxoalkyl group, an alkoxycarbonylmethyl group, an allyl group or a vinyl group, preferably a straight-chain, branched or cyclic 2-oxoalkyl group, or an alkoxycarbonylmethyl group, particularly preferably a straight-chain or branched 2-oxoalkyl group.

The alkyl group as each of $R^{1b}$ to $R^{3b}$ groups, though may have any of straight-chain, branched and cyclic forms, preferably includes straight-chain or branched alkyl groups having 1 to 10 carbon atoms (such as methyl, ethyl, propyl, butyl, pentyl) and cycloalkyl groups having 3 to 10 carbon atoms (e.g., cyclopentyl, cyclohexyl, norbornyl).

The 2-oxoalkyl group as each of $R^{1b}$ to $R^{3b}$ groups, though may have any of straight-chain, branched and cyclic forms, preferably includes the groups having the same alkyl moieties as the alkyl groups recited above and >C=O at the 2-positions thereof.

The alkoxy moiety of an alkoxycarbonylmethyl group as each of $R^{1b}$ to $R^{3b}$ groups is preferably an alkyl group having 1 to 5 carbon atoms (e.g., methyl, ethyl, propyl, butyl, pentyl).

Each of the groups represented by $R^{1b}$ to $R^{3b}$ may further be substituted with a halogen atom, an alkoxy group (containing, e.g., 1 to 5 carbon atoms), a hydroxyl group, a cyano group or a nitro group.

Any two of $R^{1b}$ to $R^{3b}$ groups may combine with each other to from a ring structure, and in the ring formed may be contained an oxygen atom, a sulfur atom, an ester linkage, an amide linkage or a carbonyl group. As examples of a group formed by combining any two of $R^{1b}$ to $R^{3b}$ groups, mention may be made of alkylene groups (e.g., butylene, pentylene).

From the viewpoint of photo-reactivity, it is preferable that one of $R^{1b}$ to $R^{3b}$ groups is a group having a carbon-carbon double bond or a carbon-oxygen double bond.

As to the compounds represented by formula (IV), a structure may be taken that at least one of $R^{1b}$ to $R^{3b}$ groups present in one compound is bound to at least one of $R^{1b}$ to $R^{3b}$ groups present in another compound.

The aromatic ring-free sulfonium salts contain anions of sulfonic acids represented by formula (X) as their counter anions.

Examples of a compound having a phenacyl sulfonium salt structure include compounds represented by the following formula (V):

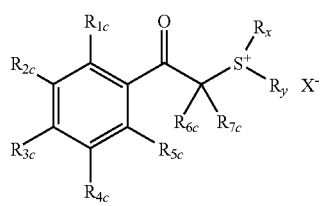

(V)

wherein $R_{1c}$ to $R_{5c}$ groups independently represent a hydrogen atom, an alkyl group, an alkoxy group, or a halogen atom; $R_{6c}$ and $R_{7c}$ groups independently represent a hydrogen atom, an alkyl group, or an aryl group; Rx and Ry groups independently represent an alkyl group, a 2-oxoalkyl group, an alkoxycarbonylmethyl group, an allyl group or a vinyl group; or at least two of $R_{1c}$ to $R_{7c}$ groups may combine with each other to form a ring structure, or Rx and Ry may combine with each other to form a ring structure, and the ring structure formed may contain an oxygen atom, a sulfur atom, an ester linkage or an amide linkage; and $X^-$ is an anion of sulfonic acid represented by formula (X).

The alkyl groups as $R_{1c}$ to $R_{5c}$ may have any of straight-chain, branched and cyclic forms, and examples thereof include alkyl groups having 1 to 10 carbon atoms, preferably 1 to 5 carbon atoms, straight-chain and branched alkyl groups (such as a methyl group, an ethyl group, straight-chain and branched propyl groups, straight-chain and branched butyl groups, and straight-chain and branched pentyl groups), and cycloalkyl groups having 3 to 8 carbon atoms (such as cyclopentyl and cyclohexyl groups).

The alkoxy groups as $R_{1c}$ to $R_{5c}$ may have any of straight-chain, branched and cyclic forms, and examples thereof include alkoxy groups having 1 to 10 carbon atoms, preferably 1 to 5 carbon atoms, straight-chain and branched alkoxy groups (such as a methoxy group, an ethoxy group, straight-chain and branched propoxy groups, straight-chain and branched butoxy groups, and straight-chain and branched pentoxy groups), and cycloalkoxy groups having 3 to 8 carbon atoms (such as cyclopentyloxy and cyclohexyloxy groups).

As to the compounds represented by formula (V), it is preferable that anyone of $R_{1c}$ to $R_{5c}$ be a straight-chain, branched or cyclic alkyl or alkoxy group. Further, the total number of carbon atoms contained in $R_{1c}$ to $R_{5c}$ groups is preferably from 2 to 15. By being so designed, the compounds can have increased solvent solubilities and inhibit particle generation upon storage.

Examples of alkyl groups as $R_{6c}$ and $R_{7c}$ include the same alkyl groups as $R_{1c}$ to $R_{5c}$. And examples of aryl groups as $R_{6c}$ and $R_{7c}$ include aryl groups having 6 to 14 carbon atoms (e.g., phenyl).

Examples of alkyl groups as Rx and Ry include the same alkyl groups as $R_{1c}$ to $R_{5c}$.

The 2-oxoalkyl group as Rx and Ry groups each includes the groups having $>C=O$ at the 2-positions of the alkyl groups recited as those for $R_{1c}$ to $R_{5c}$ groups.

Examples of an alkoxy moiety in the alkoxycarbonylmethyl group as Rx and Ry groups each include the same alkoxy groups as recited above with respect to the $R_{1c}$ to $R_{5c}$ groups.

Examples of a group formed by combining Rx with Ry include a butylene group and a pentylene group.

Examples of a compound usable as Component (A) (including compounds represented by formulae (I) to (V)) are illustrated below. However, these examples should not be construed as limiting the scope of the invention in any way.

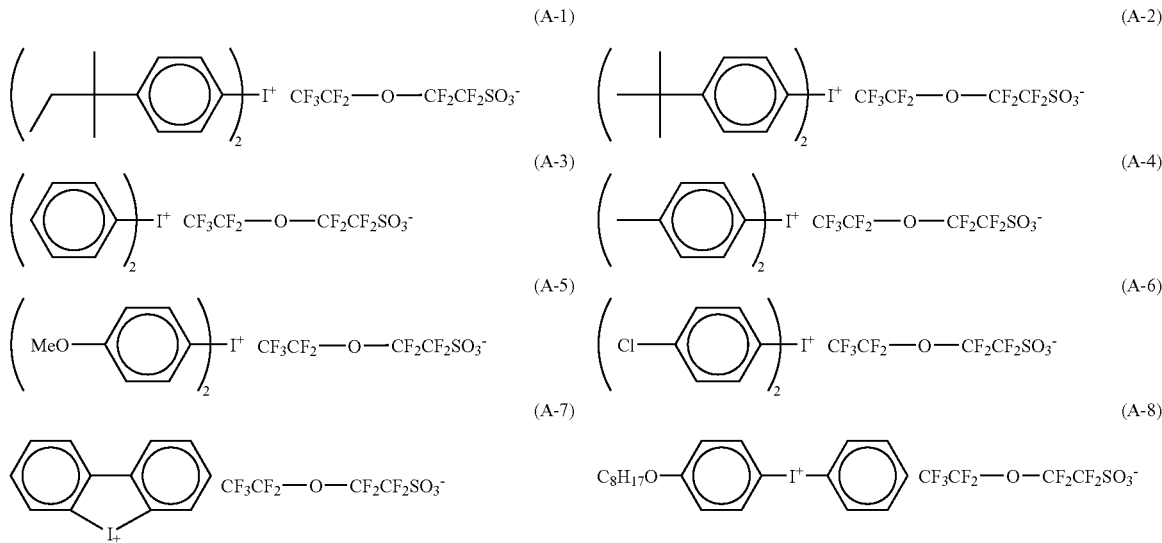

-continued
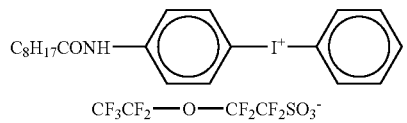 (A-9)
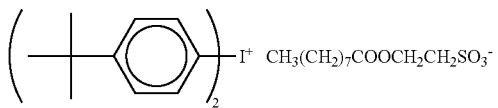 (A-10)
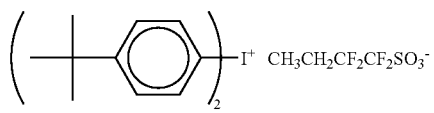 (A-11)
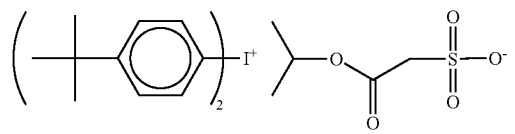 (A-12)
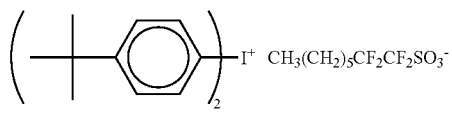 (A-13)
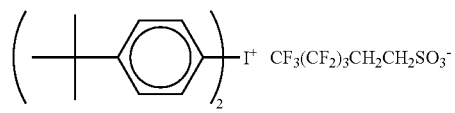 (A-14)
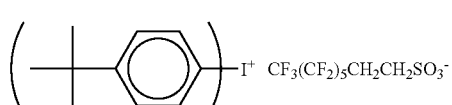 (A-15)
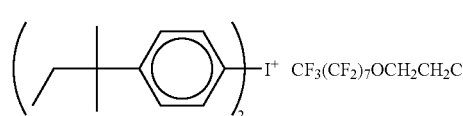 (A-16)
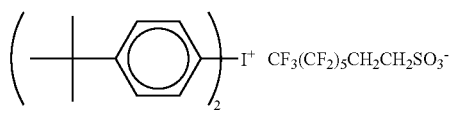 (A-17)
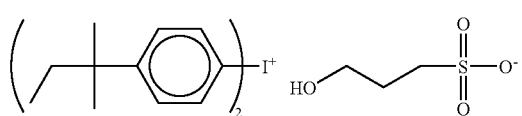 (A-18)
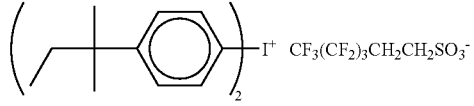 (A-19)
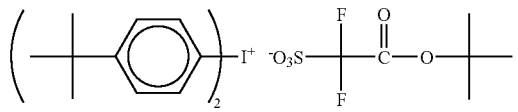 (A-20)
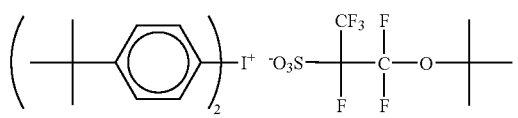 (A-21)
(A-22)
(A-23)
(A-24)
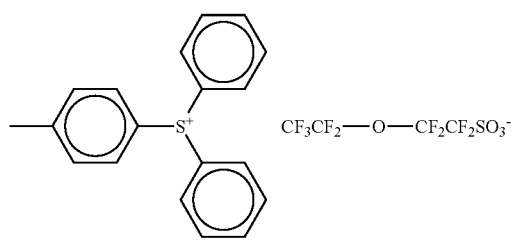 (A-25)
(A-26)

-continued
(A-27)
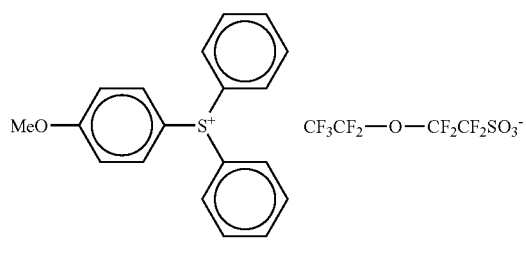
(A-28)
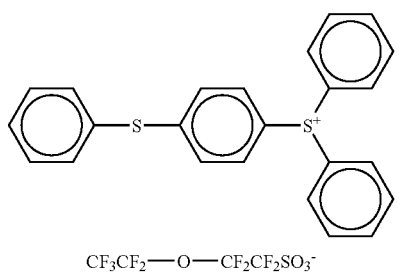
(A-29)
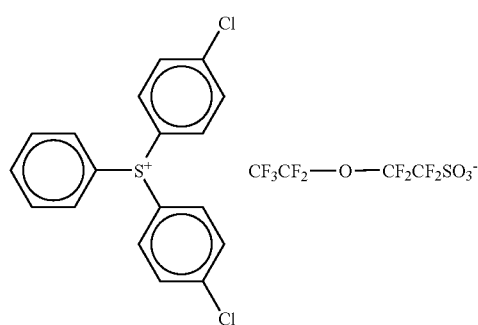
(A-30)
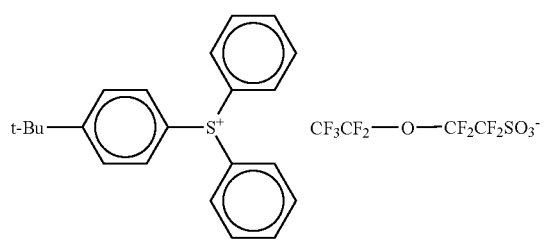
(A-31)
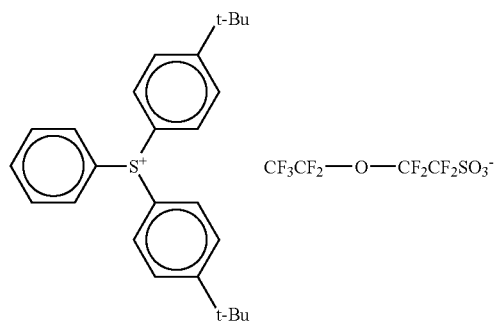
(A-32)
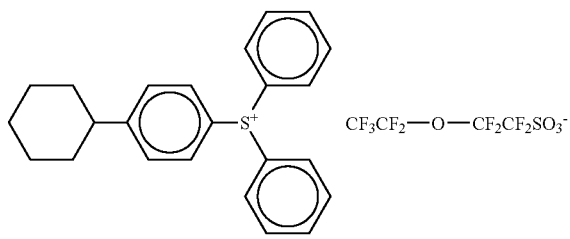
(A-33)
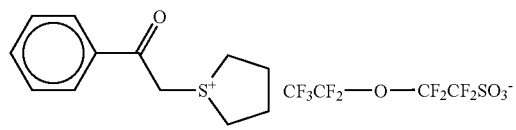
(A-34)
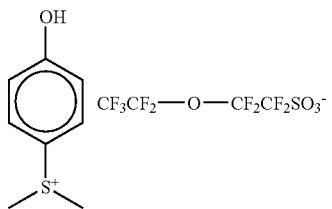
(A-35)
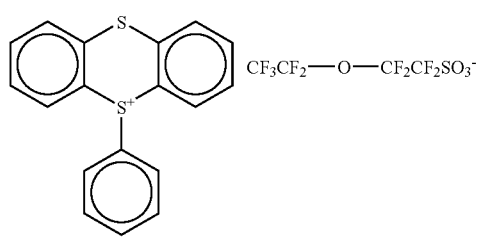
(A-36)
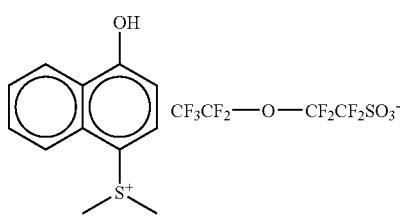

-continued
(A-37)
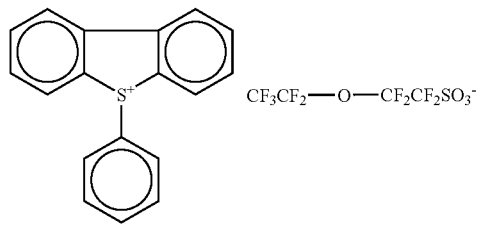
(A-38)
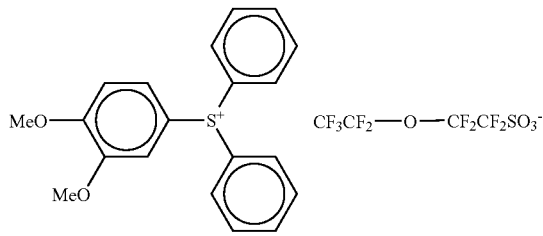
(A-39)
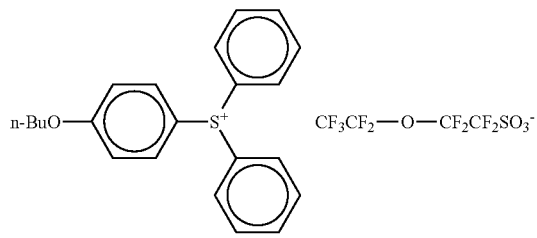
(A-40)
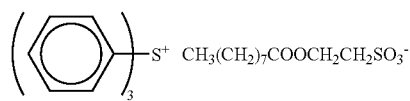
(A-41)
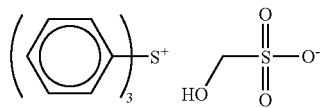
(A-42)
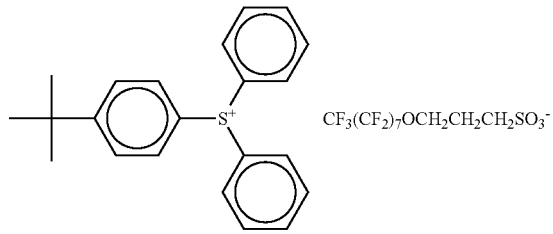
(A-43)
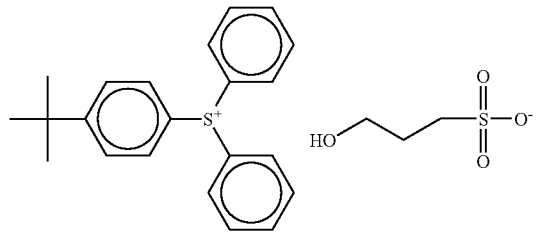
(A-44)
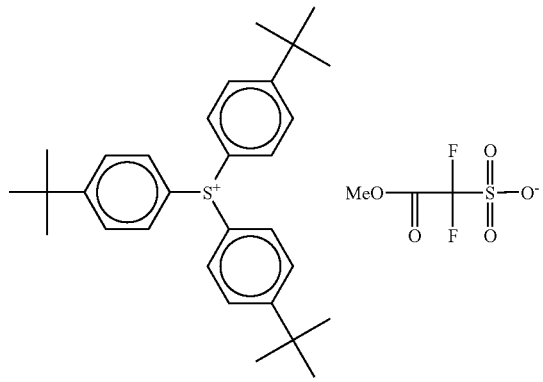
(A-45)
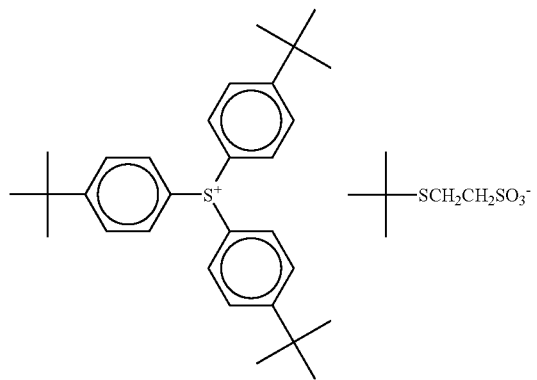
(A-46)
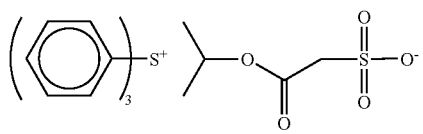

-continued
(A-47)
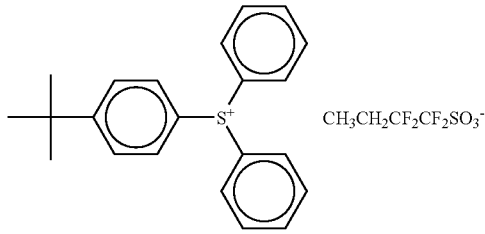
(A-48)
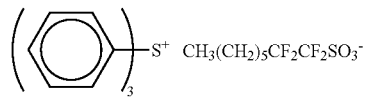
(A-49)
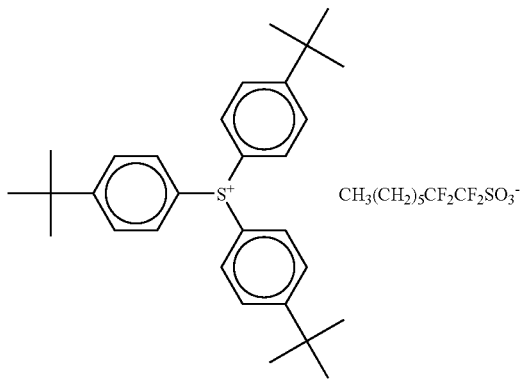
(A-50)
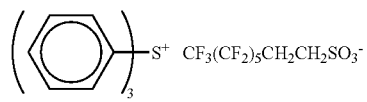
(A-51)
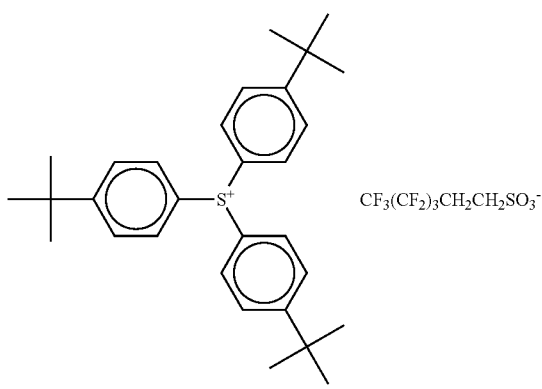
(A-52)
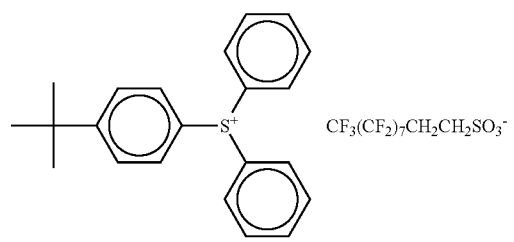
(A-53)
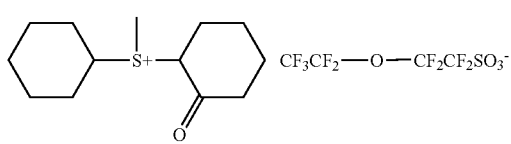
(A-54)
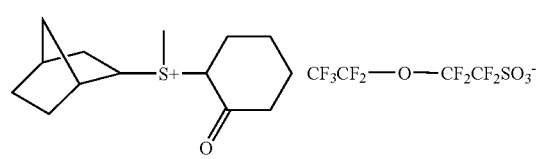
(A-55)
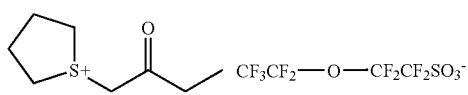
(A-56)
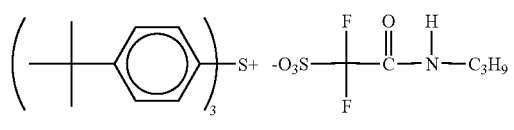
(A-57)
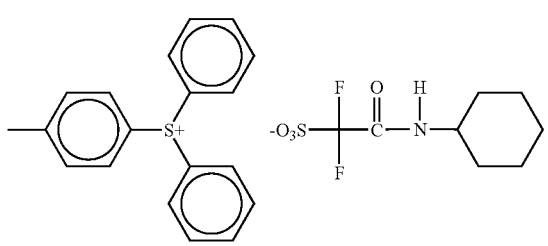
(A-58)
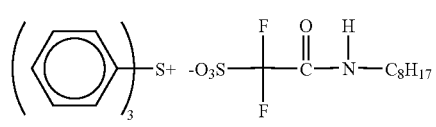

-continued
(A-59) 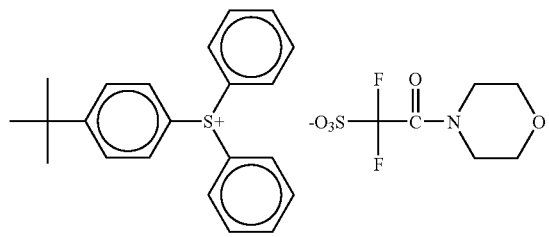
(A-60) 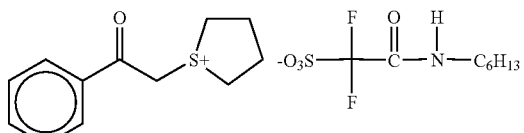
(A-61) 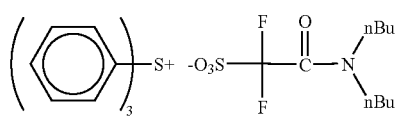
(A-62) 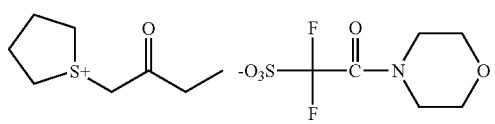
(A-63) 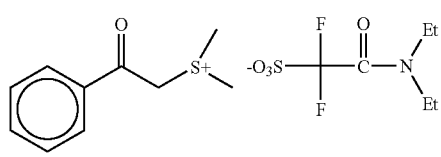
(A-64) 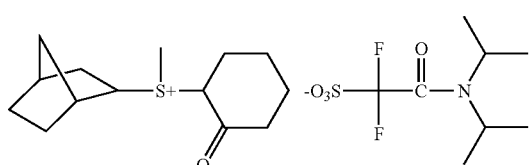
(A-65) 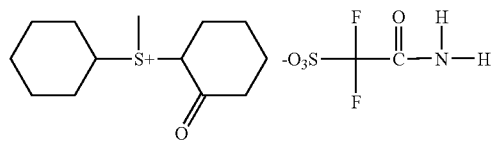
(A-66) 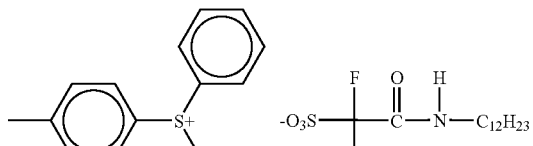
(A-67) 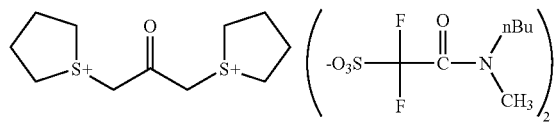
(A-68) 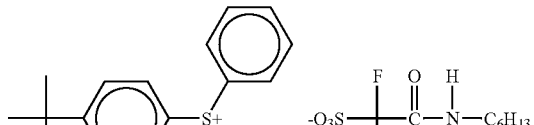
(A-69) 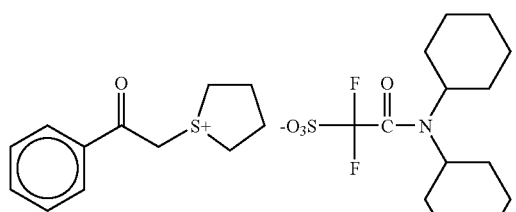
(A-70) 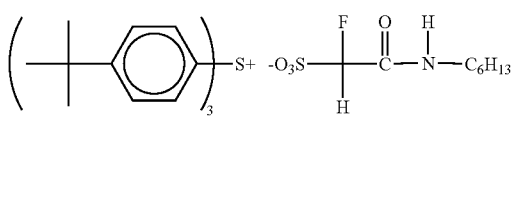
(A-71) 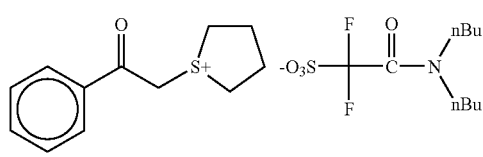
(A-72) 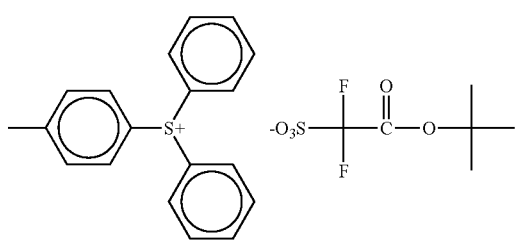

-continued
(A-73) 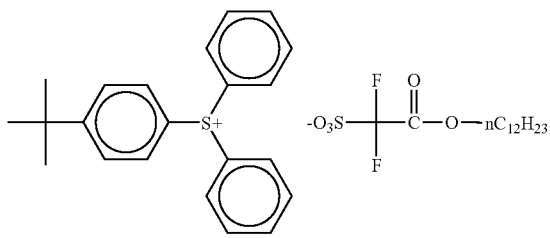 (A-74) 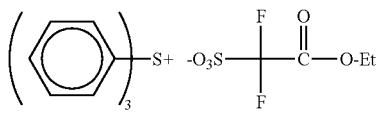
(A-75) 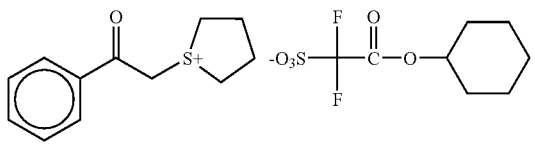 (A-76) 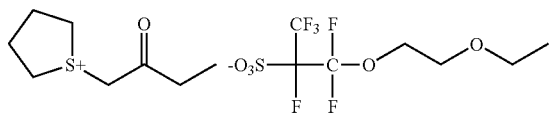
(A-77) 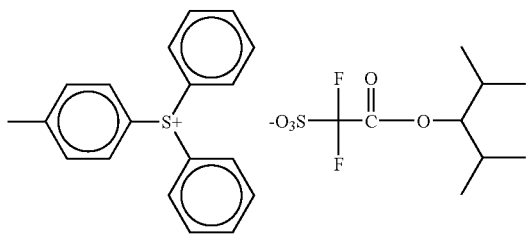 (A-78) 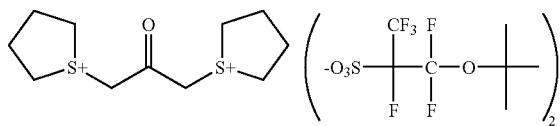
(A-79) 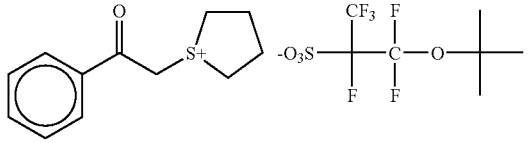 (A-80) 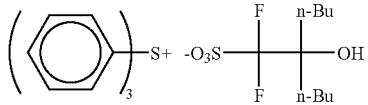
(A-81) 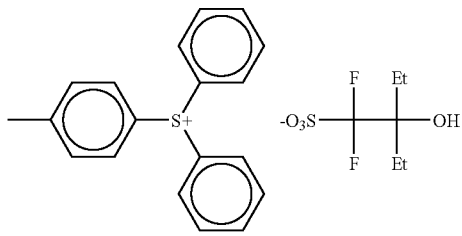 (A-82) 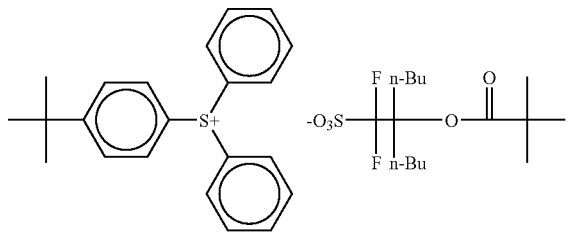
(A-83) 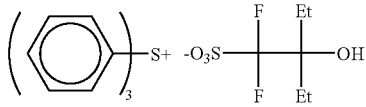 (A-84) 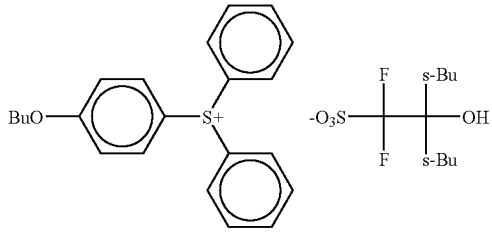
(A-85) 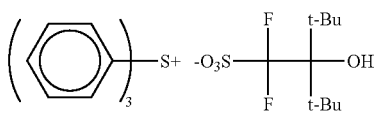 (A-86) 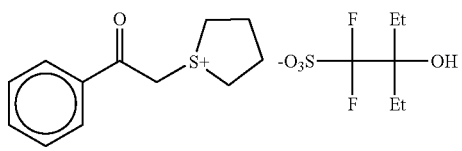

-continued
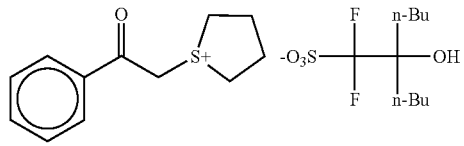 (A-87)
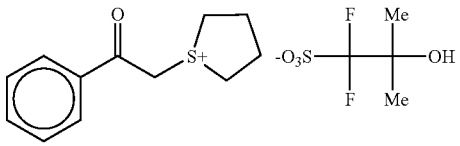 (A-88)
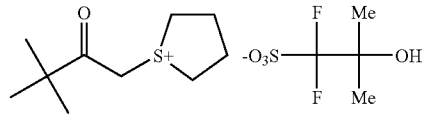 (A-89)
(A-90)
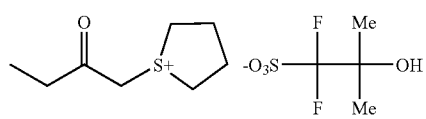 (A-91)
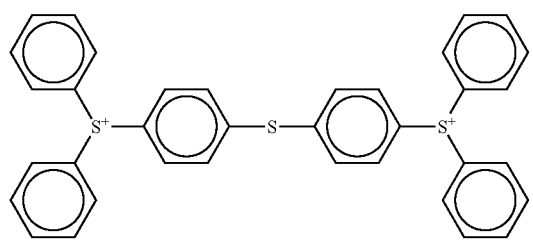 (A-92)
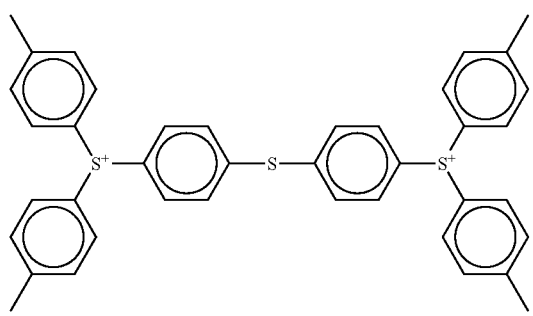 (A-93)
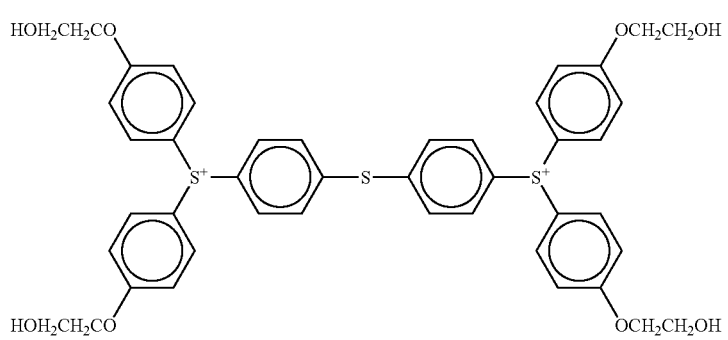 (A-94)
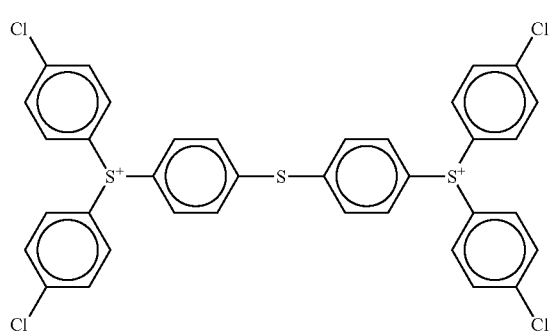 (A-95)

-continued
(A-96)
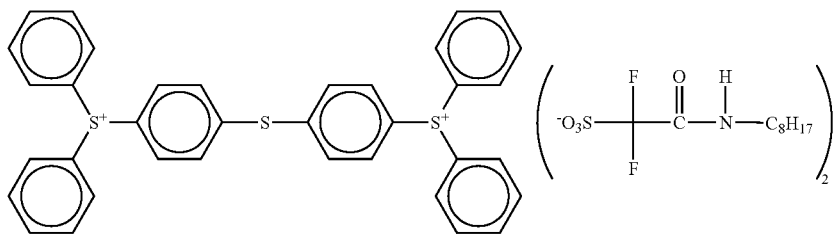
(A-97)
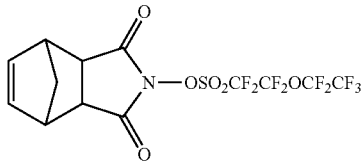
(A-98)
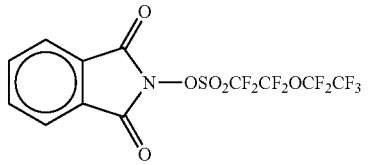
(A-99)
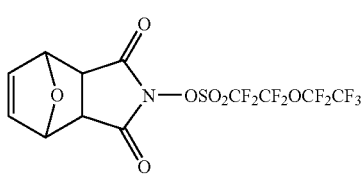
(A-100)
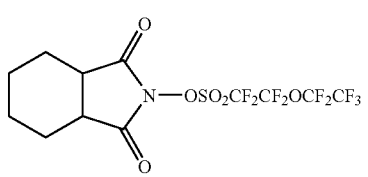
(A-101)
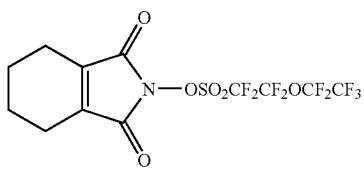
(A-102)
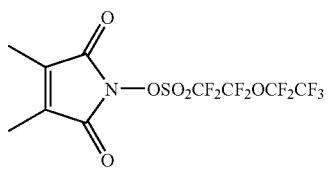
(A-103)
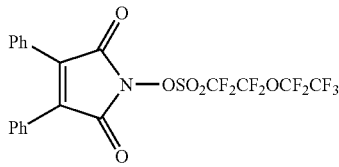
(A-104)
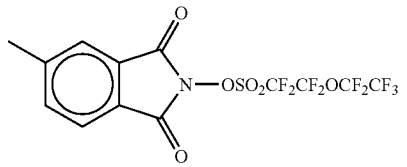
(A-105)
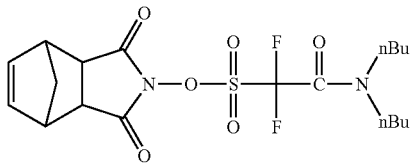
(A-106)
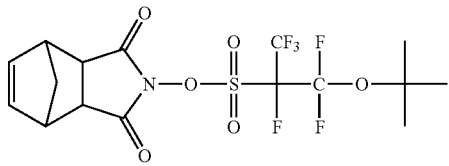
(A-107)
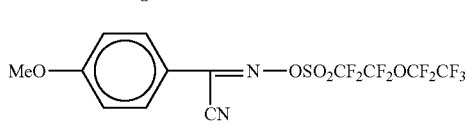
(A-108)
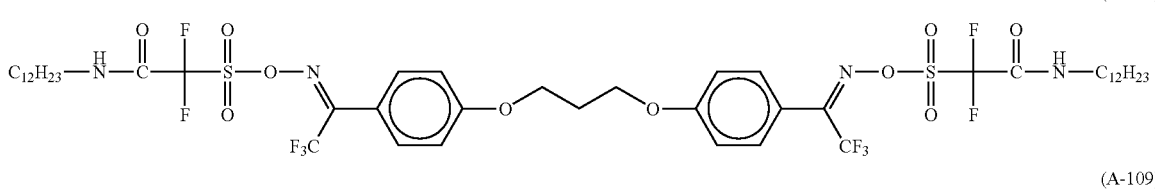
(A-109)
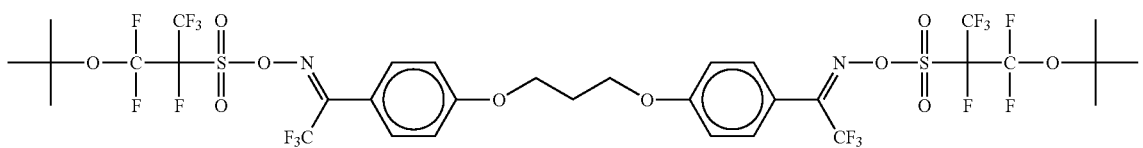

-continued

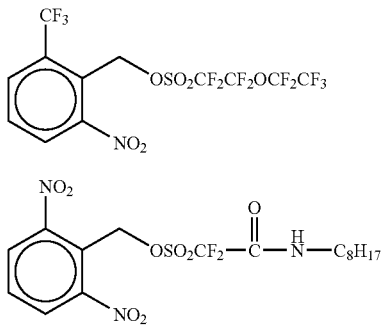

(A-110)

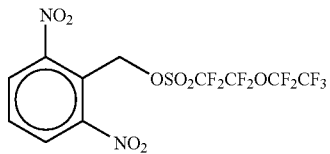

(A-111)

(A-112)

The Compounds (A-14), (A-15), (A-19), (A-20), (A-50), (A-51) and (A-52) illustrated above are each prepared using as starting materials sulfonic acids synthesized via telomerization. Therefore, each of them is a mixture containing at least 60% of the compound illustrated and sulfonic acid salts differing in fluoroalkyl chain length.

Compounds represented by formula (I) as Component (A) can be synthesized by reacting aromatic compounds with periodate, and then subjecting the resulting iodonium salts to salt exchange reaction using the corresponding sulfonic acids.

Compounds represented by formula (II) and those represented by formula (III) can be synthesized by reacting aryl Grignard reagents, such as arylmagnesium bromides, with substituted or unsubstituted phenyl sulfoxide, and then subjecting the resulting triarylsulfonium halides to salt exchange reaction using the corresponding sulfonic acids.

Further, those compounds can be synthesized using a method in which substituted or unsubstituted phenyl sulfoxide and the corresponding aromatic compounds are condensed in the presence of an acid catalyst, such as methanesulfonic acid/diphosphorus pentoxide or aluminum chloride, and then the condensation products are subjected to salt exchange reaction, or a method of condensing diaryl iodonium salts and diaryl sulfide in the presence of a catalyst such as copper acetate, and then subjecting the condensation products to salt exchange reaction.

The salt exchange reaction can be effected by a method in which the halide salts once derived are converted to sulfonic acid salts with the aid of a silver reagent, such as silver oxide, or ion exchange resins. The sulfonic acids or sulfonic acid salts used for the salt exchange reaction are commercially available or can be prepared by hydrolysis of commercially available sulfonic acid halides.

The foregoing compounds as Component (A) can be used alone or as various combinations thereof.

The suitable proportion of the compound(s) as Component (A) in the present positive photosensitive composition is from 0.1 to 20 weight %, preferably from 0.5 to 10 weight %, particularly preferably from 1 to 7 weight %, on a solids basis.

<Other Photo-Acid Generators Usable Together with Compounds as Component (A)>

In addition to the compounds defined above as Component (A), other compounds capable of decomposing upon irradiation with actinic rays or radiation to generate acids may be used in the invention.

The mole ratio of the compound(s) as Component (A) to photo-acid generators used together therewith is generally from 100/0 to 20/80, preferably from 100/0 to 40/60, particularly preferably from 100/0 to 50/50.

The photo-acid generators used together with the compound(s) as Component (A) can be selected preferably from photo-initiators for cationic photopolymerization, photo-initiators for radical photopolymerization, photodecolouring agents for dyes, photodiscolouring agents, compounds known to be used in microresist and capable of generating acids by irradiation with actinic rays or radiation, or mixtures of two or more of the agents recited above.

Examples of such photo-acid generators include onium salts, such as diazonium salts, ammonium salts, phosphonium salts, iodonium salts, sulfonium salts, selenonium salts and arsonium salts, organic halogen compounds, organometal-organic halide compounds, photo-acid generators having o-nitrobenzyl type protective groups, compounds capable of generating sulfonic acid by photolysis, typified by iminosulfonates, and disulfone compounds.

In addition, polymers having main or side chains into which are introduced those groups or compounds capable of generating acids upon irradiation with actinic rays or radiation, as described in U.S. Pat. No. 3,849,137, German Patent 3914407, JP-A-63-26653, JP-A-55-164824, JP-A-62-69263, JP-A-63-146038, JP-A-63-163452, JP-A-62-153853 and JP-A-63-146029, can be used.

Also, the compounds capable of generating acids under light, as described in U.S. Pat. No. 3,779,778 and European Patent 126,712, can be used.

Of the above-recited photo-acid generators which can be used together with the compound(s) as Component (A), the following compounds are used to particular advantage.

(1) Trihalomethyl-substituted oxazole compounds represented by the following formula (PAG1) or trihalomethyl-substituted s-triazine compounds represented by the following formula (PAG2):

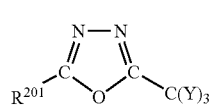

(PAG1)

-continued

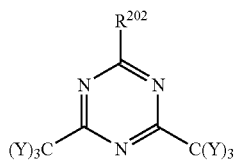
(PAG2)

In the above formulae, $R^{201}$ represents a substituted or unsubstituted aryl or alkenyl group, $R^{202}$ represents a substituted or unsubstituted aryl, alkenyl or alkyl group, or —C$(Y)_3$, and Y represents a chlorine or bromine atom.

Examples of such compounds are illustrated below, but the compounds usable in the invention should not be construed as being limited to these examples.

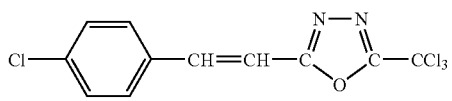
(PAG1-1)

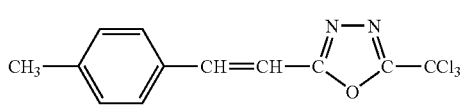
(PAG1-2)

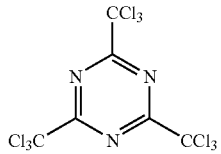
(PAG2-1)

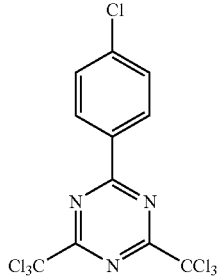
(PAG2-2)

(2) Iodonium salts represented by the following formula (PAG3) or sulfonium salts represented by the following formula (PAG4):

(PAG3)

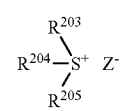
(PAG4)

In the above formulae, $Ar^1$ and $Ar^2$ independently represent a substituted or unsubstituted aryl group. Examples of a substituent suitable for the aryl group include an alkyl group, a haloalkyl group, a cycloalkyl group, an aryl group, an alkoxy group, a nitro group, a carboxyl group, an alkoxycarbonyl group, a hydroxyl group, a mercapto group and a halogen atom.

$R^{203}$, $R^{204}$ and $R^{205}$ independently represent a substituted or unsubstituted alkyl or aryl group, preferably a 6-14C aryl group which may have a substituent, or a 1-8C alkyl group which may have a substituent.

Examples of a substituent suitable for such an aryl group include a 1-8C alkoxy group, a 1-8C alkyl group, a nitro group, a carboxyl group, a hydroxyl group and a halogen atom, and those for such an alkyl group include a 1-8C alkoxy group, a carboxyl group and an alkoxycarbonyl group.

$Z^-$ represents a counter anion, with examples including $BF_4^-$, $AsF_6^-$, $PF_6^-$, $SbF_6^-$, $SiF_6^-$, $ClO_4^-$, perfluoroalkanesulfonic acid anions such as $CF_3SO_3^-$, pentafluorobenzenesulfonic acid anion, condensed polynuclear aromatic sulfonic acid anions such as naphthalene-1-sulfonic acid anion, anthraquinonesulfonic acid anion, and sulfonic acid group-containing dyes. However, $Z^-$ should not be construed as being limited to these examples.

Further, any two among $R^{203}$, $R^{204}$ and $R^{205}$, or $Ar^1$ and $Ar^2$ may be bound to each other via a single bond or a substituent.

Examples of onium salts as defined above are illustrated below. However, the onium salts usable in the invention should not be construed as being limited to these examples.

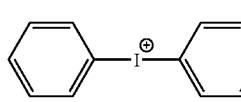 
(PAG3-1)

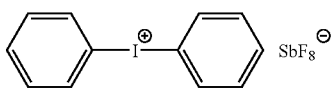
(PAG3-2)

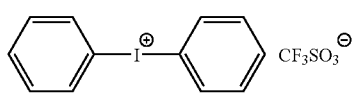
(PAG3-3)

-continued
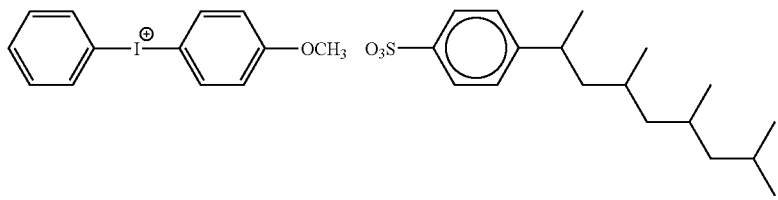
(PAG3-4)
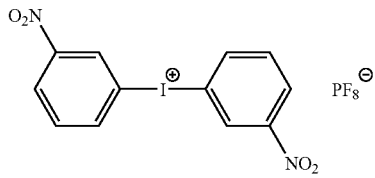
(PAG3-5)
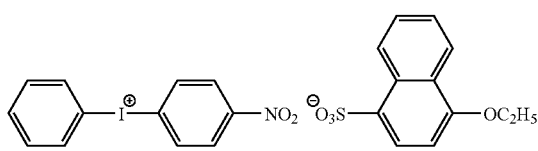
(PAG3-6)
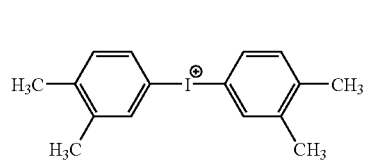
(PAG3-7)
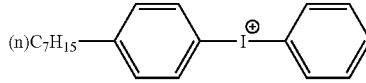
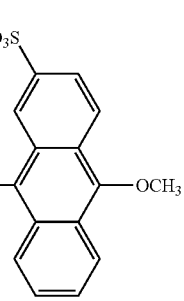
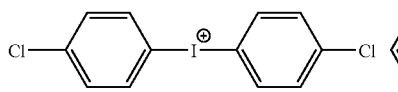
(PAG3-9)
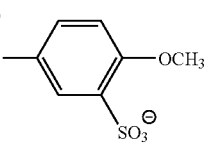
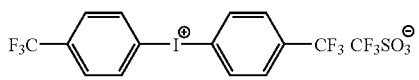
(PAG3-10)
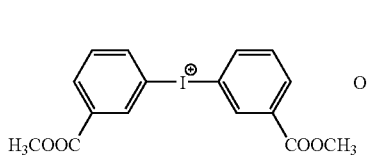
(PAG3-11)
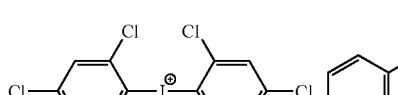
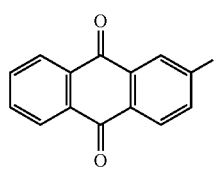
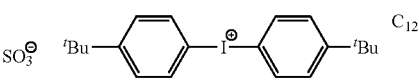
(PAG3-13)
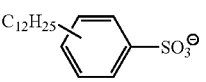

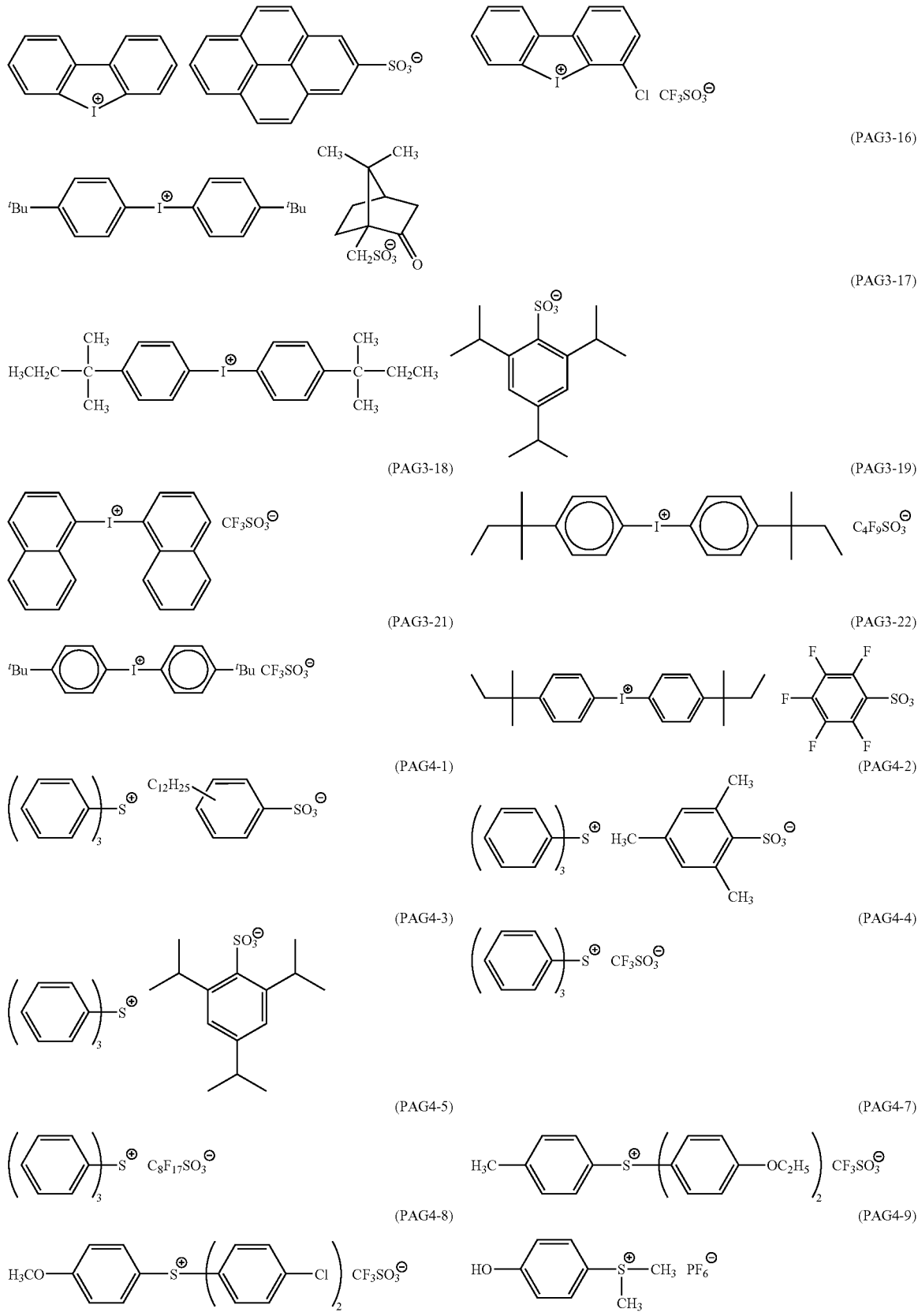

-continued
(PAG4-10) 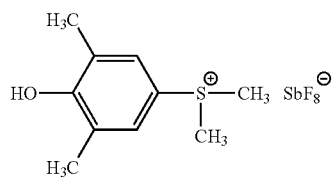
(PAG4-11) 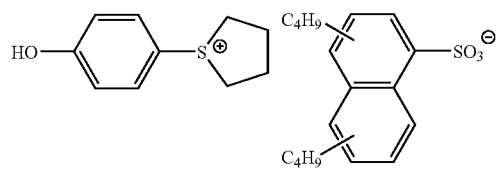
(PAG4-12) 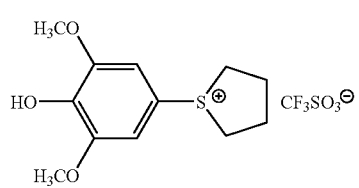
(PAG4-13) 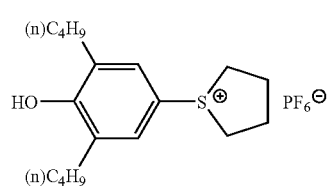
(PAG4-14) 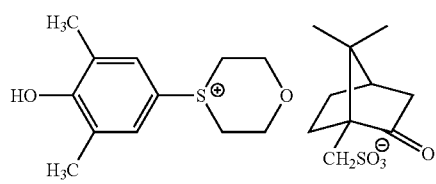
(PAG4-15) 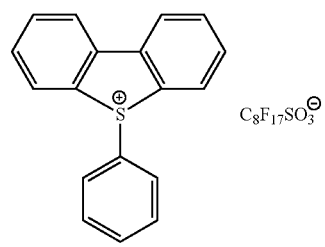
(PAG4-16) 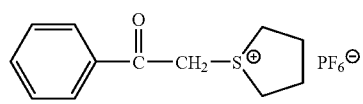
(PAG4-17) 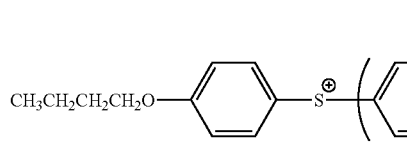
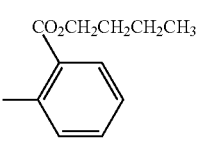
(PAG4-18) 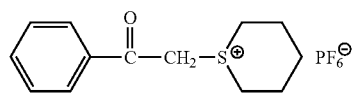
(PAG4-19) 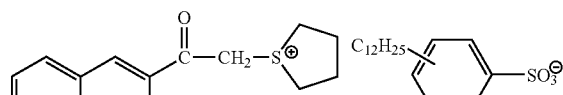
(PAG4-20) 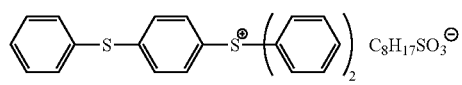
(PAG4-21) 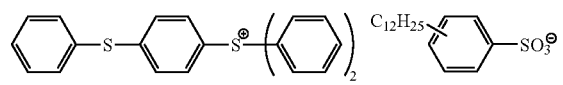
(PAG4-22) 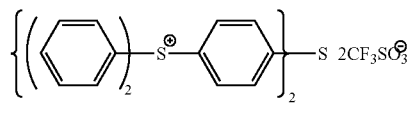
(PAG4-23) 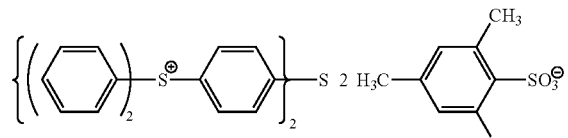
(PAG4-24) 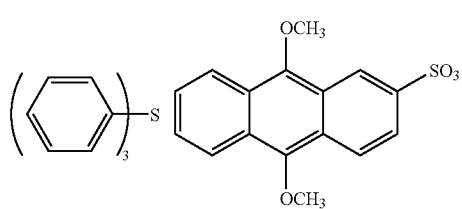
(PAG4-27) 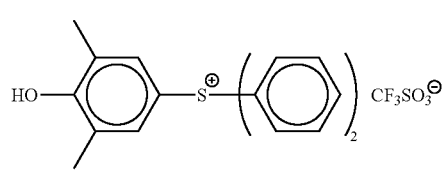

-continued
(PAG4-28) 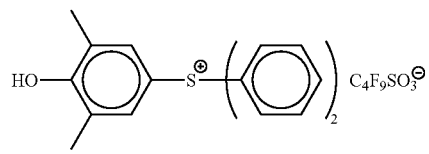
(PAG4-29) 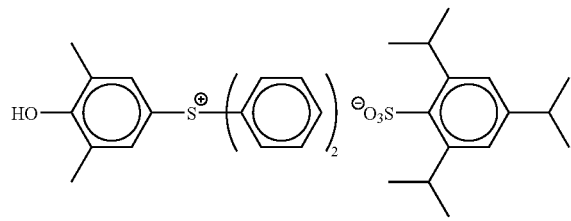
(PAG4-30) 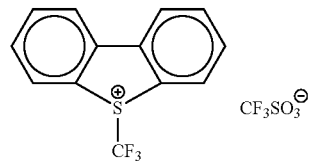
(PAG4-31) 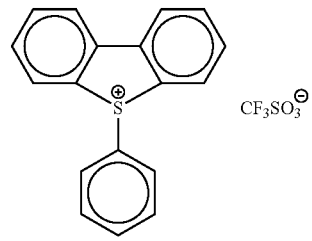
(PAG4-32) 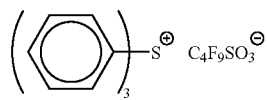
(PAG4-33) 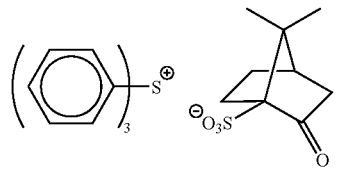
(PAG4-34) 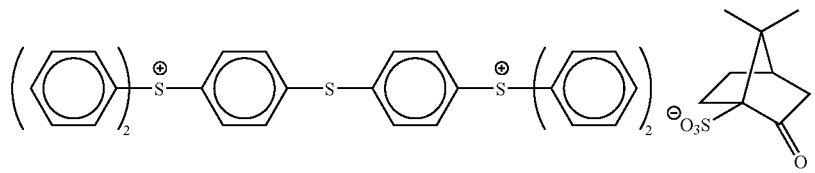
(PAG4-35) 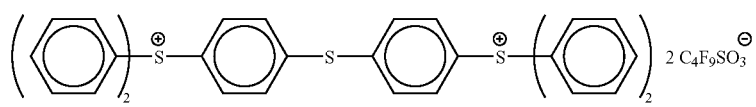
(PAG4-36) 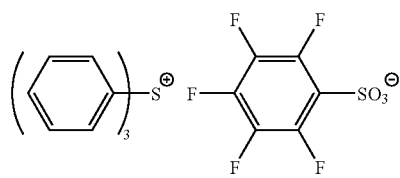
(PAG4-37) 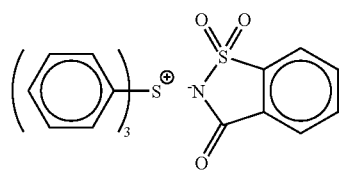
(PAG4-38) 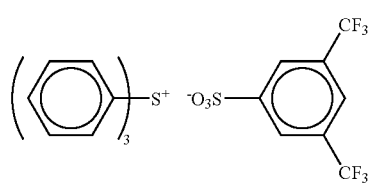

The onium salts represented by the foregoing formulae (PAG3) and (PAG4) are known compounds and can be synthesized using the methods as described in, e.g., U.S. Pat. Nos. 2,807,648 and 4,247,473, or JP-A-53-101331.

(3) Disulfone compounds represented by the following formula (PAG5) or iminosulfonate compounds represented by the following formula (PAG6):

$$Ar^3-SO_2-SO_2-Ar^4 \quad \text{(PAG5)}$$

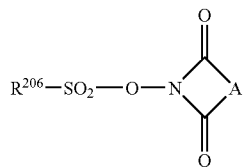
(PAG6)

In the above formulae, $Ar^3$ and $Ar^4$ independently represent a substituted or unsubstituted aryl group, $R^{206}$ represents a substituted or unsubstituted alkyl or aryl group, and A represents a substituted or unsubstituted alkylene, alkenylene or arylene group.

Examples of those compounds are illustrated below, but these examples should not be construed as limiting the scope of the disulfone or iminosulfonate compounds usable in the invention.

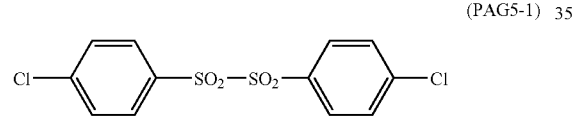
(PAG5-1)

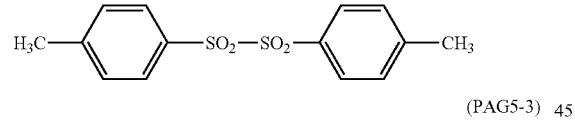
(PAG5-2)

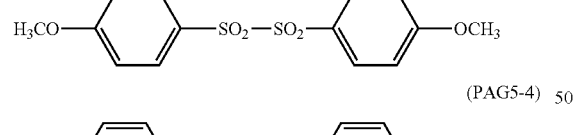
(PAG5-3)

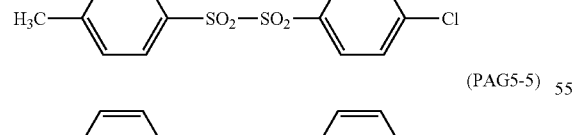
(PAG5-4)

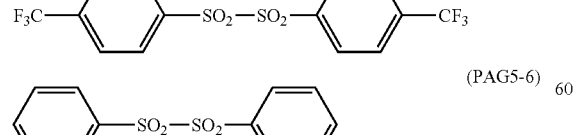
(PAG5-5)

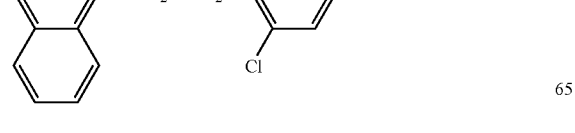
(PAG5-6)

-continued

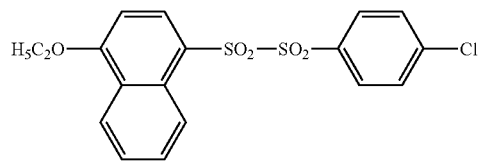
(PAG5-7)

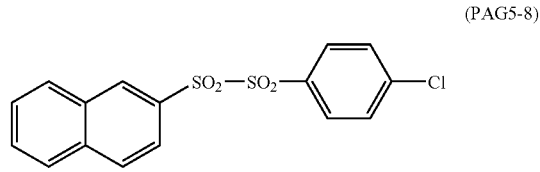
(PAG5-8)

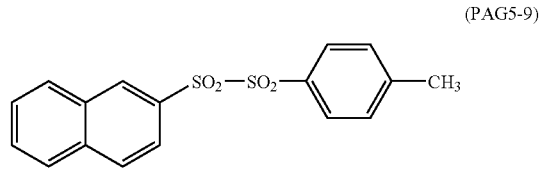
(PAG5-9)

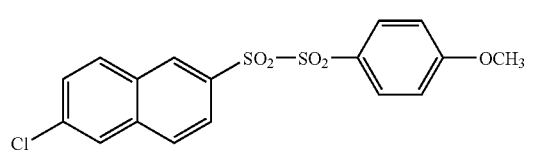
(PAG5-10)

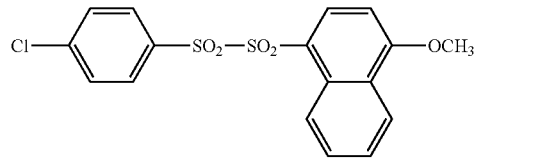
(PAG5-11)

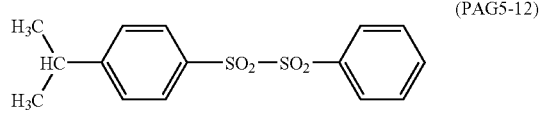
(PAG5-12)

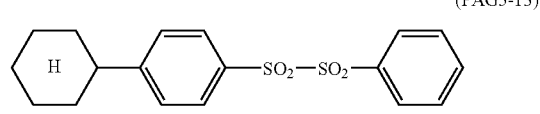
(PAG5-13)

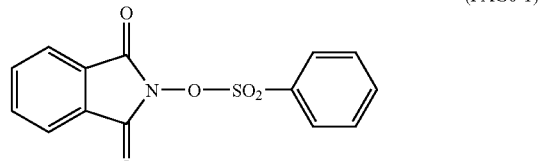
(PAG6-1)

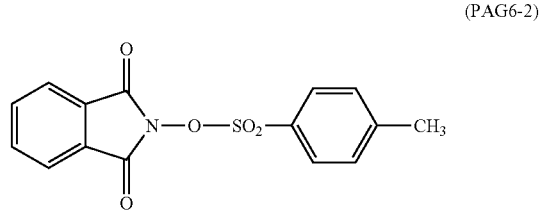
(PAG6-2)

(PAG6-3)
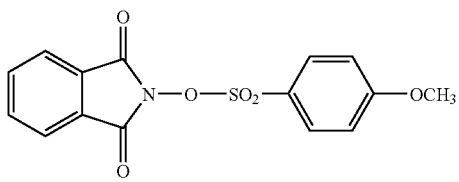

(PAG6-4)
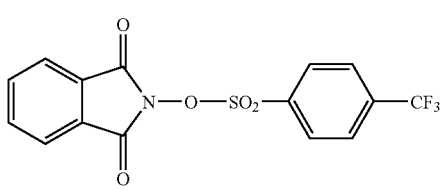

(PAG6-5)
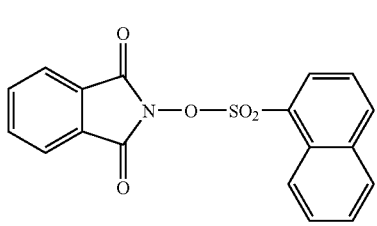

(PAG6-6)
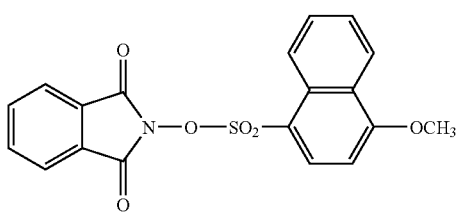

(PAG6-7)
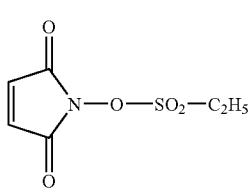

(PAG6-8)
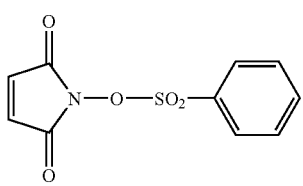

(PAG6-9)
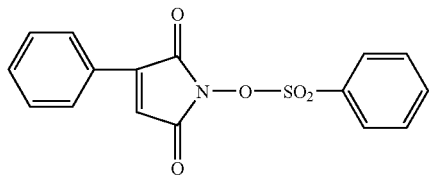

(PAG6-10)
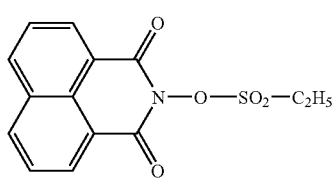

(PAG6-11)
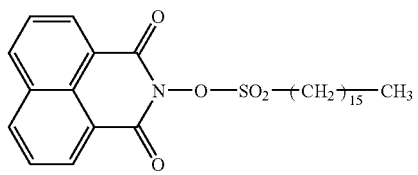

(PAG6-12)
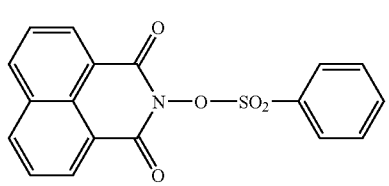

(PAG6-13)
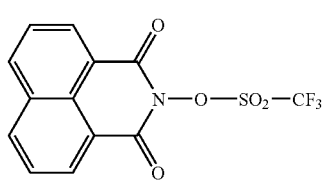

(4) Diazodisulfone compounds represented by the following formula (PAG7):

(PAG7)
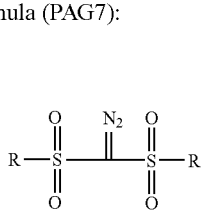

In the above formula, R represents a straight-chain, branched or cyclic alkyl group, or an unsubstituted or substituted aryl group.

Examples of such compounds are illustrated below, but these compounds should not be construed as limiting the scope of the diazodisulfone compounds usable in the invention.

(PAG7-1)
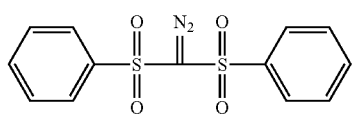

(PAG7-2)
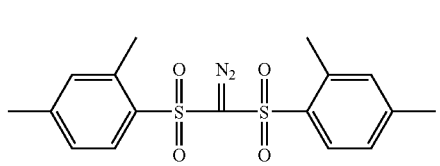

(PAG7-3)
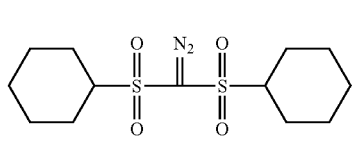

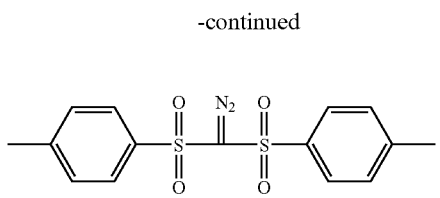 (PAG7-4)
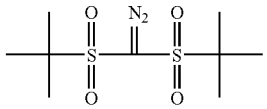 (PAG7-5)
Of the compounds illustrated above as photo-acid generators usable together with the compound(s) as Component (A), the following compounds are preferred in particular:
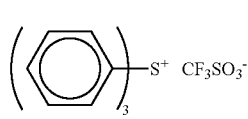 (z1)
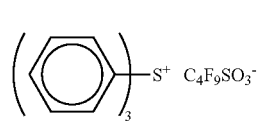 (z2)
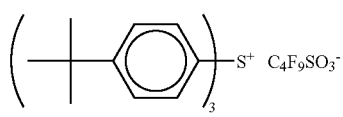 (z3)
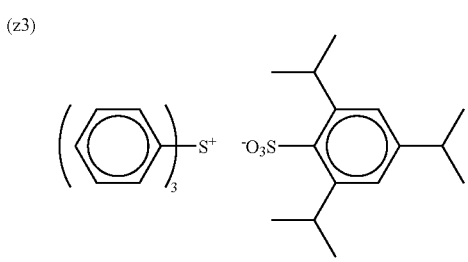 (z4)
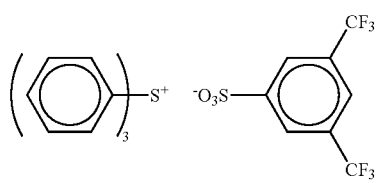 (z5)
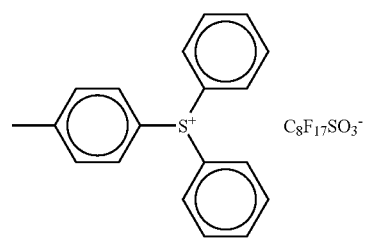 (z6)
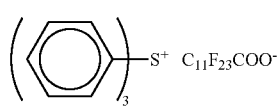 (z7)
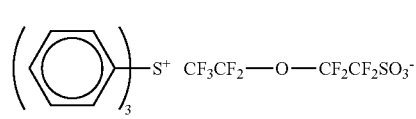 (z8)
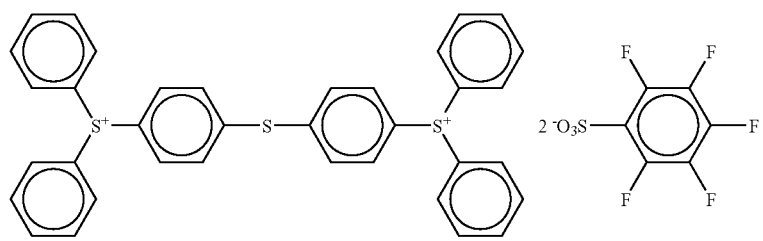 (z9)
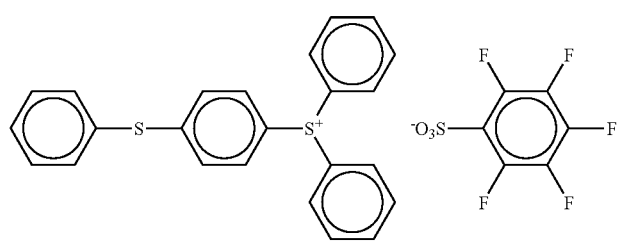 (z10)

-continued
(z11) 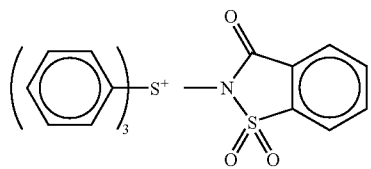
(z12) 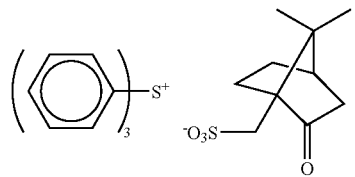
(z13) 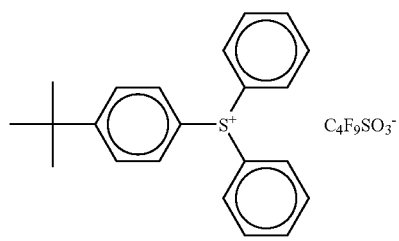
(z14) 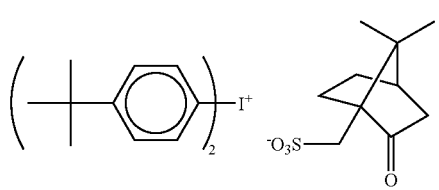
(z15) 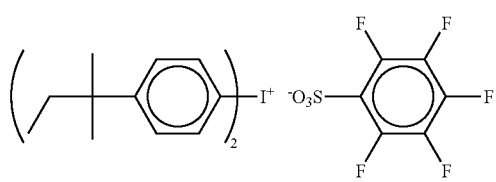
(z16) 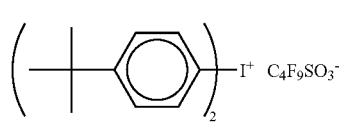
(z17) 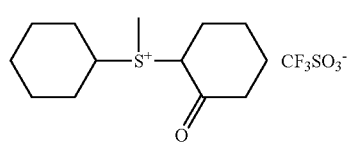
(z18) 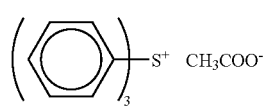
(z19) 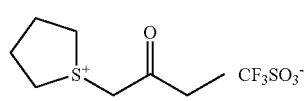
(z20) 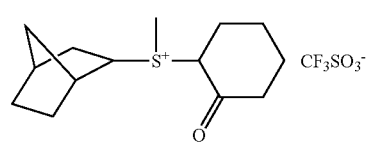
(z21) 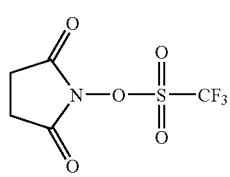
(z22) 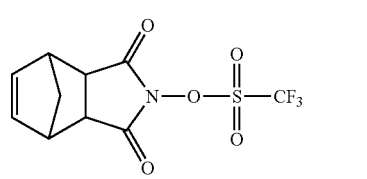
(z23) 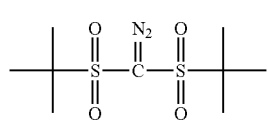
(z24) 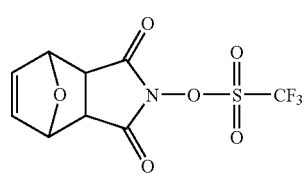
(z25) 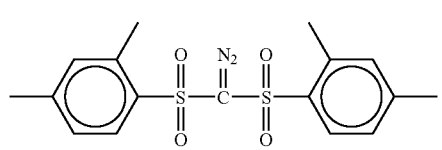
(z26) 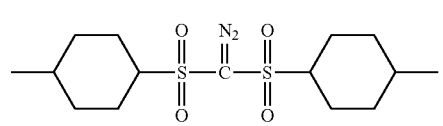
(z27) (z26)
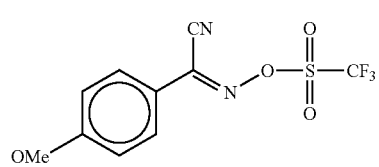

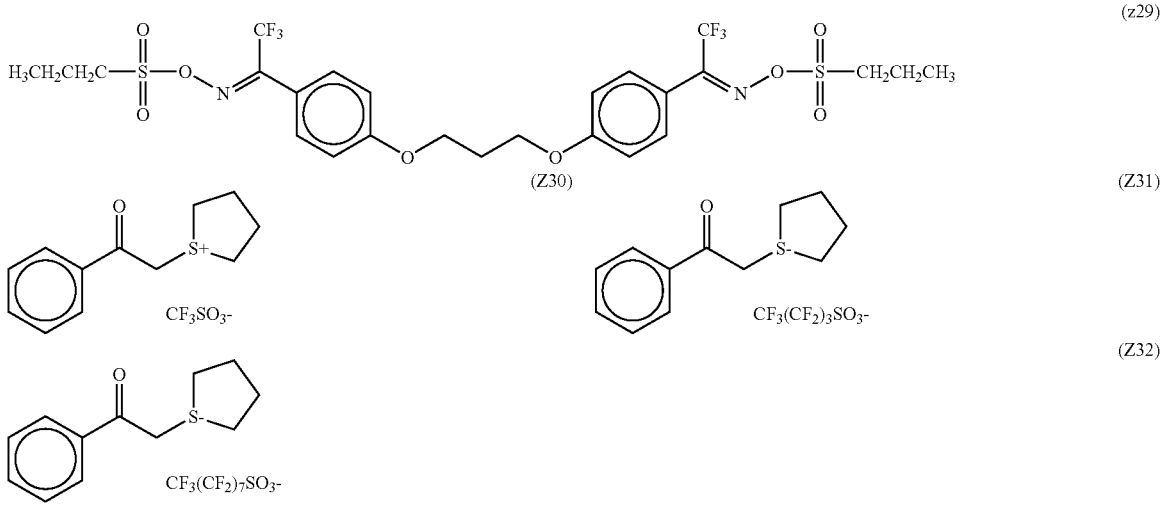

(z29)

(Z30)

(Z31)

(Z32)

Next the present compounds of formulae (I) to (III) are illustrated below in more detail.

[1-1] Present Iodonium Salt Compounds Represented by Formula (I)

Each of $R_{28}$ to $R_{37}$ groups in the foregoing formula (I) represents a hydrogen atom, a straight-chain or branched alkyl group having 1 to 4 carbon atoms, a cycloalkyl group having 3 to 8 carbon atoms, a alkoxy group having 1 to 4 carbon atoms, a hydroxyl group, a halogen atom, or an —S—$R_{38}$ group.

Herein, $R_{38}$ represents a straight-chain or branched alkyl group having 1 to 12 carbon atoms, a cycloalkyl group having 3 to 8 carbon atoms, or an aryl group having 6 to 14 carbon atoms.

Examples of a straight-chain or branched alkyl group having 1 to 4 carbon atoms, a cycloalkyl group having 3 to 8 carbon atoms, an alkoxy group having 1 to 4 carbon atoms as $R_{28}$ to $R_{37}$ each and examples of an aryl group as $R_{38}$ include the same ones as recited hereinbefore as examples of the corresponding groups respectively.

$X^-$ is an anion of sulfonic acid represented by the foregoing formula (X), preferably an anion of sulfonic acid represented by the foregoing formula (X').

In formula (X) or (X'), the alkyl groups as $R_{1a}$ to $R_{13a}$ groups include alkyl groups having 1 to 12 carbon atoms, such as methyl, ethyl, propyl, n-butyl, sec-butyl and t-butyl, which may have substituent groups.

The haloalkyl groups represented by $R_{1a}$ to $R_{13a}$ groups are alkyl groups substituted with a halogen atom, and include alkyl groups having 1 to 12 carbon atoms which are substituted with at least one of fluorine atom, chlorine atom, bromine atom and iodine atom, and the preferable haloalkyl groups are alkyl groups substituted with a fluorine atom.

The halogen atoms as $R_{1a}$ to $R_{13a}$ groups include fluorine, chlorine and iodine atoms.

As examples of substitutents the foregoing alkyl groups may have, mention may be made of alkoxy groups having 1 to 4 carbon atoms, halogenatoms (e.g., fluorine, chlorine, iodine), aryl groups having 6 to 10 carbon atoms, alkenyl groups having 2 to 6 carbon atoms, a cyano group, a hydroxyl group, a carboxyl group, alkoxycarbonyl groups and a nitro group.

Examples of a hetero atom-containing divalent linkage group as $A_1$, $A_2$ or A include —O—, —S—, —CO—, —COO—, —CONR—, —SO$_2$NR—, —CONRCO—, —SO$_2$NRCO—, —SO$_2$NRSO$_2$— and —OCONR—.

Herein, R represents a hydrogen atom, or a 1-10C alkyl group which may be substituted with a halogen atom, a hydroxyl group or an alkoxy group. Further, R may combine with at least one of the $R_{1a}$ to $R_{13a}$ groups to form a ring. And the ring formed may contain a linkage group, such as an oxygen atom, a nitrogen atom, a sulfur atom or —CO—.

As the sulfonic acids of formula (X) or (X'), cases are suitable where at least one of the $R_{1a}$ to $R_{13a}$ groups represents a halogen atom, especially a fluorine atom. In particular, it is preferable that either the $R_{12}$, or $R_{13a}$ group or both of these groups in formula (X) or (X') are fluorine atoms.

Of these sulfonic acids, $CF_3(CF_2)_k[A(CF_2)_{k'}]_qSO_3H$, $CF_3(CF_2)_k(CH_2)_{k'}SO_3H$, $CH_3(CH_2)_k(CF_2)_{k'}SO_3H$ (wherein k is an integer of 0 to 12, k' is an integer of 1 to 12, and A and q respectively have the same meanings as the above) and compounds represented by the following formula are preferred over the others, especially $CF_3CF_2$—O—$CF_2CF_2SO_3H$ is preferred:

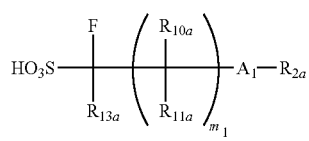

Herein, $m_1$ is an integer of 0 to 3, preferably 0 or 1, and $A_1$ preferably represents a single bond, —O—, —CONR— or —COO—.

Further, it is preferable that the number of fluorine atoms contained in the sulfonic acid of formula (X) be not more than 20, preferably not more than 15, particularly preferably not more than 9. Furthermore, in view of improvement in affinity of the acid generator for water, it is preferable that the number of fluorine atoms contained in the sulfonic acid is smaller than that of hydrogen atoms.

[1-2] Present Sulfonium Salt Compounds Represented by Formula (II)

Each of $R_1$ to $R_{15}$ groups in the foregoing formula (II) represents a hydrogen atom, a straight-chain or branched alkyl group having 1 to 4 carbon atoms, a cycloalkyl group having 3 to 8 carbon atoms, an alkoxy group having 1 to 4 carbon atoms, a hydroxyl group, a halogen atom, or an —S—$R_{38}$ group.

Herein, $R_{38}$ represents a straight-chain or branched alkyl group having 1 to 12 carbon atoms, a cycloalkyl group having 3 to 8 carbon atoms, or an aryl group having 6 to 14 carbon atoms.

Examples of a straight-chain or branched alkyl group having 1 to 4 carbon atoms, a cycloalkyl group having 3 to 8 carbon atoms, an alkoxy group having 1 to 4 carbon atoms as $R_1$ to $R_{15}$ each and examples of an aryl group as $R_{38}$ include the same ones as recited hereinbefore as examples of the corresponding groups respectively.

$X^-$ is an anion of sulfonic acid represented by the foregoing formula (X).

The anion of sulfonic acid represented by formula (X) conforms to the contents (including specific examples and suitable examples) explained about the iodonium salt compounds [1-1] of the foregoing formula (I).

[1-3] Present Sulfonium Salt Compounds Represented by Formula (III)

Each of $R_{16}$ to $R_{27}$ groups in the foregoing formula (III) represents a hydrogen atom, a straight-chain or branched alkyl group having 1 to 4 carbon atoms, a cycloalkyl group having 3 to 8 carbon atoms, an alkoxy group having 1 to 4 carbon atoms, a hydroxyl group, a halogen atom, or an —S—$R_{38}$ group.

Herein, $R_{38}$ represents a straight-chain or branched alkyl group having 1 to 12 carbon atoms, a cycloalkyl group having 3 to 8 carbon atoms, or an aryl group having 6 to 14 carbon atoms.

Examples of a straight-chain or branched alkyl group having 1 to 4 carbon atoms, a cycloalkyl group having 3 to 8 carbon atoms, an alkoxy group having 1 to 4 carbon atoms as $R_{16}$ to $R_{27}$ each and examples of an aryl group as $R_{38}$ include the same ones as recited hereinbefore as examples of the corresponding groups respectively.

$X^-$ is an anion of sulfonic acid represented by the foregoing formula (X).

The anion of sulfonic acid represented by formula (X) conforms to the contents (including specific examples and suitable examples) explained about the iodonium salt compounds [1-1] of the foregoing formula (I).

<<(B) Resin Capable of Increasing Solubility in Alkali Developer Under Action of Acid>>

In the invention, the resin (B) is an essential component of the first composition.

The resin (B) has groups that can be decomposed by the action of an acid (hereinafter referred to as "acid-decomposable groups" too). The acid-decomposable groups are contained in at least either main chain or side chains of the resin, preferably in side chains of the resin.

As examples of an acid-decomposable group, mention may be made of groups capable of forming at least one of a carboxylic acid and a phenolic hydroxy group by being decomposed by the action of an acid.

The resin (B) used in the invention is selected preferably depending on the kind of light for exposure or rays for irradiation. Specifically, it is preferable that the kind of resin (B) be selected in view of transparency and sensitivity to exposure light or irradiation beams, and further with consideration of dry etching resistance.

Examples of a resin (B) used suitably in a photosensitive composition to undergo exposure to KrF excimer laser or irradiation with electron beams or X-ray include resins containing acid-decomposable groups and aromatic rings (resins of polyhydroxystyrene type).

Examples of a resin (B) used preferably in a photosensitive composition to undergo exposure to ArF excimer laser include resins containing no aromatic rings but containing acid-decomposable groups and cycloaliphatic structures.

Now, resins included in the resin (B) used suitably in a photosensitive composition to undergo exposure to KrF excimer laser or irradiation with electron beams or X-ray are illustrated below in detail.

Groups preferred as an acid-decomposable group are a group represented by —COOA$^0$ and a group represented by —O—B$^0$. Groups containing these groups are represented by —R$^0$—COOA$^0$ and —Ar—O—B$^0$ respectively.

Therein, A$^0$ represents —C(R$^{01}$)(R$^{02}$)(R$^{03}$) —Si(R$^{01}$)(R$^{02}$)(R$^{03}$) or —C(R$^{04}$)(R$^{05}$)—O—R$^{06}$. B$^0$ represents A$^0$ or —CO—O-A$^0$. R$^0$, R$^{01}$ to R$^{06}$, and Ar have the same meanings as those described hereinafter respectively.

Suitable examples of an acid-decomposable group include a silyl ether group, a cumyl ester group, an acetal group, a tetrahydropyranyl ether group, an enol ether group, an enol ester group, a tertiary alkyl ether group, a tertiary alkyl ester group and a tertiary alkylcarbonate group. Of these groups, a tertiary alkyl ester group, a tertiary alkylcarbonate group, a cumyl ester group, an acetal group and a tetrahydropyranyl ether group are preferred over the others. In particular, an acetal group is well suited for use as the acid-decomposable group.

The acid-decomposable resin contains preferably a repeating unit having the acid-decomposable group in an amount of 5 to 70 mole %, more preferably 10 to 60 mole %, far more preferably 15 to 50 mole %, based on the total repeating units.

Examples of a parent resin to which the acid-decomposable groups as recited above are bonded as side chains include alkali-soluble resins containing —OH or —COOH groups, preferably —R$^0$—COOH or —Ar—OH groups, in their side chains. As examples of such resins, mention may be made of alkali-soluble resins illustrated below.

The suitable alkali dissolution rate of such an alkali-soluble resin is not slower than 170 angstrom/sec, preferably not slower than 330 angstrom/sec, as measured in 0.261 N tetramethylammonium hydroxide (TMAH) at 23° C.

From the viewpoint of attaining a rectangular profile, alkali-soluble resins having high transparency to far ultraviolet rays or excimer laser beams are used to advantage. Specifically, preferable alkali-soluble resins are those having their transmittances at 248 nm in the range of 20 to 90% when they are formed into 1 μm-thick films.

Examples of alkali-soluble resins preferred in particular from those viewpoints include poly(o-, m- or p-hydroxystyrene), copolymer of o-, m- and p-hydroxystyrenes, hydrogenated poly(hydroxystyrene), halogen or alkyl-substituted poly(hydroxystyrene), partially O-alkylated or O-acylated poly(hydroxystyrene), styrene/hydroxystyrene copolymer, α-methylstyrene/hydroxystyrene copolymer, and hydrogenated novolak resin.

Resins usable in the invention, which contain acid-decomposable groups, can be prepared by reacting alkali-soluble resins with precursors of acid-decomposable groups, or by copolymerizing alkali-soluble resin-forming monomers to which acid-decomposable groups are bonded and other monomers, as disclosed in European Patent 254853, JP-A-2-25850, JP-A-3-223860 and JP-A-4-251259.

Resins suitable as acid-decomposable resins in the invention are poly(hydroxystyrene)s whose phenolic hydroxyl groups are partially or totally protected by acid-decomposable groups. The acid-decomposable groups preferred herein are acetal groups. By protection with acetal groups, variations in performance with the lapse of time from irradiation till post-baking can be reduced. As the acetal groups, 1-alkoxyethyl acetal groups are suitable. And more suitable acetal groups are cycloaliphatic or aryl group-containing 1-alkoxyethyl acetal groups. By using these acetal groups, dry etching resistance is enhanced.

Examples of a resin containing acid-decomposable groups which can be used in the invention are recited below, but these examples should not be construed as limiting the scope of the invention.

p-t-Butoxystyrene/p-hydroxystyrene copolymer
p-(t-Butoxycarbonyloxy)styrene/p-hydroxystyrene copolymer
p-(t-Butoxycarbonylmethyloxy)styrene/p-hydroxystyrene copolymer
4-(t-Butoxycarbonylmethyloxy)-3-methylstyrene/4-hydroxy-3-methylstyrene copolymer
p-(t-Butoxycarbonylmethyloxy) styrene/p-hydroxystyrene (10% hydrogenated) copolymer
m-(t-Butoxycarbonylmethyloxy)styrene/m-hydroxystyrene copolymer
o-(t-Butoxycarbonylmethyloxy)styrene/o-hydroxystyrene copolymer
p-(Cumyloxycarbonylmethyloxy)styrene/p-hydroxystyrene copolymer
Cumyl methacrylate/methyl methacrylate copolymer
4-t-Butoxycarbonylstyrene/dimethyl maleate copolymer
Benzyl methacrylate/tetrahydropyranyl methacrylate copolymer
p-(t-Butoxycarbonylmethyloxy)styrene/p-hydroxystyrene/styrene copolymer
p-t-Butoxystyrene/p-hydroxystyrene/fumaronitrile copolymer
t-Butoxystyrene/hydroxyethyl methacrylate copolymer
Styrene/N-(4-hydroxyphenyl)maleimide/N-(4-t-butoxycarbonyl oxyphenyl)maleimide copolymer
p-Hydroxystyrene/t-butyl methacrylate copolymer
Styrene/p-hydroxystyrene/t-butyl methacrylate copolymer
p-Hydroxystyrene/t-butyl acrylate copolymer
Styrene/p-hydroxystyrene/t-butyl acrylate copolymer
p-(t-Butoxycarbonylmethyloxy) styrene/p-hydroxystyrene/N-me thylmaleimide copolymer
t-Butyl methacrylate/1-adamantylmethyl methacrylate copolymer
p-Hydroxystyrene/t-butyl acrylate/p-acetoxystyrene copolymer
p-Hydroxystyrene/t-butyl acrylate/p-(t-butoxycarbonyloxy) styrene copolymer
p-Hydroxystyrene/t-butyl acrylate/p-(t-butoxycarbonylmethyloxy)styrene copolymer In the invention, resins containing repeating structural units represented by the following formulae (IV) and (V) are preferred as resins having acid-decomposable groups (Component (B)). The photosensitive compositions using these resins can have high resolution and smaller variations in their performances during the period from irradiation till baking.

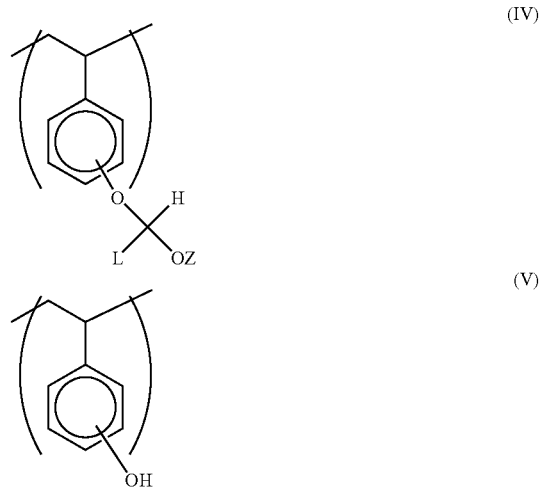

In the above formula (IV), L represents a hydrogen atom, an unsubstituted or substituted straight-chain, branched or cyclic alkyl group, or an unsubstituted or substituted aralkyl group.

Z represents an unsubstituted or substituted straight-chain, branched or cyclic alkyl group, or an unsubstituted or substituted aralkyl group. Further, Z may combine with L to form a 5- or 6-membered ring.

Examples of an alkyl group represented by L and Z each in formula (IV) include straight-chain, branched and cyclic alkyl groups having 1 to 20 carbon atoms, such as methyl, ethyl, propyl, isopropyl, n-butyl, isobutyl, t-butyl, pentyl, cyclopentyl, hexyl, cyclohexyl, octyl and dodecyl groups.

Examples of groups preferred as substitutents of those alkyl groups include an alkyl group, an alkoxy group, a hydroxyl group, a halogen atom, a nitro group, an acyl group, an acylamino group, a sulfonylamino group, an alkylthio group, an arylthio group and an aralkylthio group. As examples of a substituted alkyl group, mention may be made of a cyclohexylethyl group, an alkylcarbonyloxymethyl group, an alkylcarbonyloxyethyl group, an arylcarbonyloxyethyl group, an aralkylcarbonyloxyethyl group, an alkyloxymethyl group, an aryloxymethyl group, an aralkyloxymethyl group, an alkyloxyethyl group, an aryloxyethyl group, an aralkyloxyethyl group, an alkylthiomethyl group, an arylthiomethyl group, an aralkylthiomethyl group, an alkylthioethyl group, an arylthioethyl group and an aralkylthioethyl group. The alkyl moieties contained therein have no particular restrictions, but they may be any of straight-chain, cyclic and branched ones. For instance, the substituted alkyl group may be a cyclohexylcarbonyloxyethyl group, a t-butylcyclohexyl-carbonyloxyethyl or an n-butylcyclohexylcarbonyloxyethyl group. The aryl moieties contained in the above-recited ones have no particular restrictions, too. For instance, the substituted alkyl group may be a phenyloxyethyl group. Those aryl moieties may be further substituted, and cyclohexylphenyloxy ethyl group can be cited as an example of such a case. The aralkyl moieties also have no particular restrictions. For example, benzylcarbonyloxyethyl group may be such a substituted alkyl group.

As examples of an aralkyl group represented by L and Z each, mention may be made of those containing 7 to 15 carbon atoms, such as a substituted or unsubstituted benzyl group and a substituted or unsubstituted phenetyl groups. Examples of groups preferred as substitutents of aralkyl groups include an alkoxy group, a hydroxyl group, a halogen atom, a nitro group, an acyl group, an acylamino group, a sulfonylamino group, an alkylthio group, an arylthio group and an aralkylthio group. For instance, the substituted aralkyl group may be an alkoxybenzyl group, a hydroxybenzyl group or a phenylthiophenetyl group.

Further, it is preferable that Z is a substituted alkyl or aralkyl group, because improvement in edge roughness can be perceived in such a case. Examples of a substituent suitable for the alkyl group include a cyclic alkyl group, an aryloxy group, an alkylcarboxy group, an arylcarboxy group and an aralkylcarboxy group, and examples of a substituent suitable for the aralkyl group include an alkyl group, a cyclic alkyl group and a hydroxyl group.

As examples of a 5- or 6-membered ring formed by combining L and Z, mention may be made of a tetrahydropyran ring and a tetrahydrofuran ring.

The suitable ratio of the repeating structural units represented by formula (IV) to the repeating structural units represented by formula (V) in the resin is from 1/99 to 60/40, preferably from 5/95 to 50/50, particularly preferably from 10/90 to 40/60.

In the resin comprising the repeating structural units represented by formulae (IV) and (V), repeating structural units derived from other monomers may further be contained.

Examples of the other monomers include hydrogenated hydroxystyrene; halogen-, alkoxy- or alkyl-substituted hydroxystyrenes; styrene; halogen-, alkoxy-, acyloxy- or alkyl-substituted styrenes; maleic anhydride; acrylic acid derivatives; methacrylic acid derivatives; and N-substituted maleimides, but these examples should not be construed as limiting the scope of the invention.

The suitable molar ratio of the total structural units of formulae (IV) and (V) to the structural units derived from other monomers, or [(IV)+(V)]/[other monomers] ratio, is from 100/0 to 50/50, preferably from 100/0 to 60/40, particularly preferably 100/0 to 70/30.

Examples of a resin comprising the repeating structural units represented by formulae (IV) and (V) and other resins usable in the invention are illustrated below.

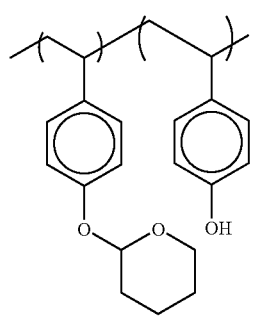

(A-1)

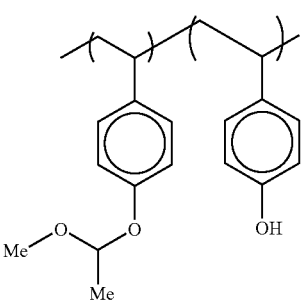

(A-2)

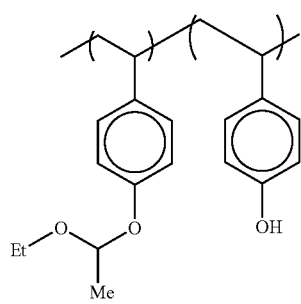

(A-3)

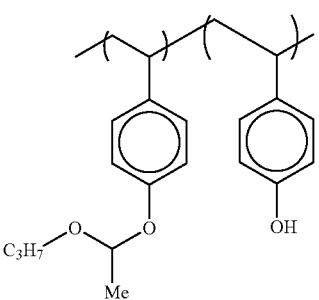

(A-4)

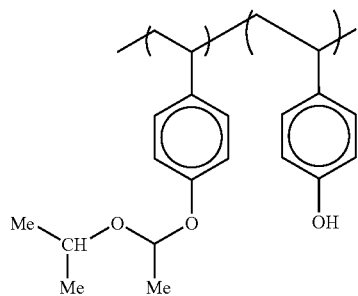

(A-5)

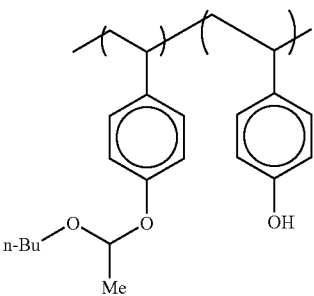

(A-6)

-continued
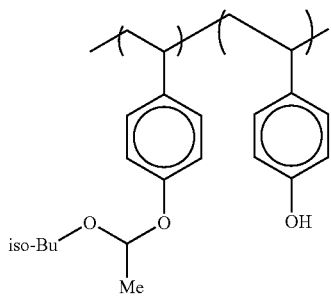 (A-7)
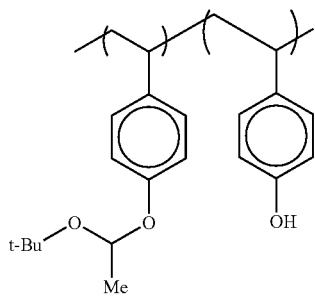 (A-8)
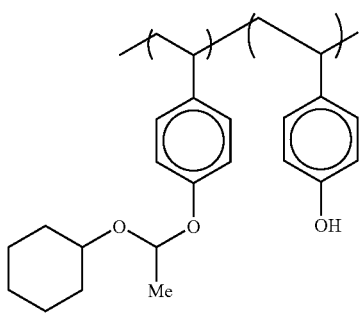 (A-9)
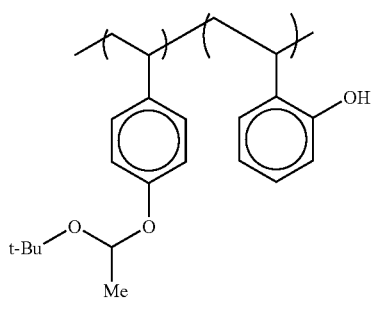 (A-10)
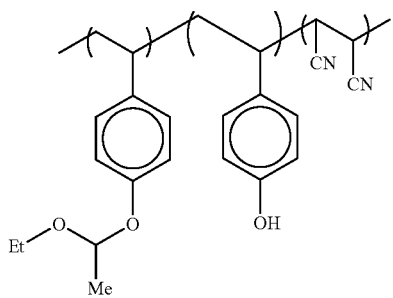 (A-11)
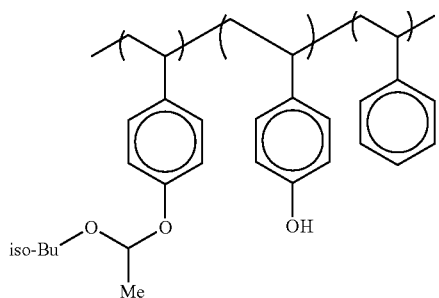 (A-12)
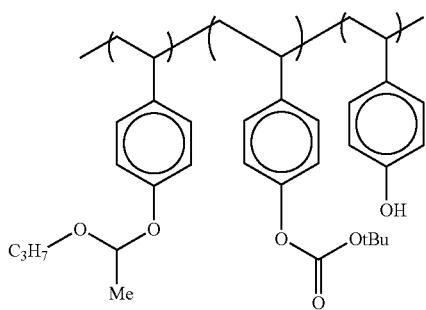 (A-13)
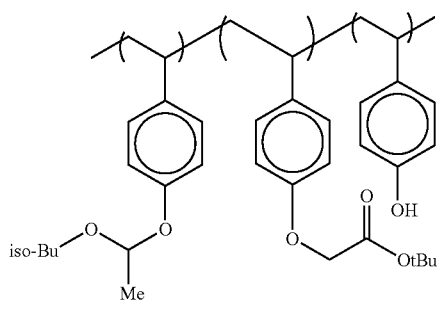 (A-14)

-continued
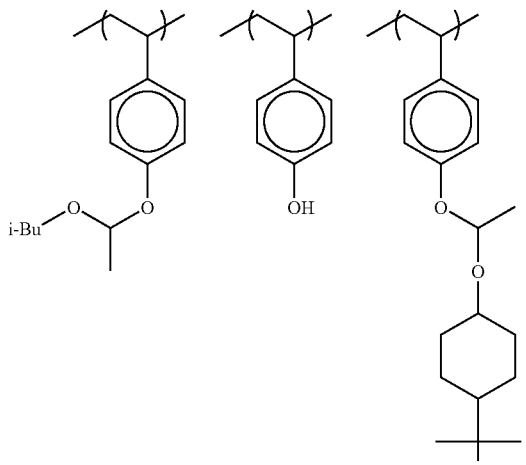
(A-15)
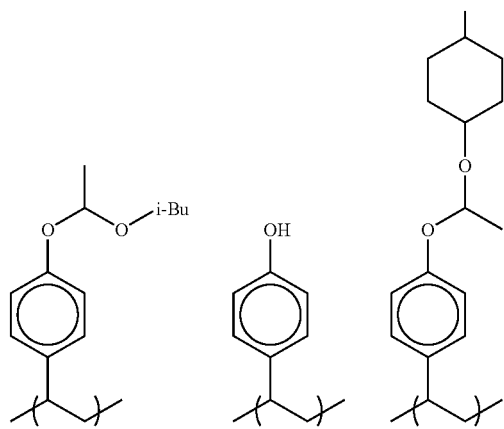
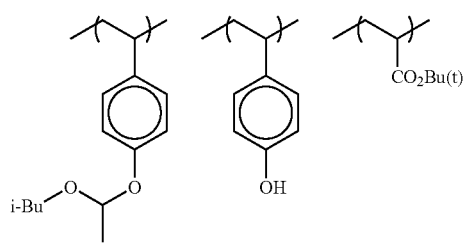
(A-16)
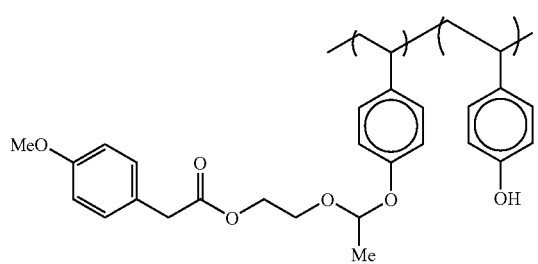
(A-18)
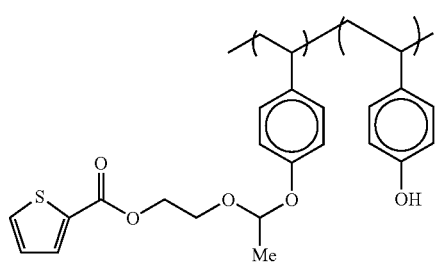
(A-19)

-continued
(A-20) 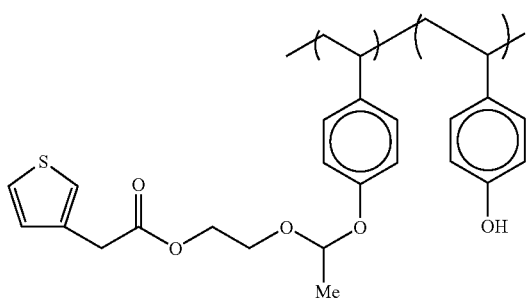
(A-21) 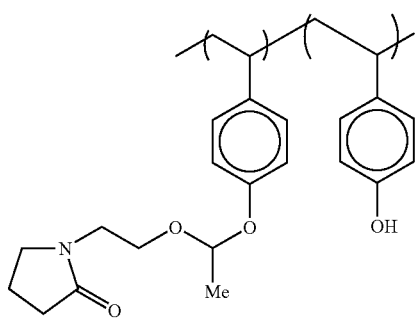
(A-22) 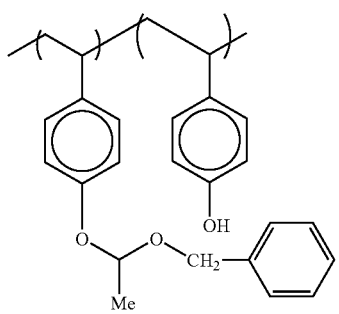
(A-23) 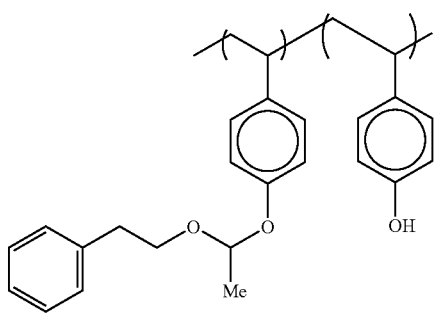
(A-24) 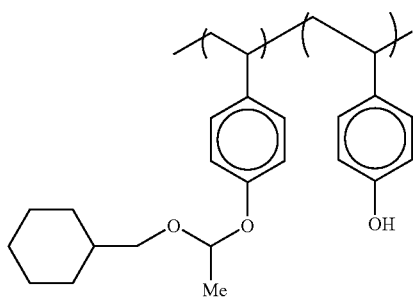
(A-25) 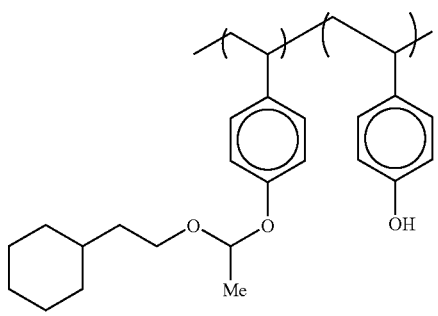
(A-26) 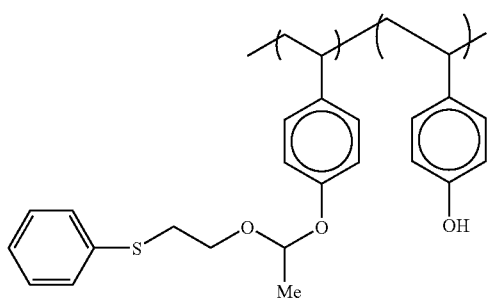
(A-27) 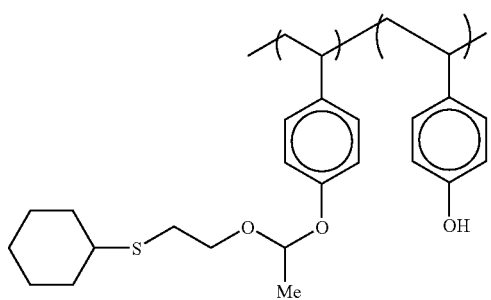

-continued
(A-28) 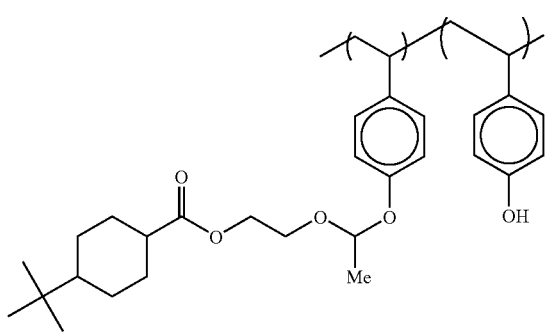
(A-29) 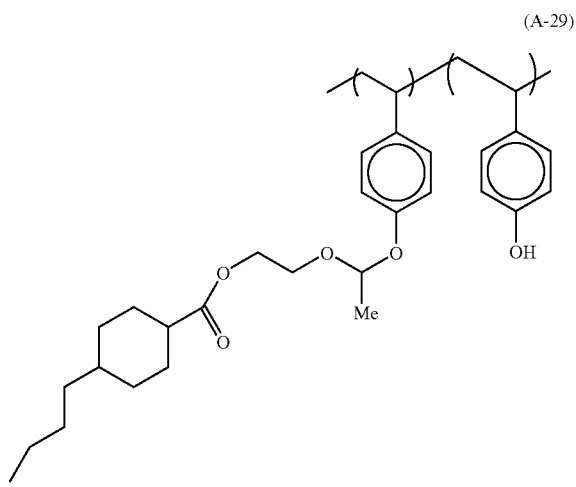
(A-30) 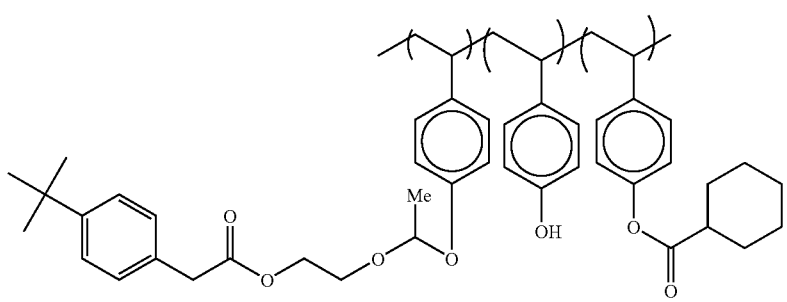
(A-31) (A-32)
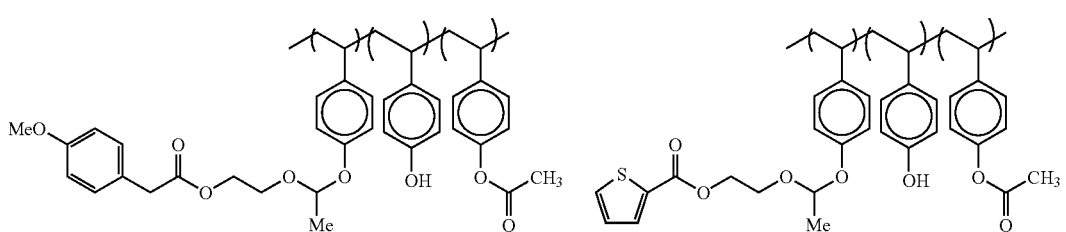
(A-33) (A-34)
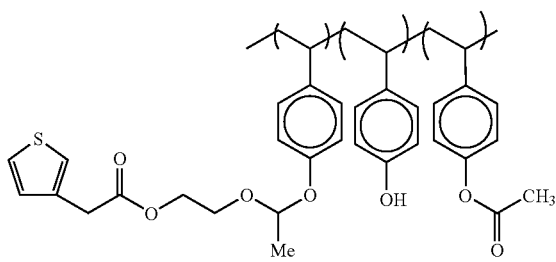

-continued
(A-35)
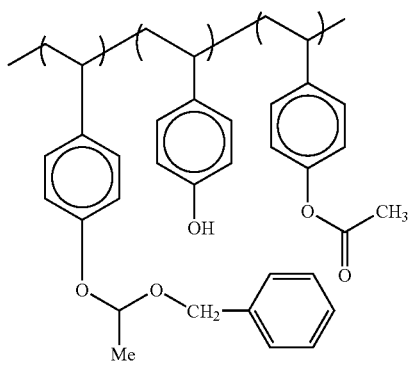
(A-36)
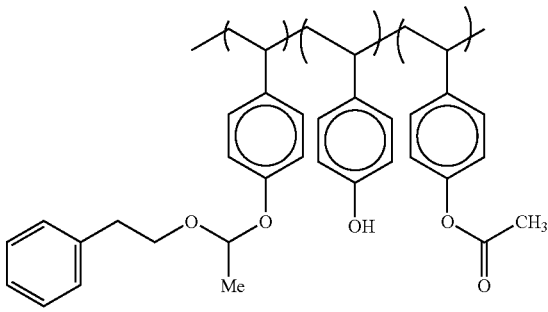
(A-37)
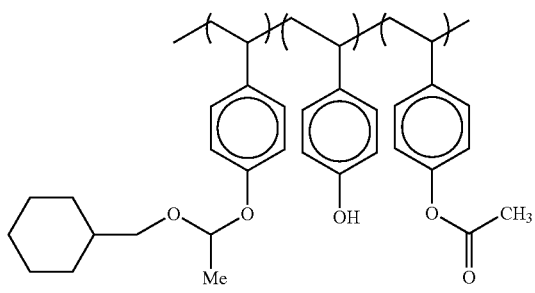
(A-38)
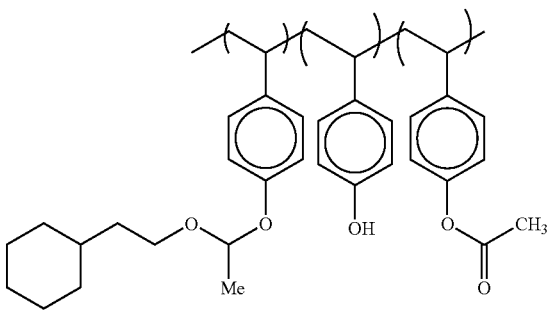
(A-39)
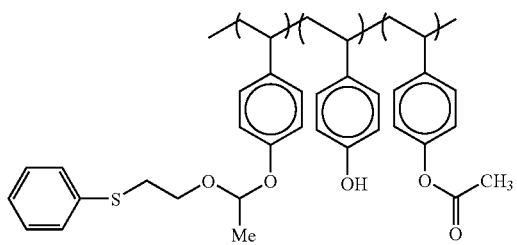
(A-40)
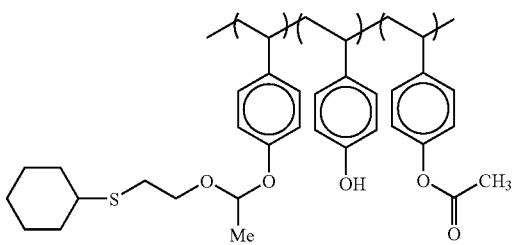
(A-41)
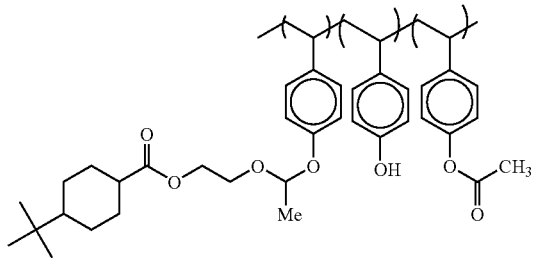
(A-42)
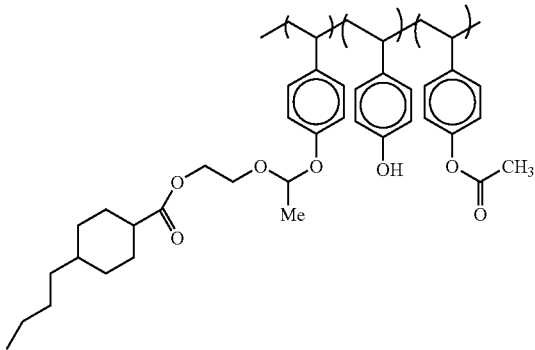

-continued
(A-43)
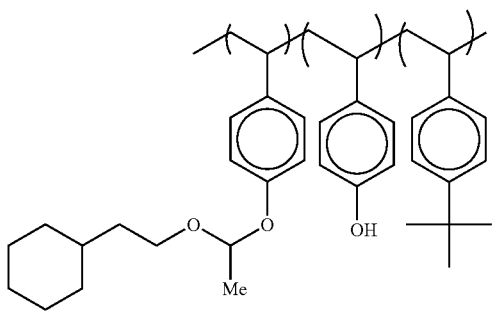
(A-44)
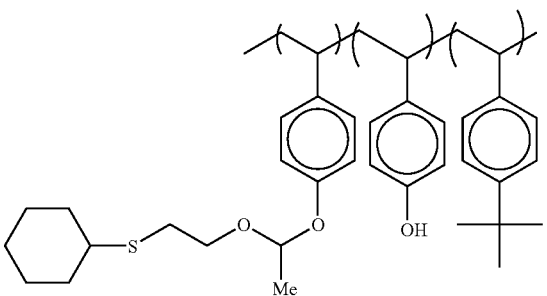
(A-45)
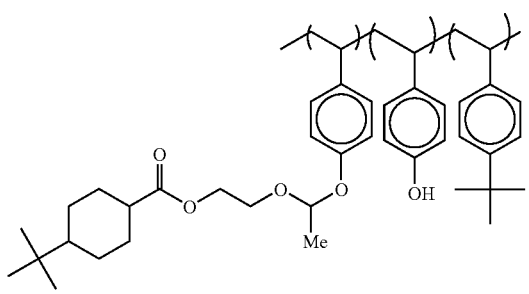
(A-46)
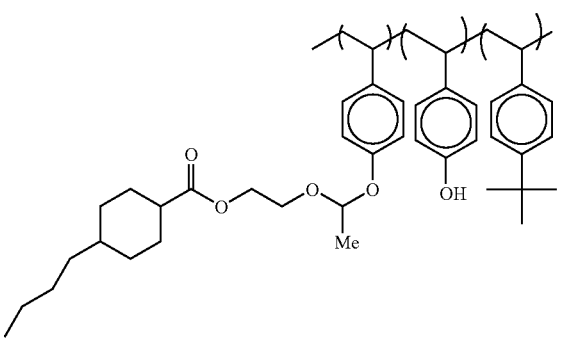
(A-47)
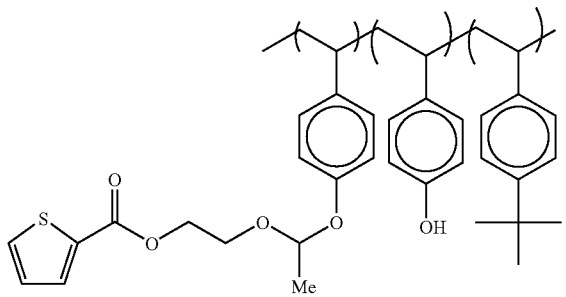
(A-48)
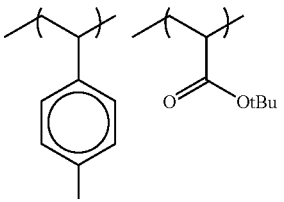
(A-49)
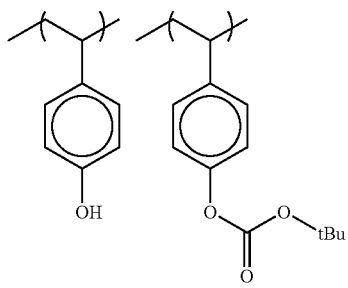
(A-50)
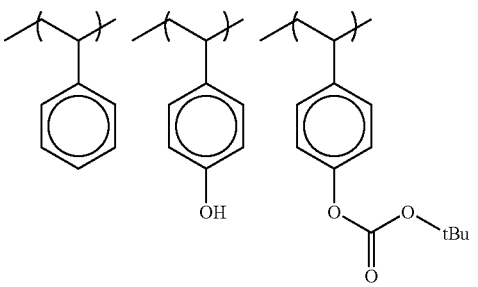
(A-51)
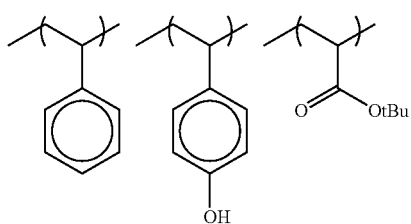

In the above structural formulae, Me stands for a methyl group, Et stands for an ethyl group, nBu stands for a n-butyl group, iso-Bu stands for an iso-butyl group, and tBu stands for a t-butyl group.

In the case of using acetal groups as the acid-decomposable groups, cross-link regions linked by polyfunctional acetal groups may be introduced in the polymer main chain by adding a polyhydroxy compound at the stage of synthesis for the purpose of controlling alkali-dissolution speed and enhancing heat resistance. The amount of polyhydroxy compound added is from 0.01 to 5 mole %, preferably from 0.05 to 4 mole %, based on the content of hydroxyl groups in the resin. As examples of a polyhydroxy compound, mention may be made of compounds having 2 to 6 phenolic or alcoholic hydroxyl groups per molecule, preferably compounds having 2 to 4 hydroxyl groups per molecule, particularly preferably compounds having 2 or 3 hydroxyl groups per molecule. More specifically, the following polyhydroxy compounds can be recited, but the invention should not be construed as being limited to these compounds.

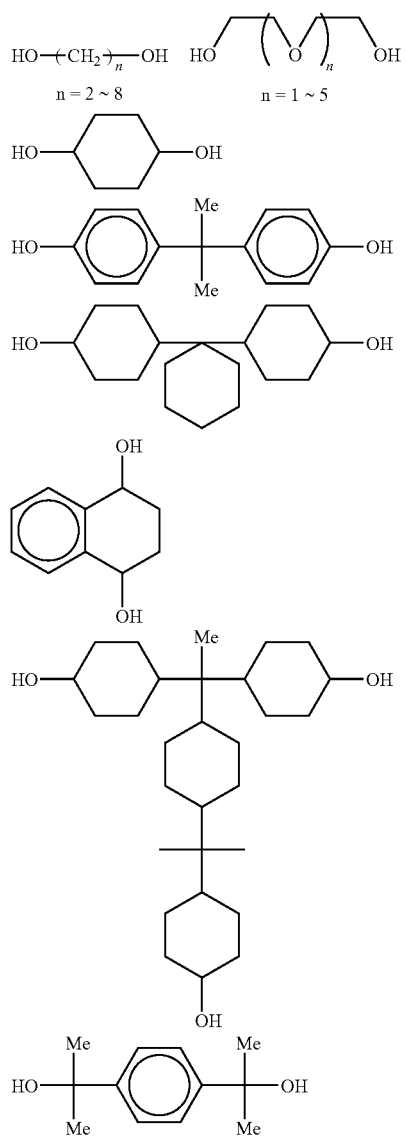

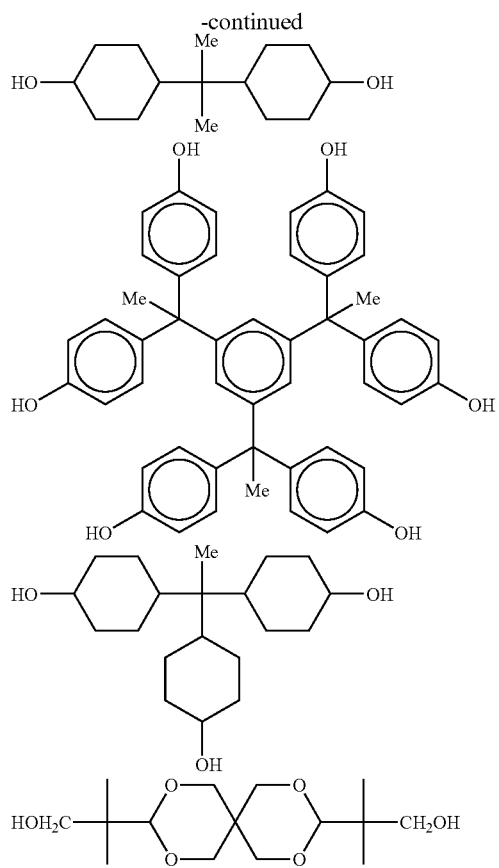

The suitable weight average molecular weight (Mw) of the resin (B) having acid-decomposable groups is from 2,000 to 300,000. When the resin has a weight average molecular weight less than 2,000, the thickness reduction caused in the unexposed areas of the resulting resist film by development becomes great; while when the weight average molecular weight of the resin is greater than 300,000 the resin itself becomes slow in alkali-dissolution speed and causes reduction in sensitivity. Herein, the term "weight average molecular weight" is defined as the value measured by gel permeation chromatography (GPC) and calculated in terms of polystyrene.

Secondly, resins as Component (B) which can be used to advantage in photosensitive compositions suitable for exposure to ArF excimer laser are illustrated in greater detail.

Suitable examples of acid-decomposable groups contained in such resins include groups represented by the following formulae (x) and (y) respectively, acid-decomposable groups having lactone structures, and acid-decomposable groups having cycloaliphatic structures. By having these acid-decomposable groups, the resins can have excellent storage stability.

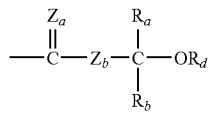
(y)

In the above formulae, Ra, Rb and Rc are independent of each other and each represents a hydrogen atom, or an unsubstituted or substituted alkyl, cycloalkyl or alkenyl group. In the formula (x), however, at least one of the Ra, Rb and Rc groups represents a group other than hydrogen. Rd represents an unsubstituted or substituted alkyl, cyclalkyl or alkenyl group. On the other hand, any two of the Ra, Rb and Rc groups in formula (x), or any two of the Ra, Rb and Rd groups may combine with each other to form a ring structure containing 3 to 8 carbon atoms. Further, the ring structure formed may contain a hetero atom. Examples of such a ring structure include cyclopropyl, cyclopentyl, cyclohexyl, cycloheptyl, 1-cyclohexenyl, 2-tetrahydrofuranyl and 2-tetrahydropyranyl groups.

Za and Zb are independently of each other, and each represents an oxygen atom or a sulfur atom.

Suitable examples of an alkyl group as Ra to Rd each include unsubstituted or substituted alkyl groups having 1 to 8 carbon atoms, such as methyl, ethyl, propyl, n-butyl, sec-butyl, hexyl, 2-ethylhexyl and octyl groups. Suitable examples of a cycloalkyl group as Ra to Rd each include unsubstituted or substituted cycloalkyl groups having 3 to 8 carbon atoms, such as cyclopropyl, cyclopentyl and cyclohexyl groups. Suitable examples of an alkenyl group as Ra to Rd each include unsubstituted or substituted alkenyl groups having 2 to 6 carbon atoms, such as vinyl, propenyl, allyl, butenyl, pentenyl, hexenyl and cyclohexenyl groups.

As suitable examples of substituents which the groups as recited above can have, mention may be made of a hydroxyl group, a halogen atom (e.g., fluorine, chlorine, bromine, iodine), a nitro group, a cyano group, an amido group, a sulfonamido group, an alkyl group (e.g., methyl, ethyl, propyl, n-butyl, sec-butyl, hexyl, 2-ethylhexyl, octyl), an alkoxy group (e.g., methoxy, ethoxy, hydroxyethoxy, propoxy, hydroxypropoxy, butoxy), an alkoxycarbonyl group (e.g., methoxycarbonyl, ethoxycarbonyl), an acyl group (e.g., formyl, acetyl, benzoyl), an acyloxy group (e.g., acetoxy, butylyloxy), and a carboxyl group.

Examples of repeating structural units having acid-decomposable groups as recited above are illustrated below, but these examples should not be construed as limiting the scope of the invention.

(c1)
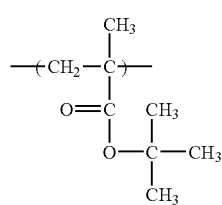

(c2)
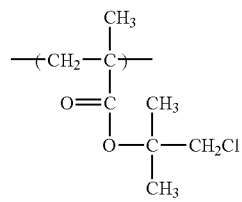

(c3)
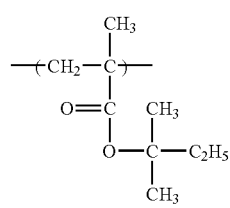

(c4)
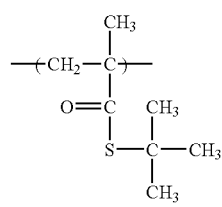

(c5)
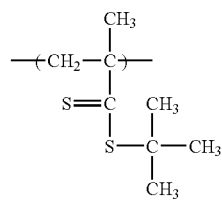

(c6)
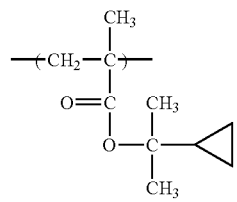

(c7)
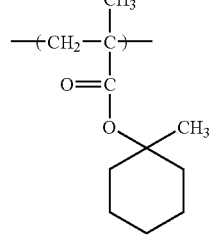

(c8)
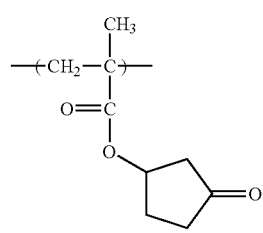

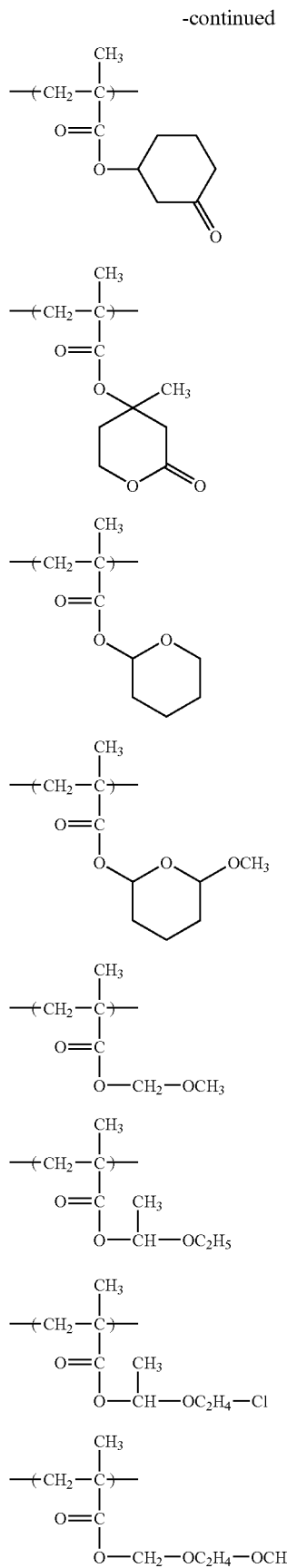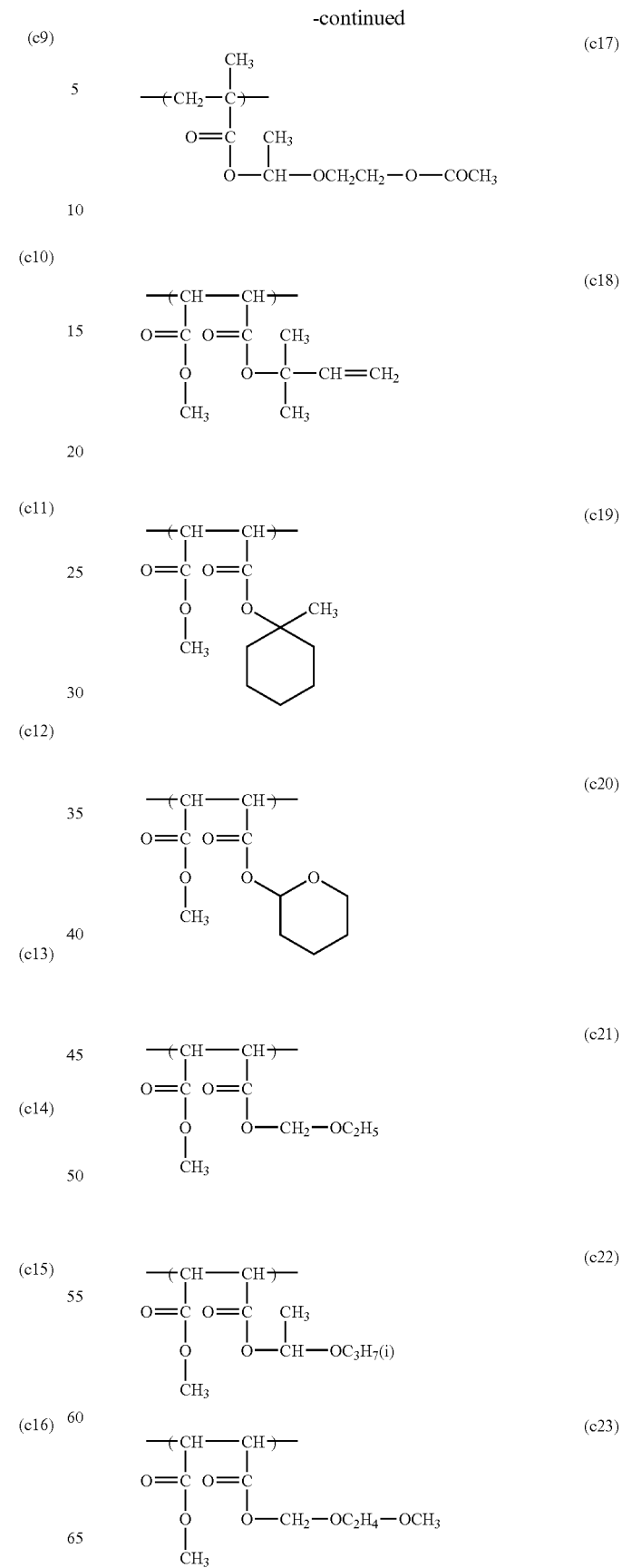

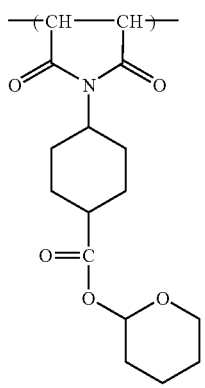

(c24)

Of the above-illustrated ones, the units (c1), (c7) and (C11) are preferred over the others because they are superior in acid-decomposability in particular.

In the invention, it is preferable that the acid-decomposable resins have lactone structures.

Herein, it is preferable that the lactone structures are present in the side chains of each resin. Specifically, the following repeating units (a1) to (a20) having lactone structures in side chains thereof can be recited.

As mentioned above, both cycloaliphatic and lactone structures may be provided with acid-decomposable groups, or may not necessarily be provided therewith.

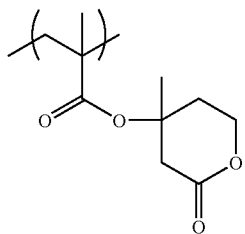

(a1)

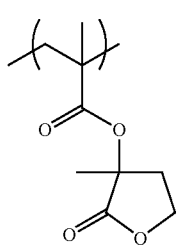

(a2)

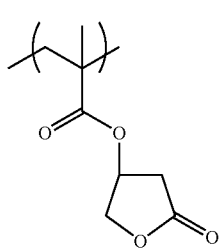

(a3)

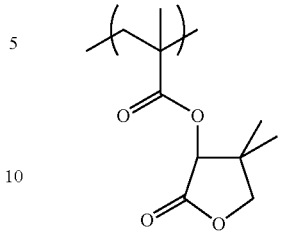

(a4)

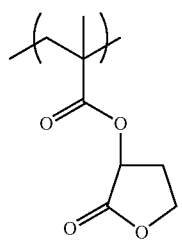

(a5)

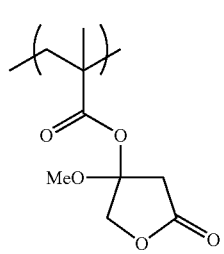

(a6)

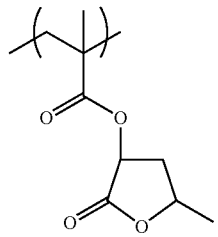

(a7)

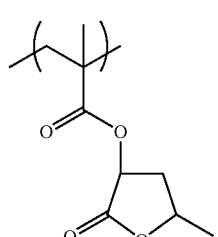

(a8)

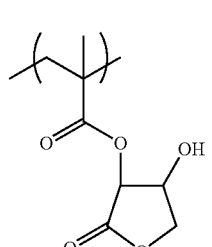

(a9)

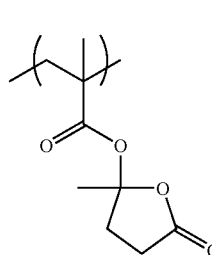

-continued (a10) 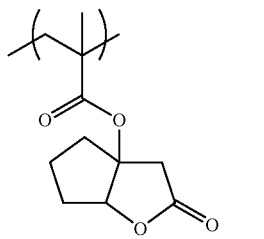

(a11) 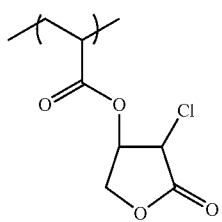

(a12) 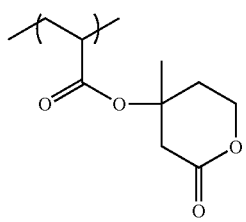

(a13) 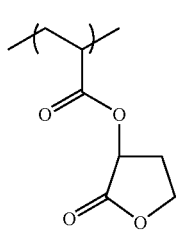

(a14) 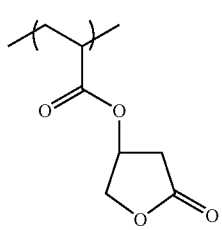

(a15) 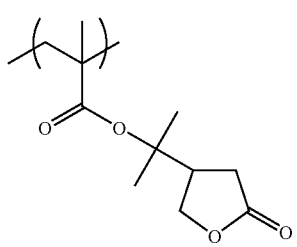

(a16) 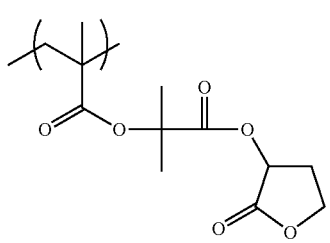

-continued (a17) 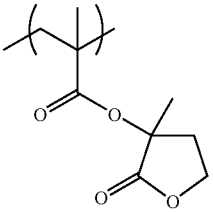

(a18) 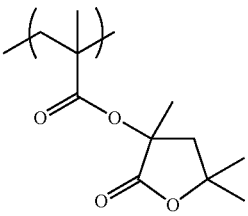

(a19) 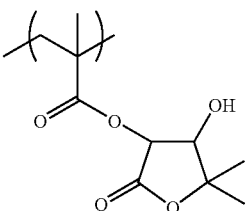

(a20) 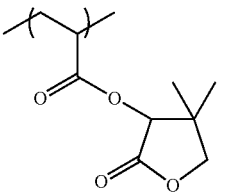

Of the structural units illustrated above, the units (a1), (a12) and (a15) are preferred over the others, because they generally show acid-decomposability.

As examples of a monocyclic cycloaliphatic structure which can be contained in acid-decomposable resins, mention may be made of groups having monocyclic cycloaliphatic skeletons containing at least 3 carbon atoms, preferably 3 to 8 carbon atoms, such as cyclopropane, cyclobutane, cyclopentane and cyclohexane skeletons. As examples of a polycyclic cycloaliphatic structure which can be contained in acid-decomposable resins, mention may be made of groups having polycyclic cycloaliphatic skeletons containing at least 5 carbon atoms, preferably 7 to 25 carbon atoms, such as bicyclo-, tricyclo- and tetracycloaliphatic skeletons. More specifically, structures as recited hereinafter are included in those structures.

On the other hand, the acid-decomposable group which may contain a cycloaliphatic group may be a group containing an acid-decomposable structure as a linkage and capable of being decomposed by the action of an acid to release a cycloaliphatic group, or a group wherein a group represented by the foregoing formula (x) or (y) is combined with an cycloaliphatic group directly or via a linkage group.

When monocyclic or polycyclic cycloaliphatic groups are contained in side chains of a resin, it is preferable that they be linked to the main chain of the resin via tertiary ester groups.

Suitable examples of a repeating unit having such a monocyclic or polycyclic cycloaliphatic structure as mentioned above include structural units represented by the following formulae (XII) to (XV):

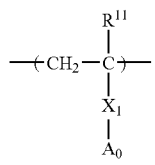
(XII)

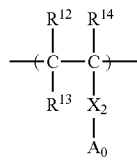
(XIII)

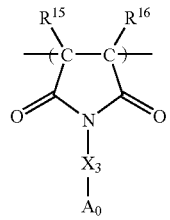
(XIV)

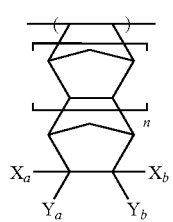
(XV)

The formulae (XII) to (XIV) are explained first, and an explanation of the formula (XV) follows them.

In formulae (XII) to (XIV), each of the substituent groups attached to the main chain of each repeating unit, namely $R^{11}$, $R^{12}$ and $R^{14}$ to $R^{16}$, represents a hydrogen atom, a halogen atom, a cyano group, an alkyl group or a haloalkyl group. These substituent groups may be the same as or different from each other.

Examples of an alkyl group represented by $R^{11}$, $R^{12}$ and $R^{14}$ to $R^{16}$ each include hydrocarbon groups having 1 to 4 carbon atoms, such as methyl, ethyl, propyl, n-butyl and sec-butyl groups.

As examples of a haloalkyl group represented by $R^{11}$, $R^{12}$ and $R^{14}$ to $R^{16}$ each, mention may be made of alkyl groups having 1 to 4 carbon atoms, whose hydrogen atoms are replaced partially or totally by halogen atoms. Herein, it is preferable for the halogen atoms to include fluorine, chlorine and bromine atoms. More specifically, the haloalkyl group includes fluoromethyl group, chloromethyl group, bromomethyl group, fluoroethyl group, chloroethyl group and bromoethyl group.

These alkyl and haloalkyl groups may further have substituents other than halogen atoms.

The substituent group $R^{13}$ represents a cyano group, $-CO-OR^{23}$ or $-CO-NR^{24}R^{25}$.

Herein, $R^{23}$ represents a hydrogen atom, an alkyl group, a cycloalkyl group, alkenyl group, or an acid-decomposable group. Examples of an acid-decomposable group include the same ones as recited above. For instance, the compounds having the same repeating structural units as described above are preferred. The alkyl, cycloalkyl or alkenyl group represented by $R^{23}$ may further have a substituent.

$R^{24}$ and $R^{25}$ each represent a hydrogen atom, an alkyl group, a cycloalkyl group or an alkenyl group. Herein, the alkyl, cycloalkyl and alkenyl groups each may further have a substituent. $R^{24}$ and $R^{25}$ may be the same or different. They may combine with each other to form a ring together with the nitrogen atom. The ring structure preferably formed in this case includes 5- to 8-membered rings, such as pyrrolidine, piperidine and piperazine skeletons.

As the alkyl group represented by $R^{23}$ to $R^{25}$ each, alkyl groups having 1 to 8 carbon atoms are suitable, with examples including methyl, ethyl, propyl, n-butyl, sec-butyl, hexyl, 2-ethylhexyl and octyl groups. As the cycloalkyl group, cycloalkyl groups having 3 to 8 carbon atoms are suitable, with examples including cyclopropyl, cyclopentyl and cyclohexyl groups. As the alkenyl group, alkenyl groups having 2 to 6 carbon atoms are suitable, with examples including vinyl, propenyl, allyl, butenyl, pentenyl, hexenyl and cyclohexenyl groups. These alkyl, cycloalkyl and alkenyl groups each may further have a substituent.

In formulae (XII) to (XIV), $X_1$, $X_2$ and $X_3$ in the substituent groups formed into $X_1$-$A_0$, $X_2$-$A_0$ and $X_3$-$A_0$ respectively are each a single bond or a divalent group. Examples of such a divalent group include an alkylene group, an alkenylene group, a cycloalkylene group, $-O-$, $-SO_2-$, $-O-CO-R^{26}-$, $-CO-O-R^{27}-$, and $-CO-NR^{28}-R^{29}-$. $X_1$, $X_2$ and $X_3$ may be the same as or different from each other.

Of the groups represented by $X_1$ to $X_3$ each, the alkylene group, the alkenylene group and the cycloalkylene group include divalent groups having the same carbon skeletons as the alkyl group, the alkenyl group and the cycloalkyl group that each of $R^{11}$, $R^{12}$ and $R^{14}$ to $R^{16}$ groups can represent, respectively.

$R^{26}$, $R^{27}$ and $R^{29}$ in $-OCO-R^{26}-$, $-CO-O-R^{27}-$ and $-CO-NR^{28}-R^{29}-$, which $X_1$ to $X_3$ each can represent, are each a single bond or a divalent group. Examples of such a divalent group include an alkylene group, an alkenylene group and a cycloalkylene group. Herein also, the alkylene group, the alkenylene group and the cycloalkylene group include divalent groups having the same carbon skeletons as the alkyl group, the alkenyl group and the cycloalkyl group that each of $R^{11}$, $R^{12}$ and $R^{14}$ to $R^{16}$ groups can represent, respectively. By further combining with an ether group, an ester group, an amido group, an urethane group or an ureido group, each of those groups may form a divalent group in its entirety. $R^{26}$, $R^{27}$ and $R^{29}$ may be the same or different.

The substituent $R^{28}$ in $-CO-NR^{28}-R^{29}-$ represented by each of $X_1$ to $X_3$ groups represents, similarly to each of $R^{23}$ to $R^{25}$, a hydrogen atom, an alkyl group, a cycloalkyl group or an alkenyl group. These alkyl, cycloalkyl and alkenyl groups may have substituent groups. $R^{28}$ may be the same as either $R^{24}$ or $R^{25}$, or different from them.

Examples of alkyl, cycloalkyl and alkenyl groups $R^{28}$ can represent include the same examples as included in the alkyl, cycloalkyl and alkenyl groups respectively each of $R^{23}$ to $R^{25}$ groups can represent.

The substituent $A_0$ bound to the main chain of repeating units via $X_1$, $X_2$ or $X_3$ represents a monocyclic or polycyclic cycloaliphatic group.

As examples of a monocyclic cycloaliphatic group represented by $A_0$, mention may be made of groups having alicyclic skeletons containing at least 3, preferably 3 to 8, carbon atoms, e.g., cycloaliphatic skeletons including cyclopropane, cyclobutane, cyclopentane and cyclohexane skeletons.

As examples of a polycyclic cycloalipahtic group represented by $A_0$, mention may be made of groups having alicyclic skeletons containing at least 5, preferably 7 to 25, carbon atoms, such as bicyclo-, tricyclo- and tetracycloaliphatic skeletons. These monocyclic or polycyclic cycloaliphatic skeleton-containing groups may further be substituted and be increased in number of carbon atoms contained therein.

As examples of a substituent the polycyclic cycloaliphatic group may have, mention may be made of a hydroxyl group, a halogen atom, a nitro group, a cyano group, an amido group, a sulfonamido group and the alkyl groups recited in the description of $R^{23}$.

Therein, the halogen atom is a fluorine, chlorine, bromine or iodine atom. Examples of such a substituent further include an alkoxy group, an alkoxycarbonyl group, an acyl group, an acyloxy group and a carboxyl group.

As the alkoxy group, 1-8C alkoxy groups, such as methoxy, ethoxy, hydroxyethoxy, propoxy, hydroxypropoxy and butoxy groups, can be recited.

As the alkoxycarbonyl group, methoxycarbonyl and ethoxycarbonyl groups can be recited.

As the acyl group, formyl, acetyl and benzoyl groups can be recited. As the acyloxy group, acetoxy and butyryloxy groups can be recited.

Typical examples of a structure represented by $A_0$, namely a polycyclic or monocyclic type of alicyclic moiety in the poly- or monocycloaliphatic group, are illustrated below.

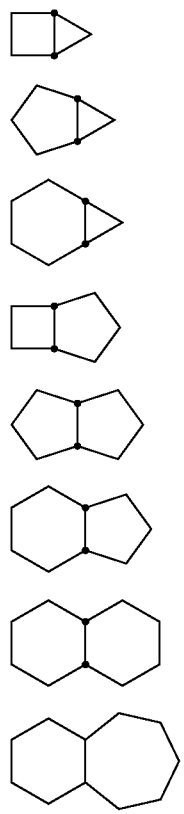

(1)
(2)
(3)
(4)
(5)
(6)
(7)
(8)

-continued

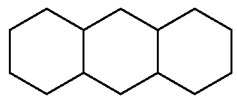

(9)

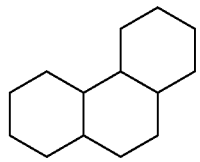

(10)

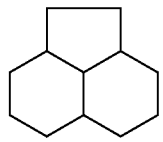

(11)

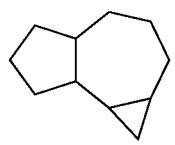

(12)

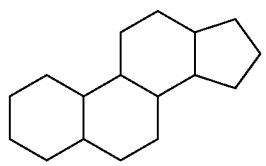

(13)

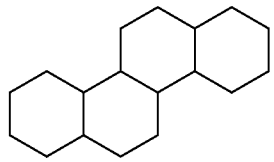

(14)

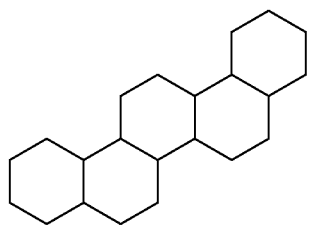

(15)

(16)

(17)

(18)

(19)

-continued
(20) 
(21) 
(22) 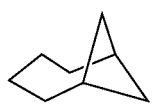
(23) 
(24) 
(25) 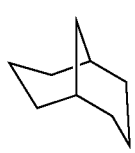
(26) 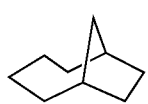
(27) 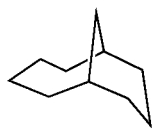
(28) 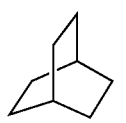
(29) 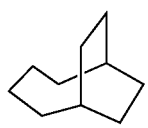
(30) 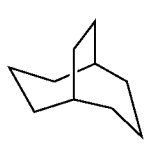
(31) 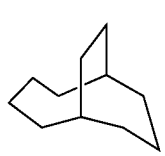
-continued
(32) 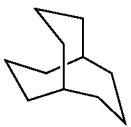
(33) 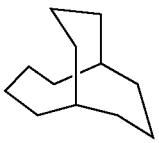
(34) 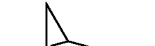
(35) 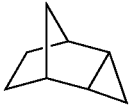
(36) 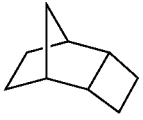
(37) 
(38) 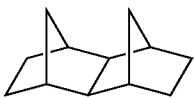
(39) 
(40) 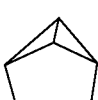
(41) 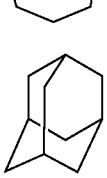
(42) 
(43) 

-continued

(44) 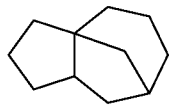

(45) 

(46) 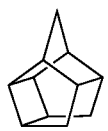

(47) 

(48) 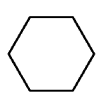

(49) 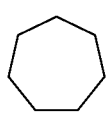

(50) 

The formula (XV) is explained next.

n in formula (XV) is 0 or 1.

Xa and Xb each represent a hydrogen atom or an alkyl group having 1 to 4 carbon atoms.

Ya and Yb represents a hydrogen atom, a hydroxyl group or a group represented by —COOXc. Herein, Xc is a hydrogen atom or an alkyl group in one mode.

Examples of such an alkyl group include alkyl groups having 1 to 8 carbon atoms, preferably alkyl groups having 1 to 4 carbon atoms, such as methyl, ethyl, propyl, butyl and tert-butyl groups. Further, part or all of hydrogen atoms of those alkyl groups each may be replaced with hydroxyl group(s), halogen atom(s) or cyano group(s).

In another mode, Xc represents a constituent of the group —COOXc which functions as an acid-decomposable group in its entity. As examples of such Xc, mention may be made of groups represented by the foregoing formula (x) or (y). In the other mode, Xc may be a group containing an acid-decomposable lactone structure or a group containing an acid-decomposable alicyclic structure.

Resins obtained by copolymerizing repeating units of formula (XV) and maleic anhydride, and resins obtained by copolymerizing repeating units of formula (XV), maleic anhydride and acrylates or methacrylates are also preferred as the resins used in the invention.

Examples of repeating structural units represented by formulae (XII) to (XV) respectively are illustrated below, but these examples should not be construed as limiting the scope of the invention.

(b1) 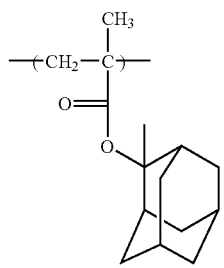

(b2) 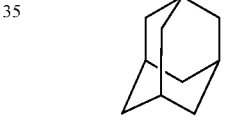

(b3) 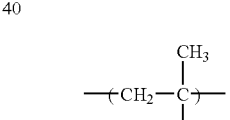

(b4) 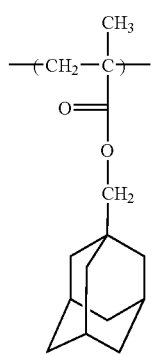

(b5) 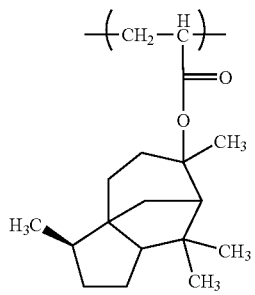

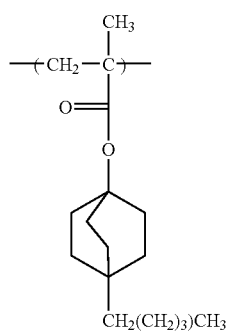
(b6)
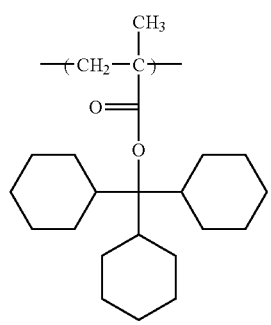
(b7)
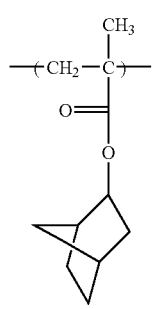
(b8)
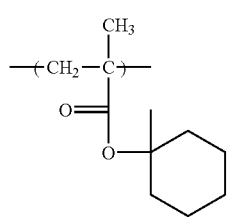
(b9)
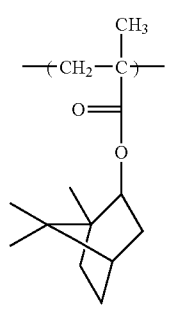
(b10)
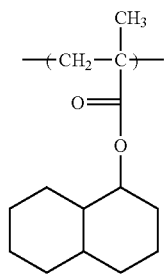
(b11)
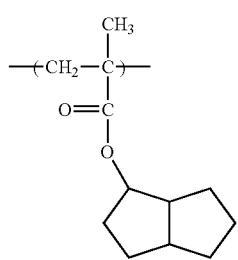
(b12)
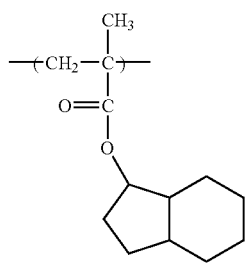
(b13)
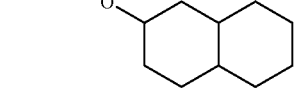
(b14)
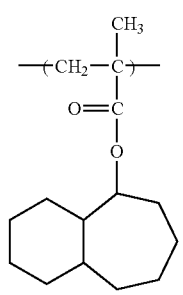
(b15)
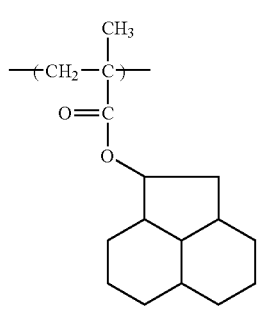
(b16)

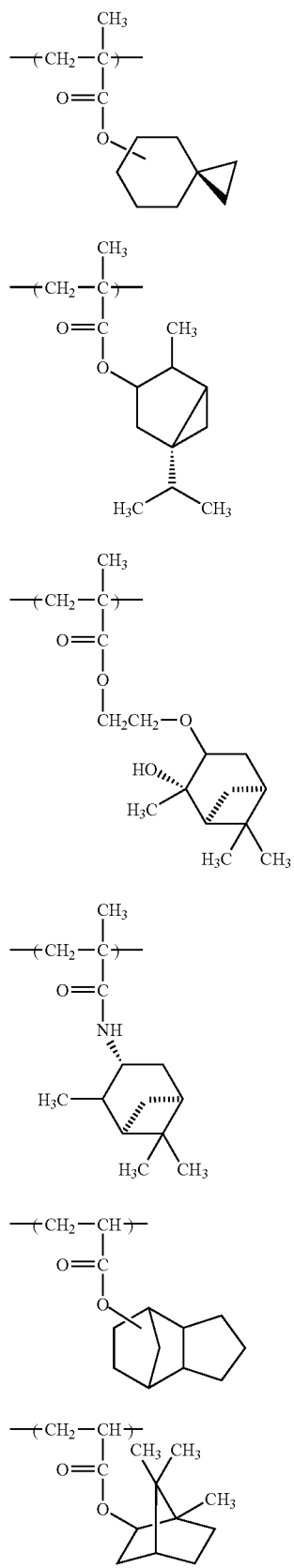
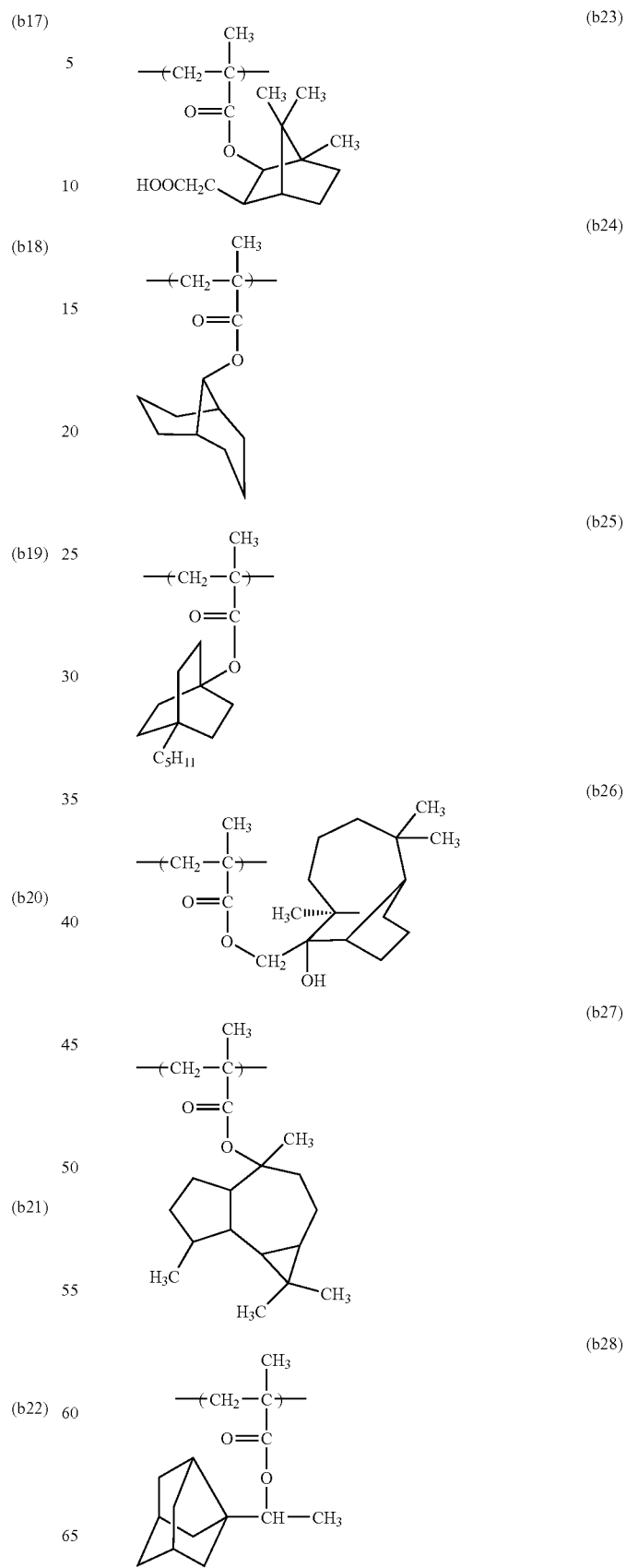

(b29) 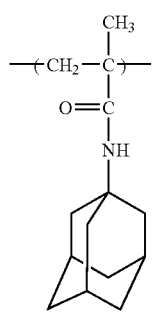
(b30) 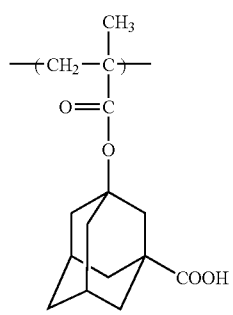
(b31) 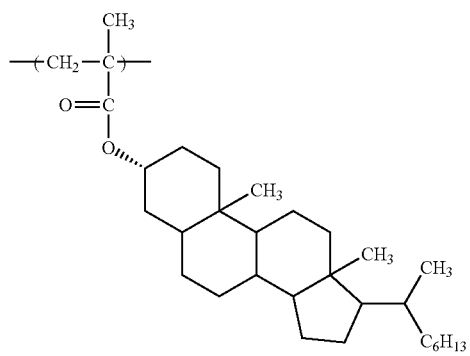
(b32) 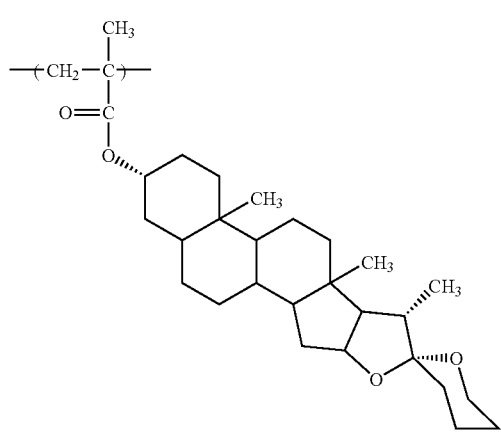
(b33) 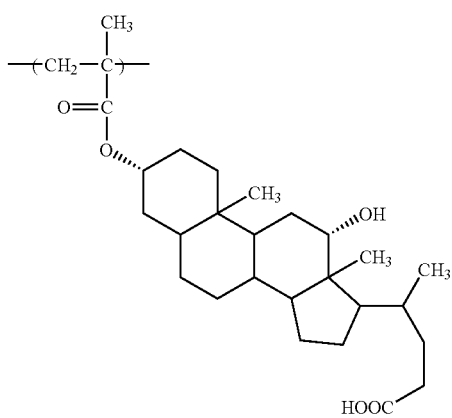
(b34) 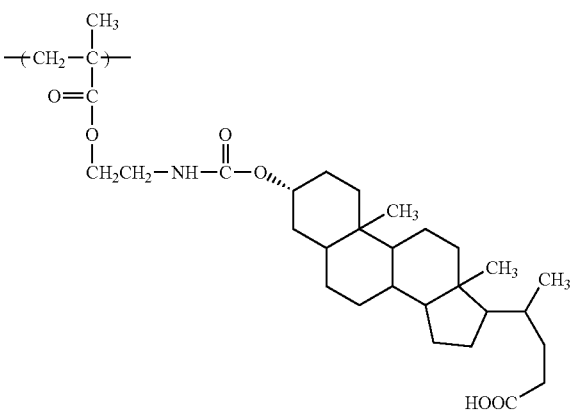
(b35) 
(b36) 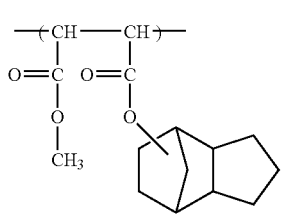

(b37) 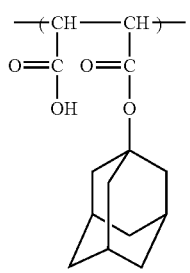
(b38) 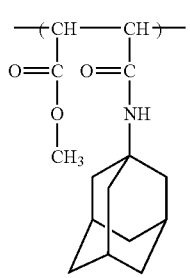
(b39) 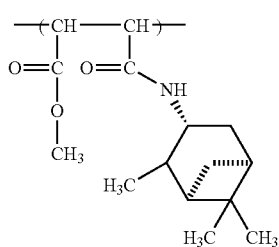
(b40) 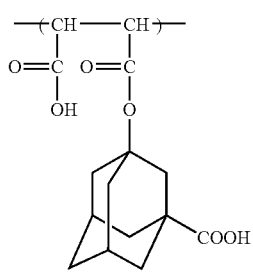
(b41) 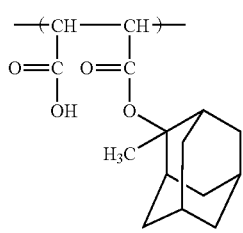
(b42) 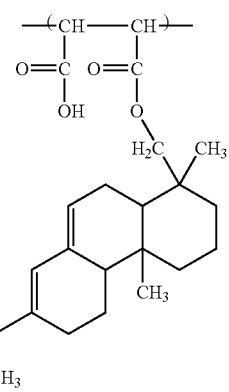
(b43) 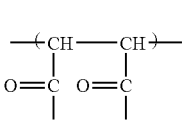
(b44) 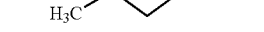
(b45) 

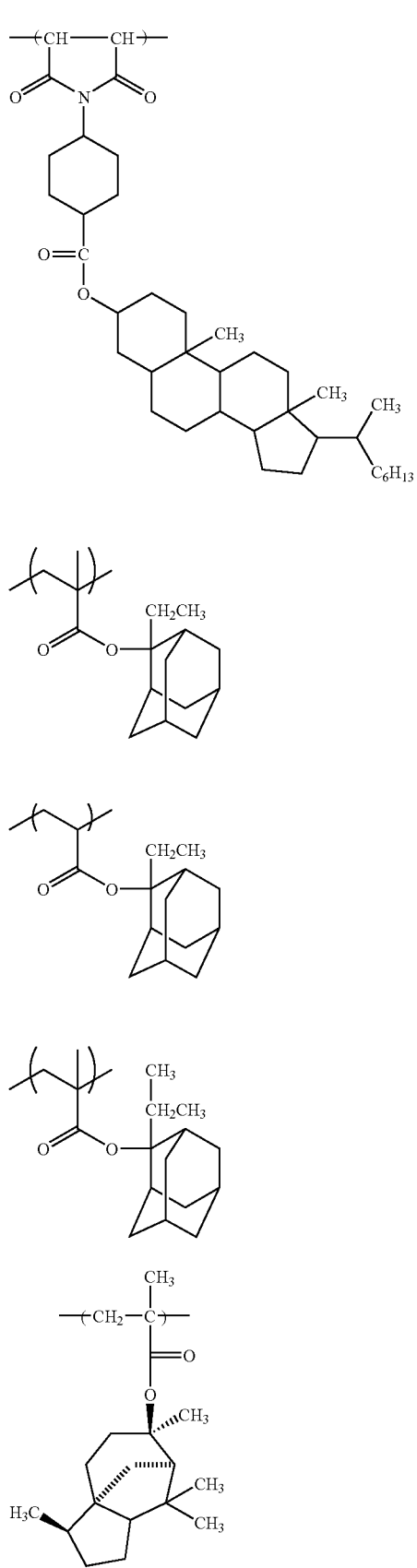

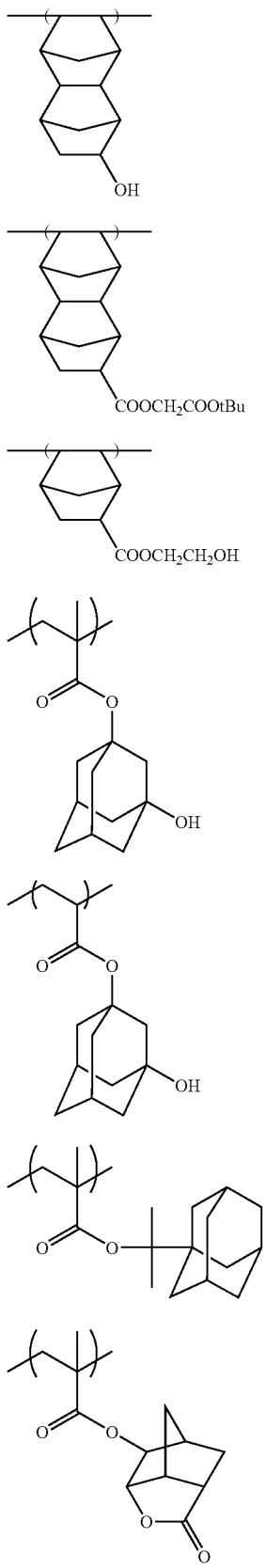

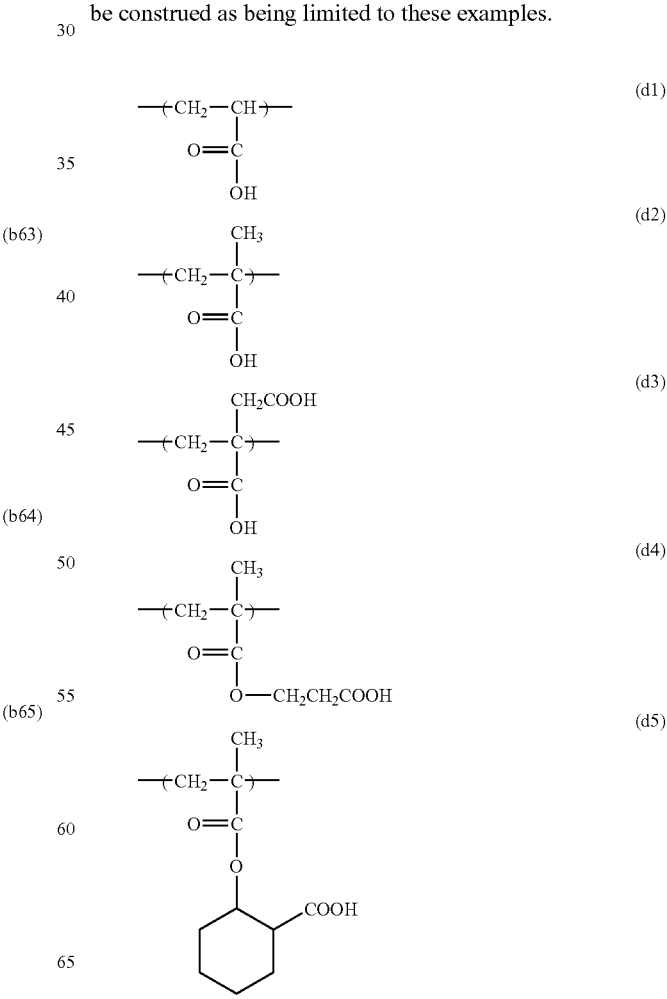

Of these examples, the repeating units (b1), (b2), (b5), (b9), (b47), (b48), (b49), (b50), (b54) (b58) and (b60) are preferred over the others because they are generally decomposable with acids. In particular, the repeating units (b1), (b47), (b48) and (b49), wherein an adamantyl group is attached to the resin main chain via an acid-decomposable structure, are preferable over the others. The use of these repeating units can ensure improvements in dry etching resistance and resolution.

In the acid-decomposable resins as described above, carboxyl groups can further be contained.

These carboxyl groups may be introduced in repeating structural units as recited above or other repeating structural units.

Additionally, the carboxyl groups may be introduced at two or more positions of each structural unit.

The suitable content of all carboxyl group-containing repeating structural units in an acid-decomposable resin comprised in the present positive photosensitive composition, though adjusted depending on the desired properties including alkali developability, adhesion to a substrate and sensitivity, is from 0 to 60 mole %, preferably from 0 to 40%, particularly preferably from 0 to 20 mole %, of the total repeating structural units of the acid-decomposable resin.

Examples of a repeating structural unit containing a carboxyl group are illustrated below, but the invention should not be construed as being limited to these examples.

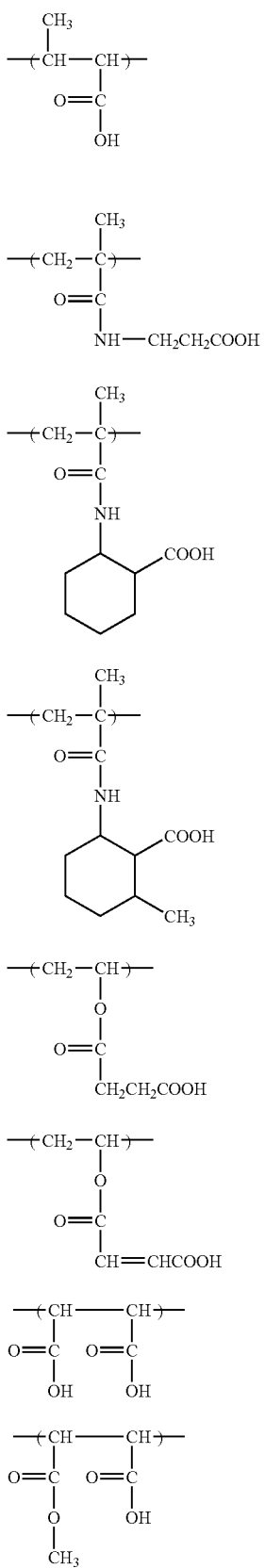
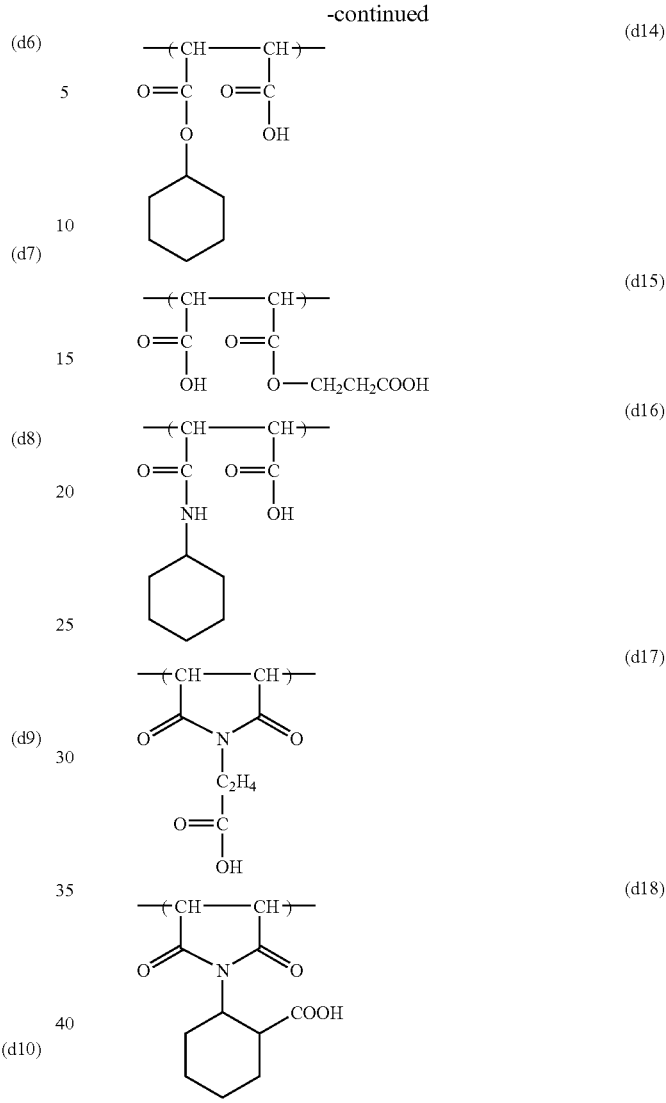

For performance improvement of an acid-decomposable resin, other polymerizable monomers may be introduced into the resin by copolymerization so far as the introduction thereof does not noticeably impair the resin's transparency at wavelengths below 220 nm and dry etching resistance.

Copolymerizable monomers usable for the foregoing purpose are compounds containing one addition polymerizable unsaturated bond per molecule, which can be selected from acrylic acid esters, acrylamides, methacrylic acid esters, methacrylamides, allyl compounds, vinyl ethers, vinyl esters, styrenes or crotonic acid esters.

More specifically, the acrylic acid esters include, e.g., alkyl acrylates (preferably having 1-10C alkyl moieties), such as methyl acrylate, ethyl acrylate, propyl acrylate, t-butyl acrylate, amyl acrylate, cyclohexyl acrylate, ethylhexyl acrylate, octyl acrylate, t-octyl acrylate, chloroethyl acrylate, 2-hydroxyethyl acrylate, 2,2-dimethylhydroxypropyl acrylate, 5-hydroxypentyl acrylate, trimethylolpropane monoacrylate, pentaerythritol monoacrylate, glycidyl acrylate, benzyl acrylate, methoxybenzyl acrylate, furfuryl acrylate and tetrahydrofurfuryl acrylate, aryl acrylates and methoxyethoxyethyl acrylate.

The methacrylic acid esters include, e.g., alkyl methacrylates (preferably having 1-10C alkyl moieties), such as methyl methacrylatae, ethyl methacrylate, propyl methacrylate, isopropyl methacrylate, t-butyl methacrylate, amyl methacrylate, hexyl methacrylate, cyclohexyl methacrylatae, benzyl methacrylate, octyl methacrylate, 2-hydroxyethyl methacrylate, 4-hydroxybutyl methacrylate, 5-hydroxypentyl methacrylate, 2,2,-dimethyl-3-hydroxypropyl methacrylate, trimethylolpropane monomethacrylate, pentaerythritol monomethacrylate, glycidyl methacrylate, furfuryl methacrylate and tetrahydrofurfuryl methacrylate, aryl methacrylates (e.g., phenyl methacrylate, naphthyl methacrylate), and methoxyethoxyethyl methacrylate.

The acrylamides include, e.g., acrylamide, N-alkylacrylamides (preferably having 1-10C alkyl moieties, such as methyl, ethyl, propyl, butyl, t-butyl, heptyl, octyl, cyclohexyl, benzyl and hydroxyethyl), N-arylacrylamides, N,N-dialkylacrylamides (preferably having 1-10C alkyl moieties, such as methyl, ethyl, butyl, isobutyl, ethylhexyl and cyclohexyl), N,N-diacrylacrylamides, N-hydroxyethyl-N-methylacrylamide, and N-2-acetamidoethyl-N-acetylacrylamide.

The methacrylamides include, e.g., methacrylamide, N-alkylmethacrylamides (preferably having 1-10C alkyl moieties, such as methyl, ethyl, t-butyl, ethylhexyl, hydroxyethyl and cyclohexyl), N-acrylmethacrylamides, N,N-dialkylmethacrylamides (the alkyl moieties of which are, e.g., ethyl, propyl or butyl groups), N-hydroxyethyl-N-methylmethacrylamide, N-methyl-N-phenylmethacrylamide, and N-ethyl-N-phenylmethacrylamide.

The allyl compounds include, e.g., allyl esters (such as allyl acetate, allyl caproate, allyl lurate, allyl palmitate, allyl stearate, allyl benzoate, allyl acetoacetate and allyl lactate), and allyloxyethanol.

The crotonic acid esters include, e.g., alkyl crotonates (such as butyl crotonate, hexyl crotonate and glycerol monocrotonate), and the itaconic acid esters include, e.g., dialkyl itaconates (such as dimethyl itaconate, diethyl itaconate and dibutyl itaconate).

Further, copolymerizable monomers usable herein include dialkyl esters of maleic or fumaric acid (e.g., dimethyl maleate and dibutyl fumarate), maleic anhydride, maleimide, acrylonitrile, methacrylonitrile and maleylonitrile.

And besides, any of addition polymerizable unsaturated compounds may be generally used as comonomers.

Of the compounds recited above, methoxyethoxyethyl methacrylate and methoxyethoxyethyl acrylate are particularly preferred over the others.

The suitable content of the repeating structural units derived from other polymerizable monomers in the acid-decomposable resin (B) is not more than 50 mole %, preferably not more than 30 mole %, of the total repeating structural units.

In view of securing transparency to any of actinic rays or radiation, it is desirable that no aromatic rings be contained in the acid-decomposable resin (B). This is because it is difficult to allow irradiated rays to reach the bottom of resist film when the transparency to the irradiated rays is lowered by the introduction of aromatic rings; as a result, the resist comes to have the so-called tapered pattern profile.

The suitable content of the acid-decomposable group-containing repeating structural units in the acid-decomposable resin (B), though adjusted so as to attain a proper balance between dry etching resistance and alkali developability, is at least 10 mole %, preferably at least 15 mole %, particularly preferably at least 20 mole %, of the total repeating structural units.

The suitable content of the alicyclic group-containing structural units (preferably the repeating structural units of formulae (XII) to (XIV)) in the acid-decomposable resin (B) is at least 20 mole % of the total repeating structural units although it is also adjusted so as to attain a proper balance between dry etching resistance and alkali developability. Further, it is preferable that the foregoing content is in the range of 30 to 80 mole %, preferably 35 to 70 mole %, particularly preferably 40 to 60 mole %, of the total repeating structural units.

The suitable content of the lactone structure-containing structural units in the acid-decomposable resin (B) is also adjusted so as to attain a proper balance between dry etching resistance and alkali developability. Specifically, it is at least 5 mole %, preferably at least 10 mole %, particularly at least 20 mole %, of the total repeating structural units.

The suitable weight average molecular weight of the acid-decomposable resin (B) is from 1,000 to 100,000, preferably from 2,000 to 50,000, particularly preferably from 3,000 to 30,000, as measured by GPC and calculated in terms of polystyrene. And the suitable dispersion degree of the acid-decomposable resin (B) is from 1.0 to 5.0, preferably from 1.0 to 3.0.

In each of the present compositions, the suitable proportion of the resin (B) capable of increasing its solubility in an alkali developer under the action of an acid is from 20 to 99.8 weight %, preferably from 50 to 99.5 weight %, on a solids basis.

<<(C) Compound Having Molecular Weight of No Greater than 3,000 and Capable of Decomposing Under Action of Acid to Increase its Solubility in Alkali Developer (Component (C))>>

The compound as Component (C) is contained as an essential component in the second composition, but it may be mixed in the first composition, if desired. The Component (C) is a low molecular compound containing one or more of an acid-decomposable group and capable of increasing its solubility in an alkali developer under the action of an acid. The molecular weight of such a compound is not higher than 3,000, preferably from 200 to 2,000, particularly preferably from 300 to 1,500. The Component (C) functions as an inhibitor against dissolving unexposed areas in an alkali developer. Additionally, the term "acid-decomposable dissolution inhibiting compound" in the following description has the same meaning as Component (C).

Similarly to the foregoing resin (B), it is preferable in the invention that the compound (C) be selected properly depending on the kind of the exposure light or the irradiation ray. Specifically, it is desired that the type of compound (C) be selected in view of transparency and sensitivity to exposure light or irradiation ray, and further dry etching resistance.

Examples of a compound (C) used suitably in a photosensitive composition to undergo exposure to KrF excimer laser or irradiation with electron beams or X-ray include polyhydroxy compounds protected by acid-decomposable groups.

Examples of a compound (C) used preferably in a photosensitive composition to undergo exposure to ArF excimer laser include compounds containing no aromatic rings but containing acid-decomposable groups and alicyclic structures.

Compounds used suitably as compound (C) in photosensitive compositions to undergo exposure to ArF excimer laser are illustrated below in detail.

From the viewpoint of causing no decrease in transparency to radiation of 220 nm or below, acid-decomposable group-containing alicyclic or aliphatic compounds, such as cholic acid derivatives containing acid-decomposable groups as described in *Proceeding of SPIE*, 2724, 355 (1996), are suitable as acid-decomposable dissolution-inhibiting compounds (C). With respect to the acid-decomposable groups and alicyclic structures contained in those compounds, the same ones as recited in the description of the acid-decomposable resins can be recited as examples thereof.

Examples of an acid-decomposable dissolution-inhibiting compound (C) are illustrated below, but the invention should not be construed as being limited to these compounds.

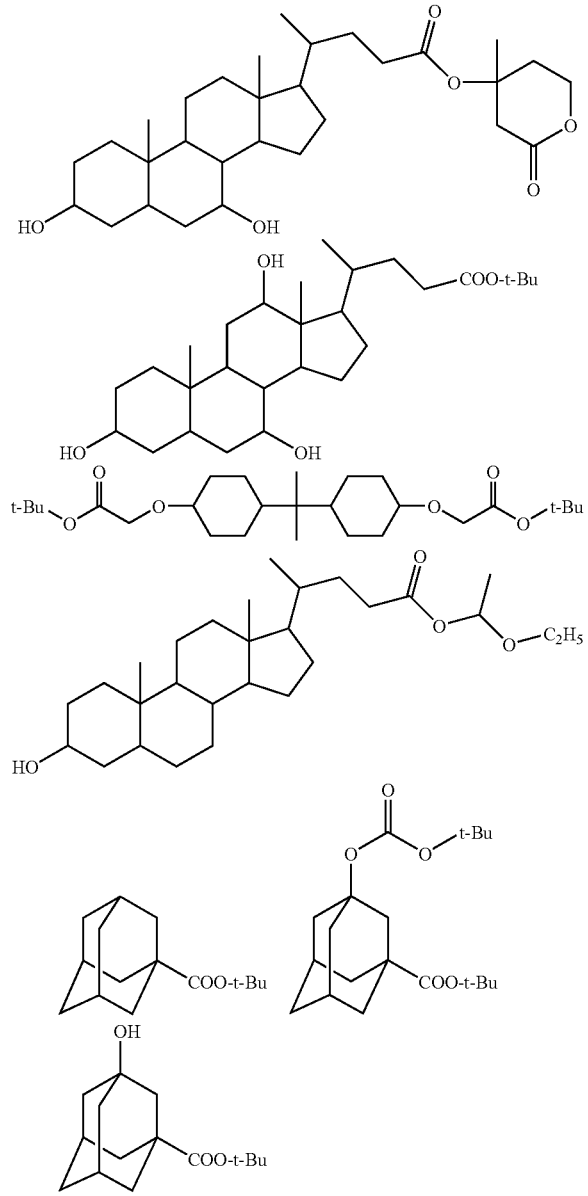

Compounds (C) suitably used in photosensitive compositions to undergo exposure to KrF excimer laser, irradiation with electron beams or irradiation with X-ray are illustrated below in detail.

It is preferable that Component (C), or an acid-decomposable dissolution-inhibiting compound, contain at least two acid-decomposable groups in a condition that at least 8 atoms linked one after another, excluding the atoms constituting the acid-decomposable groups, intervene between the acid-decomposable groups located at the greatest distance from each other.

The acid-decomposable dissolution-inhibiting compounds preferred in the invention are:

(a) compounds containing in each of their structures at least two acid-decomposable groups in a condition that at least 10 atoms, preferably at least 11 atoms, particularly preferably at least 12 atoms, which are linked one after another, excluding the atoms constituting the acid-decomposable groups, intervene between the acid-decomposable groups located at the greatest distance from each other, and (b) compounds containing in each of their structures at least three acid-decomposable groups in a condition that at least 9 atoms, preferably at least 10 atoms, particularly preferably at least 11 atoms, which are linked one after another, excluding the atoms constituting the acid-decomposable groups, intervene between the acid-decomposable groups located at the greatest distance from each other.

Further, it is preferable that the upper limit of the number of atoms intervening between the acid-decomposable groups be 50, preferably 30.

When the acid-decomposable dissolution-inhibiting compound contains at least 3, preferably at least 4, acid-decomposable groups, and even when it contains 2 acid-decomposable groups, they can have markedly improved inhibition capabilities against dissolving alkali-soluble resins as long as the acid-decomposable groups are located at a certain distance or greater.

Additionally, the distance between acid-decomposable groups is expressed in terms of the number of linked atoms intervening between them, excluding the atoms constituting the acid-decomposable groups. For instance, in the case of the following compounds (1) and (2) each, the distance between the acid-decomposable groups is 4 linked atoms, while it is 12 linked atoms in the case of the following compound (3).

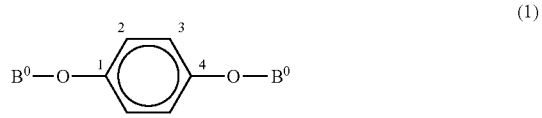
(1)

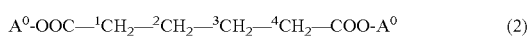
(2)

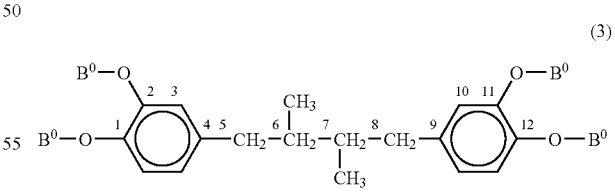
(3)

(acid-decomposable groups: —COO-$A^0$ and —O—$B^0$)

The acid-decomposable dissolution-inhibiting compounds preferred in the invention, though may have a plurality of acid-decomposable groups on one benzene ring, are each comprised of a skeleton wherein one acid-decomposable group is present on one benzene ring.

Examples of a group capable of being decomposed by an acid, namely a group containing a —COO-$A^0$ or —O—$B^0$ group, include —$R^0$—COO-$A^0$ and —Ar—O—$B^0$ groups.

Herein, $A^0$ represents a $-C(R^{01})(R^{02})(R^{03})$, $-Si(R^{01})(R^{02})(R^{03})$ or $-C(R^{04})(R^{05})-O-R^{06}$ group. $B^0$ represents $A^0$ or a $-CO-O-A^0$ group.

$R^{01}$, $R^{02}$, $R^{03}$, $R^{04}$ and $R^{05}$, which are the same or different, each represent a hydrogen atom, an alkyl group, a cycloalkyl group, an alkenyl group or an aryl group. $R^{06}$ represents an alkyl group or an aryl group. Herein, however, at least two among $R^{01}$ to $R^{03}$ groups are groups other than hydrogen, and any two among $R^{01}$ to $R^{03}$ groups or any two among $R^{04}$ to $R^{06}$ groups may combine with each other to form a ring. $R^0$ represents a divalent or higher aliphatic or aromatic hydrocarbon group which may have a substituent, and Ar represents a divalent or higher monocyclic or polycyclic aromatic group which may have a substituent.

Herein, it is preferable for the alkyl group to be a 1-4C alkyl group, such as methyl, ethyl, propyl, n-butyl, sec-butyl or t-butyl group, for the cycloalkyl group to be a 3-10C cycloalkyl group, such as cyclopropyl, cyclobutyl, cylohexyl or adamantyl group, for the alkenyl group to be a 2-4C alkenyl group, such as vinyl, propenyl, allyl or butenyl group, and for the aryl group to be a 6-14C aryl group, such as phenyl, xylyl, toluoyl, cumenyl, naphthyl or anthracenyl group.

As examples of substituents the groups represented by $R^0$ and $-Ar-$ may have, mention may be made of a hydroxyl group, a halogen atom (e.g., fluorine, chlorine, bromine, iodine), a nitro group, a cyano group, an alkyl group as recited above, an alkoxy group such as methoxy, ethoxy, hydroxyethoxy, propoxy, hydroxypropoxy, n-butoxy, isobutoxy, sec-butoxy or t-butoxy group, an alkoxycarbonyl group such as methoxycarbonyl or ethoxycarbonyl group, an aralkyl group such as benzyl, phenetyl or cumyl group, an aralkyloxy group, an acyl group such as formyl, acetyl, butyryl, benzoyl, cinnamyl or valeryl group, an acyloxy group such as butryloxy group, an alkenyl group as recited above, an alkenyloxy group such as vinyloxy, propenyloxy, allyloxy or butenyloxy group, an aryl group as recited above, an aryloxy group such as phenoxy group, and an aryloxycarbonyl group such as benzoyloxy group.

As suitable examples of an acid-decomposable group, mention may be made of a silyl ether group, a cumyl ester group, an acetal group, a tetrahydropyranyl ether group, an enol ether group, an enol ester group, a tertiary alkyl ether group, a tertiary alkyl ester group, and a tertiary alkyl carbonate group. Of these groups, a tertiary alkyl ester group, a tertiary alkyl carbonate group, a cumyl ester group and a tetrahydropyranyl ether group are preferred over the others.

Suitable examples of Component (C) include compounds prepared by protecting a part or all of phenolic OH groups contained in the polyhydroxy compounds as disclosed in JP-A-1-289946, JP-A-1-289947, JP-A-2-2560, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JP-A-3-279958, JP-A-3-279959, JP-A-4-1650, JP-A-4-1651, JP-A-4-11260, JP-A-4-12356, JP-A-4-12357, and Japanese Patent Application Nos. 3-33229, 3-230790, 3-320438, 4-25157, 4-52732, 4-103215, 4-104542, 4-107885, 4-107889 and 4-152195 with the $-R^0-COO-A^0$ or $B^0$ groups described above.

Of these compounds, the compounds prepared from the polyhydroxy compounds disclosed in JP-A-1-289946, JP-A-3-128959, JP-A-3-158855, JP-A-3-179353, JP-A-3-200251, JP-A-3-200252, JP-A-3-200255, JP-A-3-259149, JP-A-3-279958, JP-A-4-1650, JP-A-4-11260, JP-A-4-12356, JP-A-4-12357, and Japanese Patent Application Nos. 4-25157, 4-103215, 4-104542, 4-107885, 4-107889 and 4-152195 are preferred over the others.

Examples of skeletons of compounds preferred as Component (C) in the invention are illustrated below.

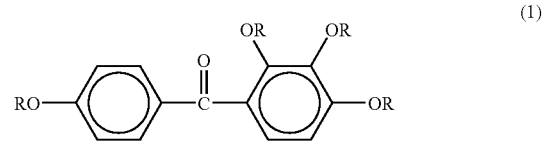
(1)

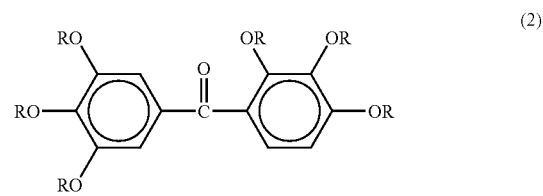
(2)

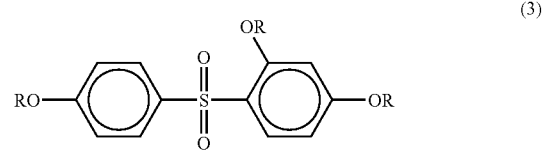
(3)

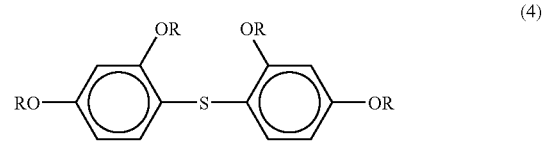
(4)

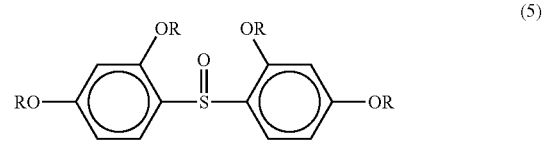
(5)

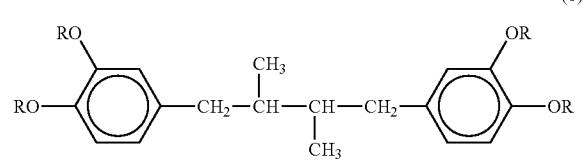
(6)

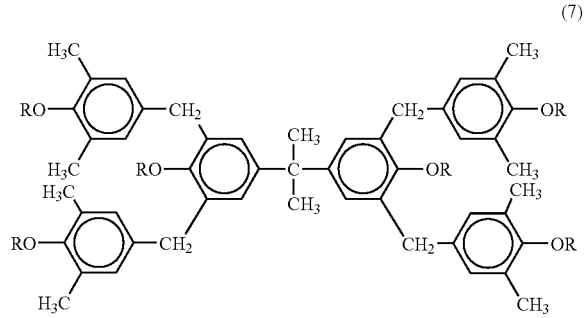
(7)

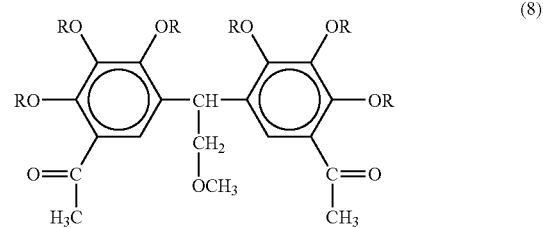
(8)

(9) 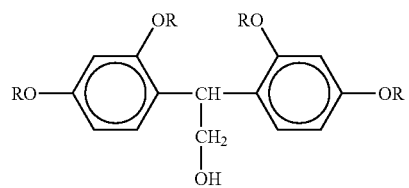
(10) 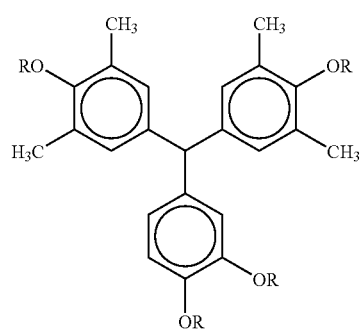
(11) 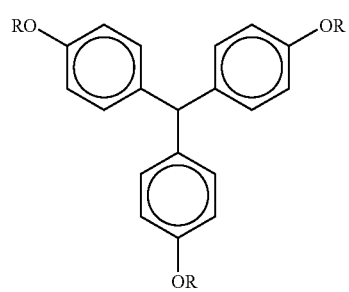
(12) 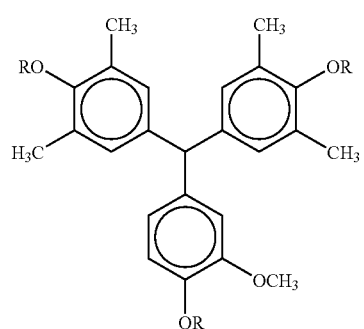
(13) 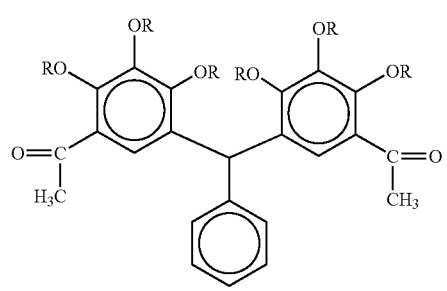
(14) 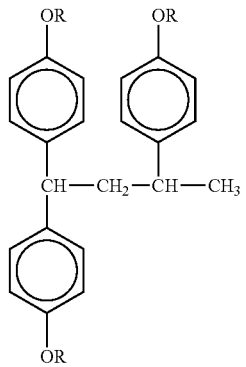
(15) 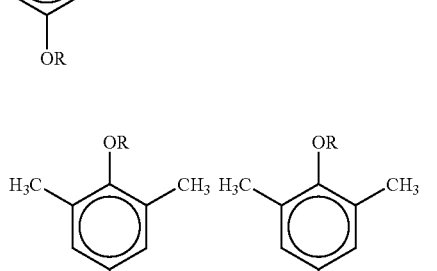
(16) 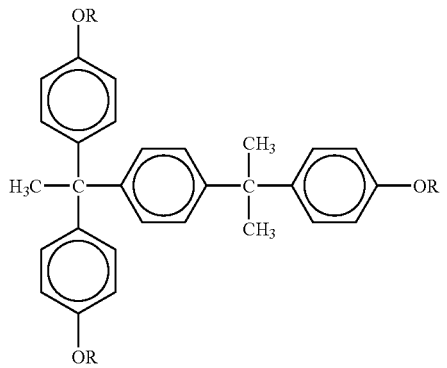
(17) 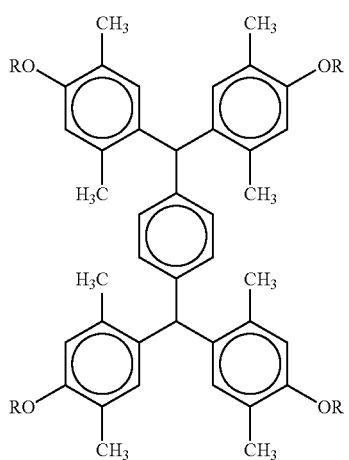

-continued
(18)
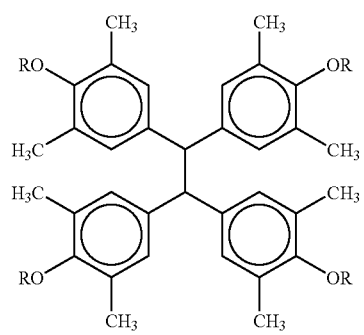
(19)
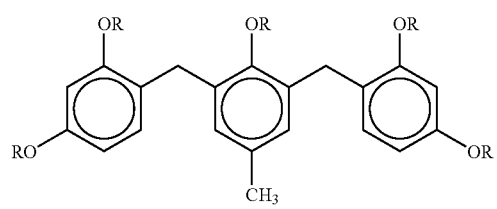
(20)
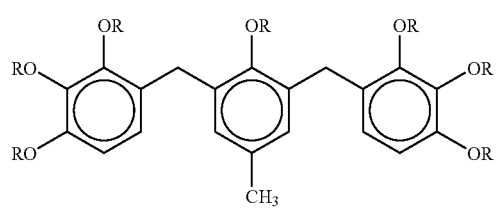
(21)
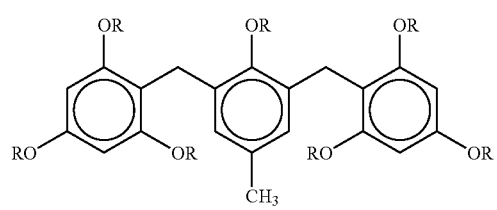
(22)
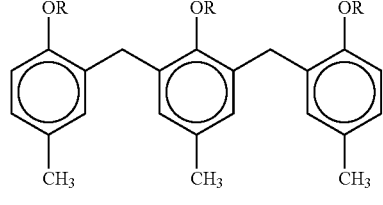
(23)
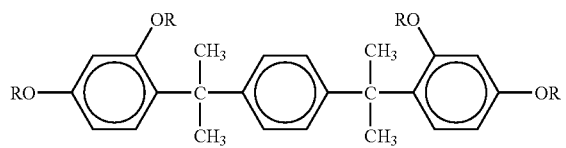
(24)
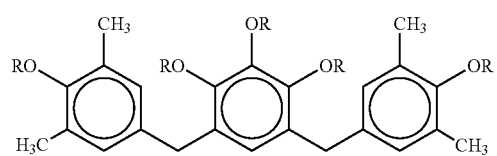
-continued
(25)
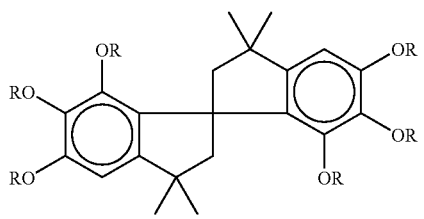
(26)
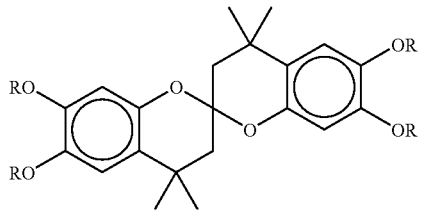
(27)
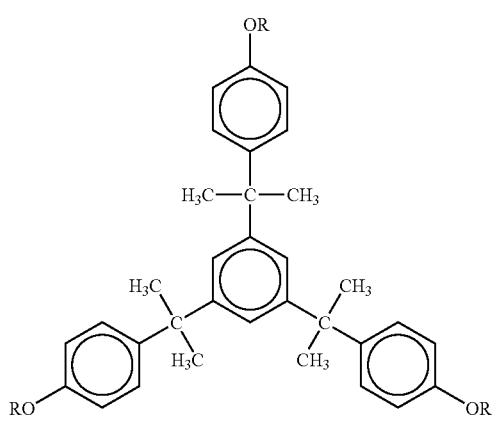
(28)
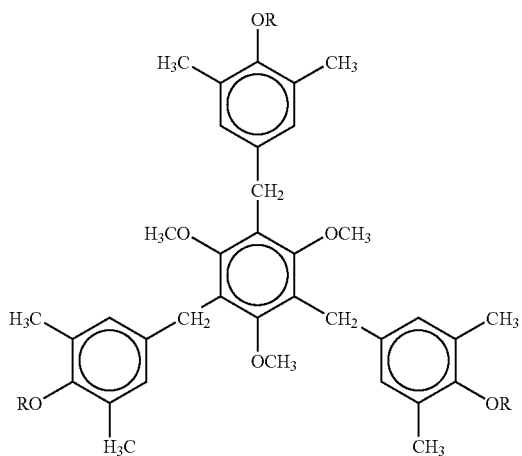

-continued
(29)
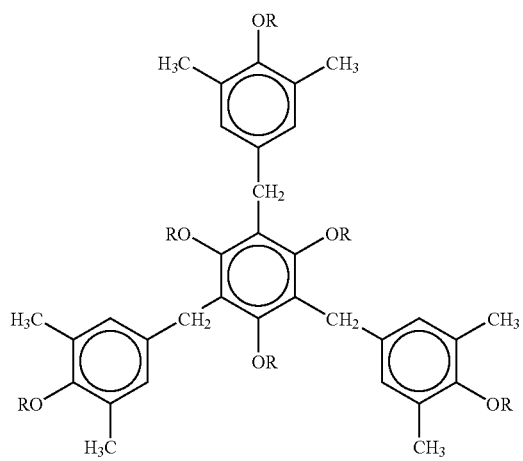
(30)
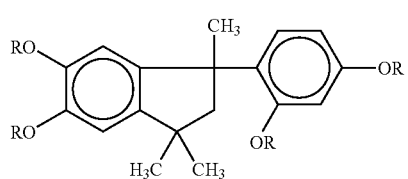
(31)
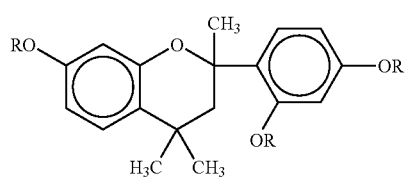
(32)
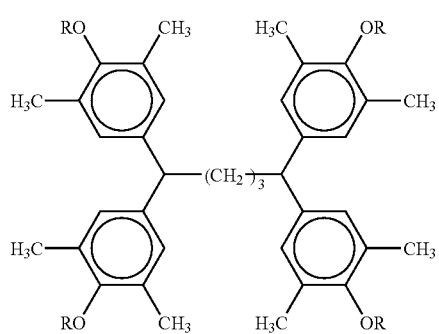
(33)
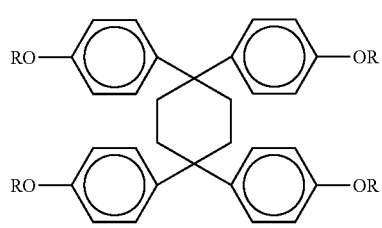
-continued
(34)
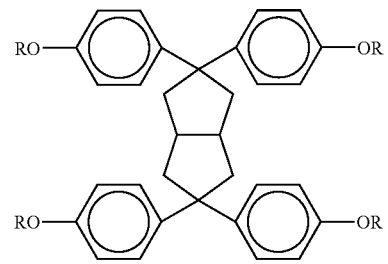
(35)
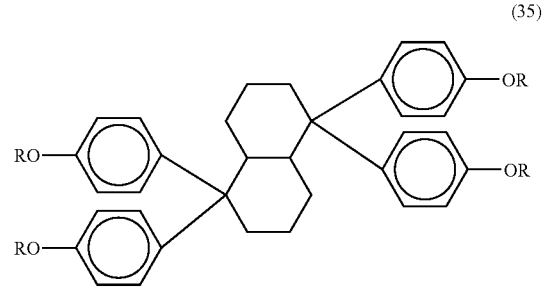
(36)
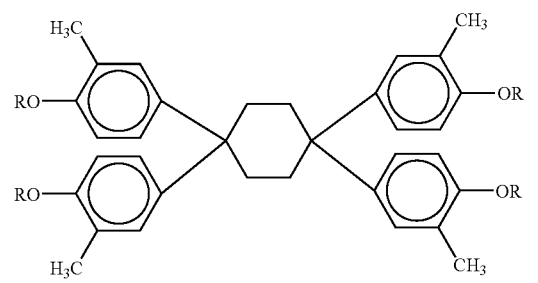
(37)
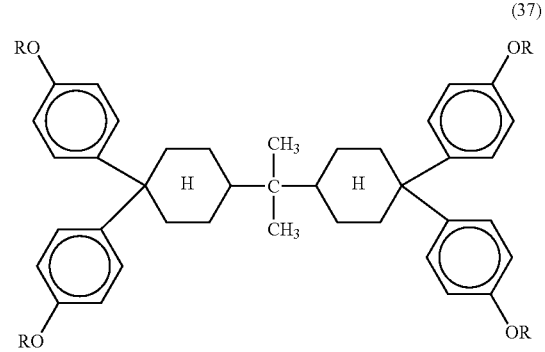

-continued
(38)
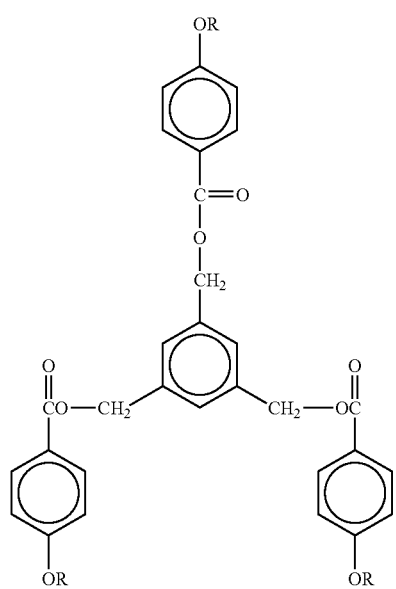
(39)
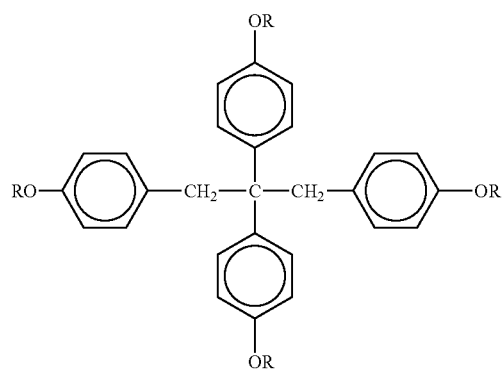
(40)
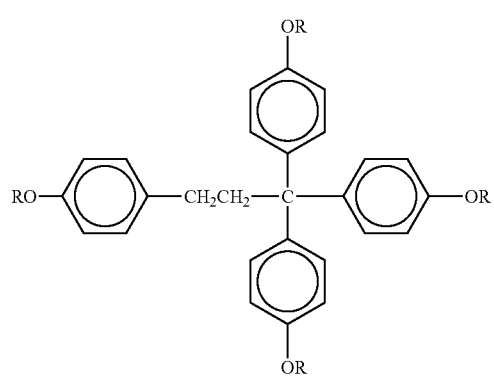
-continued
(41)
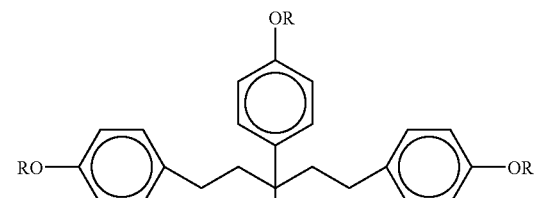
(42)
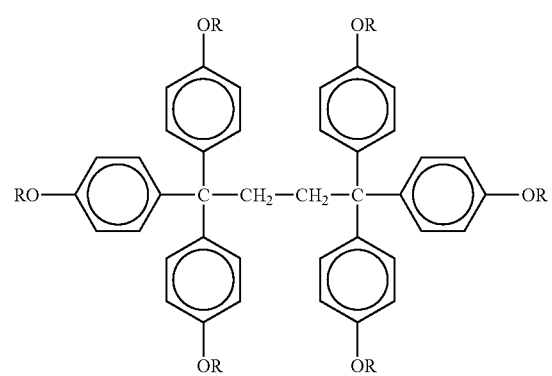
(43)
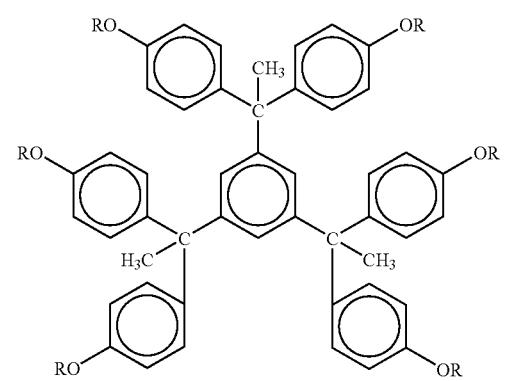
(44)
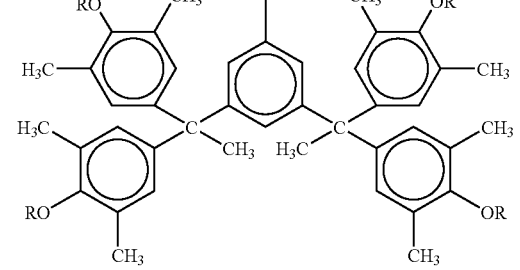

Each of R groups in Compounds (1) to (44) represents a hydrogen atom,

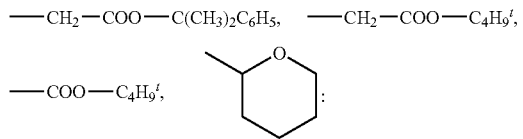

Therein, at least two R groups in each compound, or three R groups depending on the compound structure, are groups other than hydrogen, and R groups in each compound may be the same or different.

In the first composition, the suitable proportion of Component (C) is from 3 to 45 weight %, preferably from 5 to 30 weight %, particularly preferably from 10 to 20 weight %, based on the total solids therein.

In the second composition also, the suitable proportion range of Component (C) is the same as in the first composition.

<<(D) Alkali-Soluble Resin (Component (D))>>

An alkali-soluble resin (D) is an essential component in the second composition. And it may be mixed in the first composition, if desired. The alkali-soluble resin (D) is a resin insoluble in water but soluble in an alkali developer, and used for adjusting the alkali solubility of the second composition. Such a resin contains no acid-decomposable groups in a substantial sense.

Similarly to the foregoing resin (B), it is preferable in the invention that the resin (D) be selected properly depending on the kind of the exposure light or the irradiation ray. Specifically, it is desired that the type of the resin (D) be selected in view of transparency and sensitivity to exposure light or irradiation ray, and further dry etching resistance.

Examples of a resin (D) used suitably in a photosensitive composition to undergo exposure to KrF excimer laser or irradiation with electron beams or X-ray include resins having alkali-soluble groups (such as poly(hydroxystyrene) resins).

Examples of a resin (D) used preferably in a photosensitive composition to undergo exposure to ArF excimer laser include resins containing no aromatic rings but containing alkali-soluble groups.

Resins which can be suitably used as resin (D) in photosensitive compositions to undergo exposure to ArF excimer laser are illustrated below in detail.

Such resins can include novolak resins whose molecular weights are in the range of about 1,000 to 20,000 and poly (hydroxystyrene) derivatives whose molecular weights are in the range of about 3,000 to 50,000, but these resins each show a great absorption peak at a wavelength of 250 nm or below. Therefore, it is preferable that they be used after undergo partial hydrogenation or in a proportion of no higher than 30 weight % to the total resins used.

In addition, resins containing carboxyl groups as alkali-soluble groups can be used, too. From the viewpoint of enhancing dry etching resistance, it is desirable for those resins to contain mono- or polycycloaliphatic groups. Specifically, such resins include a copolymer of a methacrylic acid ester having a cycloaliphatic structure showing no acid-decomposability and (meth)acrylic acid, and a resin prepared from a terminal carboxyl group-containing alicyclic ester of (meth)acrylic acid.

Resins which can be suitably used as resin (D) in photosensitive compositions to undergo exposure to KrF excimer laser, or irradiation with electron beams or X-ray are described below in detail.

Examples of resins usable as Component (D) include novolak resin, hydrogenated novolak resin, acetone-pyrogallol resin, poly(o-hydroxystyrene), poly(m-hydroxystyrene), poly(p-hydroxystyrene), hydrogenated poly(hydroxystyrene), poly(halogen- or alkyl-substituted hydroxystyrene), copolymer of hydroxystyrene and N-substituted maleimide, copolymer of o/p-hydroxystyrene and m/p-hydroxystyrene, poly(hydroxystyrene) whose hydroxyl groups are partially O-alkylated (e.g., O-methylated, O-(1-methoxy)ethylated, O-(1-ethoxy)ethylated, O-2-tetrahydropyranylated, or O-(t-butoxycarbonyl)methylated in a proportion of 5 to 30 mole %) or O-acylated (e.g., O-acetylated or O-(t-butoxy)carbonylated in a proportion of 5 to 30 mole %), styrene-maleic anhydride copolymer, styrene-hydroxystyrene copolymer, α-methylstyrene-hydroxystyrene copolymer, carboxyl group-containing methacrylate resin and derivatives thereof, and polyvinyl alcohol derivatives. However, these examples should not be construed as limiting the scope of the invention.

Of these alkali-soluble resins as resin (D), novolak resin, poly(o-hydroxystyrene), poly(m-hydroxystyrene), poly(p-hydroxystyrene) and copolymers of o-, m- and p-hydroxystyrenes, an alkyl-substituted poly(hydroxystyrene), partially O-alkylated or O-acylated poly(hydroxystyrene), styrene-hydroxystyrene copolymer and α-methylstyrene-hydroxystyrene copolymer are preferred over the others. The novolak resin can be synthesized by subjecting specified monomers as main components and aldehydes to addition condensation reaction in the presence of an acid catalyst.

The suitable weight average molecular weight of novolak resin is from 1,000 to 30,000. When the weight average molecular weight is lower than 1,000, great reduction in resist film thickness is caused in unirradiated areas by development. The weight average molecular weight higher than 30,000, on the other hand, becomes a cause of a decrease in developing speed. The especially suitable range is from 2,000 to 20,000.

Further, the weight average molecular weight of resins other than novolak resin, such as the poly(hydroxystyrene) and derivatives thereof and copolymers as recited above, is not lower than 2,000, preferably from 5,000 to 200,000, particularly preferably from 8,000 to 100,000. From the viewpoint of improving heat resistance of the resist film, it is preferable that the resin as recited above has a weight average molecular weight of no lower than 10,000.

Herein, the weight average molecular weight is defined as the value measured by GPC and calculated in terms of polystyrene.

The alkali-soluble resins as recited above may be used as a mixture of two or more thereof.

The suitable proportion of alkali-soluble resins used is from 40 to 97 weight %, preferably from 60 to 90 weight %, based on the total solids in the second composition.

<<(E) Nitrogen-Containing Basic Compound>>

In order to reduce a change in performance due to time passage from exposure to baking, it is desirable for the present positive photosensitive compositions to contain nitrogen-containing basic compounds.

Such basic compounds are preferably represented by the following structural formulae (A) to (E).

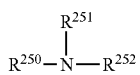
(A)

In the above formula (A), $R^{250}$, $R^{251}$ and $R^{252}$ each independently represent a hydrogen atom, an alkyl group having 1 to 6 carbon atoms, an aminoalkyl group having 1 to 6 carbon atoms, a hydroxyalkyl group having 1 to 6 carbon atoms, or a substituted or unsubstituted aryl group having 6 to 20 carbon atoms. Further, $R^{250}$ and $R^{251}$ may combine with each other to form a ring.

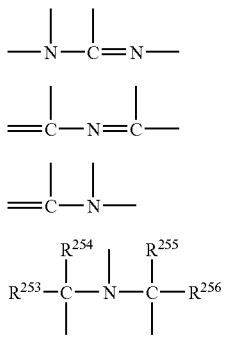

In the above formula, $R^{253}$, $R^{254}$, $R^{255}$ and $R^{256}$ each independently represent an alkyl group having 1 to 6 carbon atoms.

Suitable examples of such basic compounds include substituted or unsubstituted guanidine, substituted or unsubstituted aminopyridine, substituted or unsubstituted aminoalkylpyridine, substituted or unsubstituted aminopyrrolidine, substituted or unsubstituted indazole, substituted or unsubstituted pyrazole, substituted or unsubstituted pyrazine, substituted or unsubstituted pyrimidine, substituted or unsubstituted purine, substituted or unsubstituted imidazoline, substituted or unsubstituted pyrazoline, substituted or unsubstituted piperazine, substituted or unsubstituted aminomorpholine, substituted or unsubstituted aminoalkylmorpholine, mono-, di- and tri-alkylamines, substituted or unsubstituted aniline, substituted or unsubstituted piperidine, and mono- or di-ethanolamine. As examples of substituents the above-recited compounds can have preferably, mention may be made of an amino group, an aminoalkyl group, an alkylamino group, an aminoaryl group, an arylamino group, an alkyl group, an alkoxy group, an acyl group, an acyloxy group, an aryl group, an aryloxy group, a nitro group, a hydroxyl group and a cyano group.

Specific examples of basic compounds preferred in particular include guanidine, 1,1-dimethylguanidine, 1,1,3,3,-tetramethylguanidine, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoethylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinoppiperidine, 2-iminopiperidine, 1-(2-aminoethyl)pyrrolidine, pyrazole, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine, N-(2-aminoethyl)morpholine, 1,5-diazobicyclo[4.3.0]nona-5-ene, 1,8-diazabicyclo[5.4.0]undeca-7-ene, 2,4,5-triphenylimidazole, tri(n-butyl)amine, tri(n-octyl)amine, N-phenyldiethanolamine, N-hydroxyethylpiperidine, 2,6-diisoproopylaniline and N-cyclohexyl-N'-morpholinoethylthiourea. However, these examples should not be construed as limiting the scope of the invention.

These nitrogen-containing basic compounds (E) may be used alone or as mixtures of two or more thereof. The proportion of nitrogen-containing basic compounds used is generally from 0.001 to 10 weight %, preferably from 0.01 to 5 weight %, based on the total solids in the photosensitive resin composition. The effect of the foregoing nitrogen-containing basic compounds cannot be produced when the compounds are added in a proportion lower than 0.001 weight %; while the addition in a proportion higher than 10 weight % may cause a decrease in sensitivity and deterioration of developability in the unexposed areas.

<<(F) Surfactant Containing Either Fluorine or Silicon Atom, or Both Fluorine and Silicone Atoms>>

It is preferable for the present positive photosensitive resin compositions each to contain a surfactant containing at least one fluorine atom, a surfactant containing at least one silicon atom, or a surfactant containing both fluorine and silicon atoms. Also, any two or more of these surfactants may be contained as a mixture.

When the light source of 250 nm or below, especially 220 nm or below, is used for exposure, the present positive photosensitive compositions each can have satisfactory sensitivity and resolution by containing the foregoing surfactant(s) as Component (F) and can provide resist patterns having a good adhesion and reduced in development defects.

As examples of such surfactants, mention may be made of the surfactants disclosed in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, and U.S. Pat. Nos. 5,405,720, 5,360,692, 5,529,881, 5,296,330, 5,436,098, 5,576,143, 5,294,511 and 5,824,451. Further, the commercially available surfactants as recited below can also be used as they are.

Examples of commercial surfactants usable in the invention include fluorine-containing surfactants, such as Eftop EF301, EF303 (manufactured by Shin-Akita Kasei K.K.), Florad FC430, FC431 (manufactured by Sumitomo 3M, Inc.), Megafac F171, F173, F176, F189, R08 (manufactured by Dainippon Ink & Chemicals, Inc.), Surflon S-382, SC101, SC102, SC103, SC104, SC105, SC106 (manufactured by Asahi Glass Co., Ltd.) and Troysol S-366 (manufactured by Troy Chemical Industries, Inc.), and silicon-containing surfactants, such as polysiloxane polymer KP-341 (manufactured by Shin-Etsu Chemical Industry Co., Ltd.).

The suitable proportion of surfactants used is from 0.0001 to 2 weight %, preferably from 0.001 to 1 weight %, based on the total solids in the positive photosensitive resin composition.

<<Other Substances>>

In the present positive photosensitive compositions, dyes, plasticizers, surfactants other than the foregoing Component (F), photosensitizers, and compounds for promoting solubility in a developer may further be contained.

The compounds for promoting solubility in a developer which can be used in the invention are low molecular compounds containing at least two per molecule of phenolic OH groups, or containing at least one per molecule of carboxyl group. When they are used in the compositions suitable for ArF exposure, it is preferable for them to be carboxyl group-containing alicyclic or aliphatic compounds.

The suitable proportion of these dissolution-promoting compounds is from 2 to 50 weight %, preferably from 5 to 30 weight %, to the resin (B) capable of decomposing under the action of acid to increase the solubility in an alkali developer. Those compounds added in a proportion greater than 50 weight % give rise to aggravation of development residue and a new defect that patterns are deformed at the time of development.

On the other hand, the compounds containing at least two phenolic OH groups per molecule have suitability for KrF exposure, or electron-beam or X-ray irradiation. And they are preferably phenolic compounds having a molecular weight of no higher than 1,000. Although these compounds are required to have at least two phenolic OH groups per molecule, development latitude improving effect is lost when the number of phenolic OH groups in a molecule exceeds 10. Further, in the cases where the ratio of the number of phenolic OH groups to the number of aromatic rings is smaller than 0.5, film-thickness dependence is great and development latitude may become narrow. On the other hand, when the foregoing ratio is greater than 1.4, the stability of the composition is degraded, and it becomes difficult to achieve high resolution and satisfactory film-thickness dependence.

Those phenolic compounds whose molecular weights are not higher than 1,000 can be synthesized easily by reference to the methods as described in JP-A-4-122938, JP-A-23-28531, U.S. Pat. No. 4,916,210 and European Patent 2,192,294.

Examples of such phenolic compounds include those recited below, but the compounds usable in the invention should not be construed as being limited to these examples.

Namely, the phenolic compounds usable in the invention include resorcinol, phloroglucine, 2,3,4-trihydroxybenzophenone, 2,3,4,4'-tetrahydroxybenzophenone, 2,3,4,3',4', 5'-hexahydroxybenzophenone, acetone-pyrogallol condensation resin, phloroglucoside, 2,4,2',4'-biphenyltetraol, 4,4'-thiobis(1,3-dihydroxy)benzene, 2,2',4,4',-tetrahydroxydiphenyl ether, 2,2',4,4'-tetrahydroxydiphenyl sulfoxide, 2,2',4,4'-tetrahydroxydiphenyl sulfone, tris(4-hydroxyphenyl)methane, 1,1-bis(4-hydroxyphenyl)cyclohexane, 4,4-(α-methylbenzylidene)bisphenol, α,α',α''-tris(4-hydroxyphenyl)-1,3,5-triisopropylbenzene, α,α',α''-tris(4-hydroxyphenyl)-1-ethyl-4-isopropylbenzene, 1,2,2-tris(hydroxyphenyl)propane, 1,1,2-tris(3,5-dimethyl-4-hydroxyphenyl)propane, 2,2,5,5-tetrakis(4-hydroxyphenyl) hexane, 1,2-tetrakis(4-hydroxyphenyl)ethane, 1,1,3-tris(hydroxyphenyl)butane, and para[α,α,α',α'-tetrakis(4-hydroxyphenyl)]xylene.

Examples of carboxyl group-containing alicyclic and aliphatic compounds include carboxylic acid derivatives having steroid structures, such as cholic acid, deoxycholic acid and lithocholic acid, adamantanecarboxylic acid derivatives, adamantanedicarboxylic acid, cyclohexanecarboxylic acid, and cyclohexanedicarboxylic acid. However, these examples should not be construed as limiting the scope of the invention.

To the present compositions, surfactants other than the foregoing fluorine- and/or silicon-containing surfactants (F) can also be added. Examples of surfactants which can be added include nonionic surfactants, such as polyoxyethylene alkyl ethers (e.g., polyoxyethylene lauryl ether, polyoxyethylene stearyl ether, polyoxyethylene cetyl ether, polyoxyethylene oleyl ether), polyoxyethylene alkyl aryl ethers (e.g., polyoxyethylene octyl phenol ether, polyoxyethylene nonyl phenyl ether), polyoxyethylene-polyoxypropylene block copolymers, sorbitan fatty acid esters (e.g., sorbitan monolaurate, sorbitan monopalmitate, sorbitan monostearate, sorbitan monooleate, sorbitan trioleate, sorbitan tristearate), and polyoxyethylenesorbitan fatty acid esters (e.g., polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate).

These surfactants may be added alone, or some of them can be added as combinations.

<<Use of Present Composition>>

Each of the present photosensitive compositions is a solution prepared by mixing the ingredients mentioned above in a proper solvent, and used in a state of being coated on a specified support. Examples of a solvent suitably used herein include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethylacetate, ethylene glycolmonoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran. These solvents are used alone or as mixtures.

Of the solvents recited above, cyclohexanone, 2-heptanone, propylene glycol monomethyl ether acetate, propylene glycol monomethyl ether, ethyl lactate and ethyl ethoxypropionate are preferred over the others, and these solvents may be used alone or as a 1:9 to 9:1 mixture of any two of them.

The positive photosensitive composition dissolved in a solvent is coated on a specified substrate in the following manner.

Namely, the photosensitive composition is coated on a substrate (e.g., silicon/silicon dioxide coating) as used for production of precision-integrated circuit elements by means of an appropriate coating machine, such as a spinner or a coater.

After coating, the photosensitive composition is subjected to exposure to light via the desired mask, baking and then development. Thus, it can provide resist patterns of good quality. In the exposure to light, far ultraviolet rays having wavelengths of 250 nm or below, preferably 220 nm or below, are used to advantage. More specifically, it is preferable for the exposure light to be KrF excimer laser (248 nm), ArF excimer laser (193 nm), F2 excimer laser (157 nm), X-ray or electron beams can be used as exposure light.

The developer used in subjecting the present photosensitive composition to development-processing may be an aqueous alkaline solution containing an inorganic alkali such as sodium hydroxide, potassium hydroxide, sodium carbonate, sodium silicate, sodium metasilicate or aqueous ammonia, a primary amine such as ethylamine or n-propylamine, a secondary amine such as diethylamine or di-n-butylamine, a tertiary amine such as triethylamine or methyldiethylamine, an alcoholamine such as dimethylethanolamine or triethanolamine, a quaternary ammonium salt such as tetramethylammonium hydroxide or tetraethylammonium hydroxide, or a cyclic amine such as pyrrole or piperidine.

To the aqueous alkaline solution, alcohol and surfactants may further be added in preferable amounts.

The invention will now be illustrated in more detail by reference to the following examples, but these examples should not be construed as limiting the scope of the invention in any way.

SYNTHESIS EXAMPLE 1

Synthesis of Sulfonic Acid Generator as Component (A)

<(1) Synthesis of Compound I-1>

To 20 g of bis(t-butylphenyl) iodonium iodide were added 500 ml of methanol and 8.9 g of silver oxide (I). This admixture was placed in a dark room and stirred for 4 hours at room temperature. The resulting reaction solution was filtered sequentially with filter paper and a 0.1-μm filter, thereby removing the silver compound. The filtrate was mixed with 12.1 g of perfluoroethoxyethanesulfonic acid, and concentrated. The thus obtained oily matter was dissolved in 1-liter of ethyl acetate, and washed twice with a 2% aqueous solution of tetramethylammonium hydroxide and further twice with distilled water. The organic layer was dried and concentrated to yield 48 g of Compound I-1.

300 MHz $^1$H-NMR (CDCl$_3$)

δ 0.6 (t, 6H), δ 1.15 (s, 12H), δ 1.55 (q, 4H), δ 7.3 (d, 4H), δ 7.8 (d, 4H)

Compounds (I-2) to (I-9) were also synthesized using the corresponding sulfonium iodides respectively in accordance with the same method as described above.

<(2) Synthesis of Compound II-1>

Triphenylsulfonium iodide in an amount of 28.1 g was added 500 ml of methanol, and thereto was added 17.3 g of silver oxide (I). This admixture was placed in a dark room and stirred for 4 hours at room temperature. The resulting reaction solution was filtered sequentially with filter paper and a 0.1-μm filter, thereby removing the silver compound. The filtrate was mixed with 25 g of perfluoroethoxyethanesulfonic acid, and concentrated. The thus obtained oily matter was dissolved in 1-liter of ethyl acetate, and washed twice with a 2% aqueous solution of tetramethylammonium hydroxide and further twice with distilled water. The organic layer was dried and concentrated, and the solid obtained was washed with diisopropyl ether to yield 48 g of Compound II-1.

300 MHz $^1$H-NMR

δ 7.5-7.7 (m, 15H)

Compounds (II-2) to (II-16) were also synthesized using the corresponding sulfonium iodides respectively in accordance with the same method as described above.

Further, compounds represented by formula (III) were synthesized using the same method as the compounds of formula (II).

SYNTHESIS EXAMPLE 2

Synthesis of Resin as Component (B))

<(1) Synthesis of p-(1-(Cyclohexylethoxy)ethoxy)styrene/p-Hydroxystyrene (30/70) Copolymer (Resin A-25)> p-Hydroxystyrene (VP-8000, produced by Nippon Soda Co., Ltd.) in an amount of 70 g was dissolved in 320 g of propylene glycol monomethyl ether acetate (PGMEA) with heating, dehydrated by vacuum distillation, and then cooled to 25° C. To this solution, 0.35 g of pyridinium p-toluenesulfonate and 22.4 g of cyclohexane ethanol were added, and further 17.5 g of t-butyl vinyl ether was added at a slow speed. In the resulting mixture, reaction was run for 5 hours at 20° C. Thereafter, the reaction solution was admixed with 0.28 g of triethylamine and 320 ml of ethyl acetate, and washed with 150 ml each of distilled water for three times. Therefrom, the solvent was distilled away, and the residue was concentrated. The thus obtained oil was dissolved in 100 ml of acetone, and poured slowly into 2 liter of distilled water. As a result, a powdery matter separated out. This powdery matter was filtered off and dried to yield 54 g of the desired resin.

<(2) Synthesis of p-(1-Cyclohexylethoxy)ethoxy)styrene/p-Acetoxystyrene/p-Hydroxystyrene (30/10/60) Copolymer (Resin A-38)> p-Hydroxystyrene (VP-8000, produced by Nippon Soda Co., Ltd.) in an amount of 70 g was dissolved in 320 g of propylene glycol monomethyl ether acetate (PGMEA) with heating, dehydrated by vacuum distillation, and then cooled to 20° C. To this solution, 0.35 g of pyridinium p-toluenesulfonate and 22.4 g of cyclohexane ethanol were added, and further 17.5 g of t-butyl vinyl ether was added at a slow speed. In the resulting mixture, reaction was run for 5 hours at 20° C. Then, 5.53 g of pyridine was added to the reaction solution, and further thereto was slowly added 5.9 g of acetic anhydride. Thereafter, the reaction solution was admixed with 320 ml of ethyl acetate, and washed with 150 ml each of distilled water for three times. Therefrom, the solvent was distilled away, and the residue was concentrated. The thus obtained oil was dissolved in 100 ml of acetone, and poured slowly into 2 liter of distilled water. As a result, a powdery matter separated out. This powdery matter was filtered off and dried to yield 58 g of the desired resin.

(3) The Following Resins were Synthesized in the Same Manner as in Syntheses (1) and (2).

A-3: p-(1-Ethoxyethoxy)styrene/p-hydroxystyrene (35/65) copolymer (molecular weight: 15,000, dispersion degree (Mw/Mn): 1.1)

A-7: p-(1-iso-Butoxyethoxy)styrene/p-hydroxystyrene (30/70) copolymer (molecular weight: 6,000, dispersion degree (Mw/Mn): 1.2)

A-36: p-(1-Phenetyloxyethoxy)styrene/p-acetoxystyrene/p-hydroxys tyrene (30/10/60) copolymer (molecular weight: 11,000, dispersion degree (Mw/Mn): 1.2)

A-41: p-(1-(4-t-butylcyclohexylcarboxyethoxy)ethoxystyrene/p-acetoxystyrene/p-hydroxystyrene (30/10/60) copolymer (molecular weight: 12,000, dispersion degree (Mw/Mn): 1.1)

A-43: p-(1-Cyclohexylethoxy)ethoxy)styrene/p-t-butylstyrene/p-hydroxystyrene (30/8/62) copolymer (molecular weight: 18,000, dispersion degree (Mw/Mn): 2.3)

A-22: p-(1-Benzyloxyethoxy)styrene/p-hydroxystyrene (25/75) copolymer (molecular weight: 13,000, dispersion degree: 1.3)

A-35: p-(1-Benzyloxyethoxy)styrene/p-hydroxystyrene/p-acetoxysty rene (20/70/10) copolymer (molecular weight: 9,000, dispersion degree (Mw/Mn): 1.2)

Furthermore, the following resins as Component (B) was synthesized.

<(4) Synthesis of Resin A-48 as p-Hydroxystyrene/t-butyl acrylate (79/21) Copolymer>

In 150 g of dioxane, 84.1 g of p-vinylphenol and 22.4 g of t-butyl acrylate were dissolved, and thereto a stream of nitrogen was introduced for one hour.

Thereto, 6.91 g of dimethyl 2,2'-azobisisobutyrate was added, and the resulting mixture was heated up to 75° C. under a stream of nitrogen. Therein, polymerization was run for 12 hours. At the conclusion of the polymerization, the reaction solution was cooled to room temperature, and diluted with 150 g of acetone. This admixture was added dropwise to a large amount of hexane to yield a solid polymer. The remaining monomers were removed by repeating the dilution with acetone and the dropwise addition to hexane for three times.

The resulting polymer was dried at 60° C. under reduced pressure. Thus, the copolymer A-48 was obtained.

By NMR analysis, it was confirmed that the compositional ratio of p-vinylphenol to t-butyl acrylate was 79:21.

And Mw of the resin obtained was 12,000 and the dispersion degree (Mw/Mn) thereof was 2.6.

<(5) Synthesis of Resin A-16 as p-(1-Isobutoxyethoxy)styrene/p-hydroxystyrene/t-butyl acrylate (20/59/21) Copolymer>

The copolymer (A-48) in an amount of 20 g was dissolved in 80 g of propylene glycol monoethyl ether acetate (PGMEA), and heated to 60° C. Then, this reaction system was decompressed gradually to 20 mmHg, and the water and PGMEA in the system were removed by azeotropic distillation. Thereafter, the system was cooled to 20° C., and thereto 2.2 g of isobutyl vinyl ether and 3 mg of p-toluenesulfonic acid were added sequentially. After the addition was completed, the reaction was run for 2 hours, followed by neutralization of the acid with a small amount of triethylamine. Then, ethyl acetate was poured into the reaction solution, and therefrom the salt was removed by washing with ion-exchanged water. Further, the ethyl acetate and the water were distilled away from the reaction solution under reduced pressure. Thus, the desired polymer A-16 was obtained.

<(6) Synthesis of Resin A-51 as p-Hydroxystyrene/styrene/t-butyl acrylate (78/7/15) Copolymer>

Resin A-51 having molecular weight of 13,100 and a dispersion degree (Mw/Mn) of 2.7 was synthesized in the same manner as Resin A-48.

<(7) Synthesis of Resin A-49 as p-Hydroxystyrene/p-(t-butoxycarbonyloxy)styrene (60/40) Copolymer>

Poly(p-hydroxystyrene) having a weight average molecular weight of 11,000 (VP-8000, produced by Nippon Soda Co., Ltd.) was dissolved in 40 ml of pyridine, and thereto 1.28 g of di-t-butyl dicarbonate was added with stirring at room temperature. The admixture underwent reaction for 3 hours at room temperature, and then poured into a solution constituted of 1 liter of ion-exchanged water and 20 g of concentrated hydrochloric acid, thereby depositing a powdery matter. The powdery matter was filtered off, washed with water, and then dried to yield p-hydroxystyrene/p-(t-butyloxycarbonyloxy) styrene (60/40) copolymer.

EXAMPLES 1 TO 30 AND COMPARATIVE EXAMPLES 1 TO 3

According to each of the formulations shown in Tables 1 and 2, ingredients were dissolved in a given solvent in their respective amounts to prepare a solution having a total solids concentration of 15 weight %. This solution was filtered through a 0.1-μm polyethylene filter to prepare a resist solution. The performance evaluations were made on the thus prepared resist solutions in the following ways.

A: Evaluations by Exposure to KrF Excimer Laser

DUV42 (produced by Brewer Science Inc.) was coated on a silicon wafer treated with hexamethyldisilazane, and heated at 215° C. for 60 seconds to form an antireflective film having a thickness of 550 angstrom.

On the thus processed silicon wafer, each resist solution was coated uniformly by means of a spin coater, and dried by heating on a 120° C. hot plate for 90 seconds to form a 0.6 μm-thick resist film. The resist film was subjected to pattern exposure using a KrF excimer laser stepper (NA=0.63) and a mask pattern composed of lines and spaces. Immediately after the exposure, the resist film was baked for 90 seconds on a 110° C. hot plate. The thus baked resist film was developed with a 2.38% aqueous solution of tetramethylammonium hydroxide at 23° C. for 60 seconds, rinsed with purified water for 30 seconds, and then dried.

By use of the patterns thus formed on the silicon wafer, the following performance evaluations were made on each resist solution. The results obtained are shown in Table 3.

(Resolution)

The resolution is expressed in terms of the limiting resolution achieved under the exposure required for reproducing a 0.18 μm line-and-space (1/1) mask pattern.

(Exposure Margin)

The exposure margin is defined as a value (%) obtained by dividing an exposure range reproducing the line widths of 0.16 μm±10% by an optimum exposure and expressing the quotient as a percentage, wherein the exposure required for reproducing a 0.16 μm line-and-space (1/1) mask pattern is taken as the optimum exposure. The greater the value, the smaller change is caused in line width when a change in exposure occurs.

(Focus Depth)

The focus depth of 0.15 μm line-and-space is measured under the exposure required for reproducing the 0.15 μm line-and-space (1/1) mask pattern. The greater the measured value, the broader the focus depth.

TABLE 1

| Example | Acid generator (g) | Resin (g) | Other component (g) | Base (g) | Surfactant (0.02 g) | Solvent |
|---|---|---|---|---|---|---|
| 1 | A-24 (0.4) | A-25 (10) | — | (1) (0.05) | W-2 | PGMEA/PGME (8/2) |
| 2 | A-25 (0.3) | A-38 (10) | — | (1) (0.05) | W-2 | PGMEA/PGME (8/2) |
| 3 | A-26 (0.5) | A-36 (10) | — | (2) (0.02) | W-2 | PGMEA |
| 4 | A-27 (0.4) | A-43 (10) | — | (2) (0.02) | W-4 | PGMEA |
| 5 | A-30 (0.5) | A-35 (10) | — | (3) (0.05) | W-4 | EL/EEP |
| 6 | A-38 (0.2) | A-22 (10) | — | (3) (0.01) | W-4 | BL |

TABLE 1-continued

| Example | Acid generator (g) | Resin (g) | Other component (g) | Base (g) | Surfactant (0.02 g) | Solvent |
|---|---|---|---|---|---|---|
| 7 | A-39 (0.3) | A-38 (5) A-3 (4) | D-2 (1) | (1) (0.02) | W-4 | CH |
| 8 | A-92/A-28 (0.4) | A-25 (7) A-51 (3) | — | (4) (0.01) | W-2 | PGMEA/PGME (8/2) |
| 9 | A-1 (0.2) | A-38 (10) | B'-1 (0.1) | (2) (0.005) | W-1 | PGMEA |
| 10 | A-24 (0.3) PAG4-3 (0.1) PAG7-3 (0.5) | A-38 (10) | — | (4) (0.05) | W-4 | PGMEA/PGME (8/2) |
| 11 | A-26 (0.3) | A-3 (10) | — | (5) (0.02) | W-3 | PGMEA |
| 12 | A-1 (0.2) A-25 (0.2) | A-51 (5) A-3 (5) | — | (1) (0.02) | W-2 | PGMEA/PGME (8/2) |
| 13 | A-25 (0.3) PAG7-5 (0.1) | A-3 (2) A-49 (6.5) | D-2 (1.5) | (5) (0.01) | W-1 | PGMEA/PGME (8/2) |
| 14 | A-107 (0.5) | A-3 (8) A-48 (1) A-49 (1) | B'-3 (0.1) | (1) (0.01) (5) (0.01) | W-4 | PGMEA/PGME (8/2) |
| 15 | A-110 (0.3) PAG4-32 (0.2) | A-15 (10) | — | (4) (0.05) | W-2 | PGMEA/PGME (8/2) |
| 16 | A-97 (0.3) | A-1 (10) | — | (2) (0.02) | W-4 | EL/EEP |
| 17 | A-24 (0.2) PAG4-3 (0.2) PAG7-3 (0.3) | A-48 (5) A-49 (5) | — | (4) (0.02) | W-4 | PGMEA/PGME (8/2) |
| 18 | A-92 (0.6) | A-48 (10) | — | (5) (0.02) | W-2 | PGMEA |
| 19 | A-2 (0.4) PAG4-4 (0.1) | A-51 (10) | — | (1) (0.01) | W-3 | PGMEA/PGME (8/2) |
| 20 | A-3 (0.3) | A-49 (10) | — | (5) (0.02) | W-1 | PGMEA |
| 21 | A-24 (0.4) PAG4-36 (0.1) | p-PHS (8) | D-1 (2) B'-2 (0.2) | (1) (0.01) (5) (0.02) | W-2 | PGMEA/PGME (8/2) |
| 22 | A-26 (0.3) PAG3-22 (0.1) | p-PHS/St (9) | D-2 (1) | (1) (0.01) (2) (0.01) | W-4 | PGMEA |
| 23 | A-2 (0.5) | m-PHS (8.5) | D-3 (1.5) | (1) (0.02) | W-3 | EL/EEP |

TABLE 2

| Example | Acid generator (g) | Resin (g) | Other component (g) | Base (g) | Surfactant (0.02 g) | Solvent |
|---|---|---|---|---|---|---|
| 24 | A-19 (0.2) PAG4-38 (0.2) | A-48 (5) A-49 (5) | — | (4) (0.02) | W-4 | PGMEA/PGEM (8/2) |

TABLE 2-continued

| | Acid generator (g) | Resin (g) | Other component (g) | Base (g) | Surfactant (0.02 g) | Solvent |
|---|---|---|---|---|---|---|
| 25 | A-40 (0.3) PAG4-37 (0.1) | A-48 (10) | — | (5) (0.02) | W-2 | PGMEA/ |
| 26 | A-43 (0.4) | A-51 (10) | — | (1) (0.01) | W-3 | PGMEA/ PGME (8/2) |
| 27 | A-44 (0.3) PAG4-3 (0.1) | A-49 (10) | — | (5) (0.02) | W-1 | PGMEA |
| 28 | A-48 (0.3) PAG4-32 (0.2) | p-PHS (8) | D-1 (2) B'-2 (0.2) | (1) (0.01) (5) (0.02) | W-2 | PGMEA/ PGME (8/2) |
| 29 | A-51 (0.4) | p-PHS/St (9) | D-2 (1) | (1) (0.01) (2) (0.01) | W-4 | PGMEA |
| 30 | A-49 (0.4) PAG4-4 (0.1) | m-PHS (8.5) | D-3 (1.5) | (1) (0.02) | W-3 | EL/EEP |
| Comparative Example | | | | | | |
| 1 | PAG-A (0.4) | A-25 (10) | — | (1) (0.05) | W-2 | PGMEA/ PGME (8/2) |
| 2 | PAG-A (0.2) PAG4-3 (0.2) PAG7-3 (0.3) | A-48 (5) A-49 (5) | — | (4) (0.02) | W-4 | PGMEA/ PGME (8/2) |
| 3 | PAG-B (0.5) | m-PHS (8.5) | D-3 (1.5) | (1) (0.02) | W-3 | EL/EEP |

(Explanation of Ingredients in Tables 1 and 2)

Component (A)

PAG-A: Triphenylsulfonium perfluorobutanesulfonate

PAG-B: Bis(t-butylphenyl)iodonium perfluorobutane-sulfonate

Component (B) (amount mixed: value expressed on a solid basis)

p-PHS/St: Alkali-soluble p-Hydroxystyrene/styrene (85/15 by mole) copolymer (weight average molecular weight: 20,000, dispersion degree: 2.9)

B'-1 to B'-3 are the compounds having the following structural formulae, respectively:

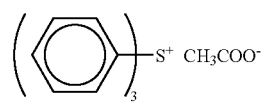
(B'-1)

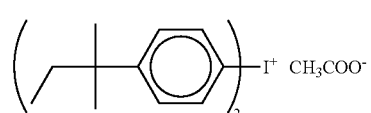
(B'-2)

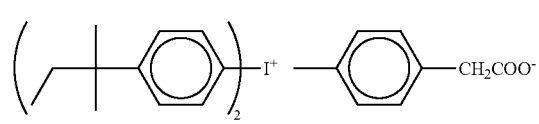
(B'-3)

D-1 to D-3 are the compounds having the following structural formulae, respectively:

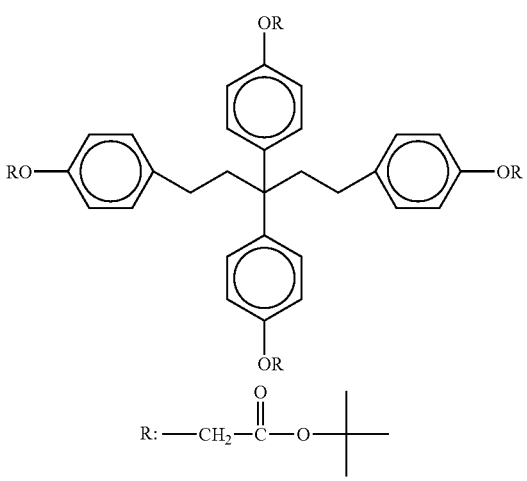
(D-1)

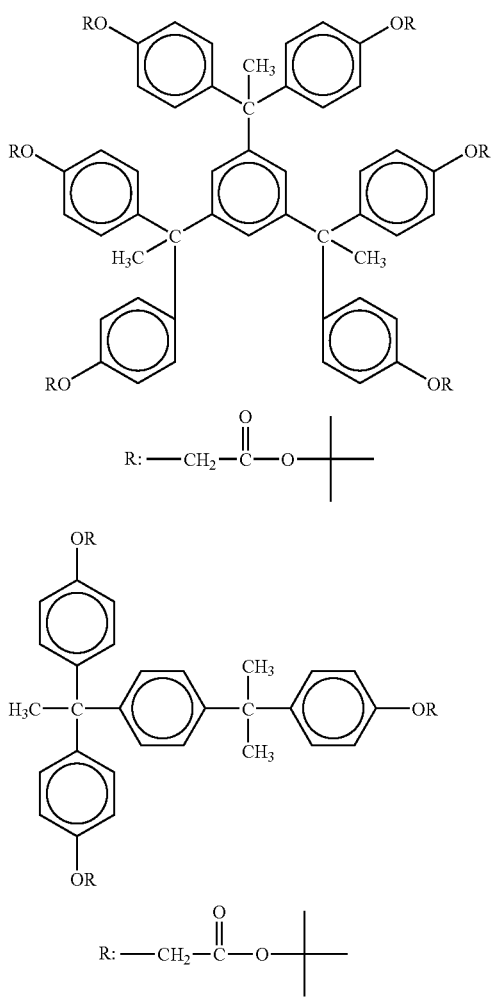

Component (E) (Basic compound)
(1): 1,5-diazabicyclo[4.3.0]-5-nonene
(2): 2,4,5-Triphenylimidazole
(3): Tri-n-butylamine
(4): N-Hydroxyethylpiperidine
(5): Tetrabutylammonium hydroxide Component (F) (Surfactant)
W-1: Megafac F176 (produced by Dai-Nippon Ink & Chemicals, Inc.) (surfactant containing fluorine atoms)
W-2: Megafac R08 (produced by Dai-Nippon Ink & Chemicals, Inc.) (surfactant containing both fluorine and silicon atoms)
W-3: Organosiloxane polymer KP-341 (produced by Shin-Etsu Chemical Industry Co., Ltd.)
W-4: Troysol S-366 (produced by troy Chemical Industried, Inc.) (surfactant containing fluorine atoms)

Solvent
PGMEA: Propylene glycol monomethyl ether acetate
PGME: Propylene glycol monomethyl ether (1-methoxy-2-propanol)
EL: Ethyl lactate
EEP: Ethyl ethoxypropionate
BL: γ-Butyrolactone
CH: Cyclohexanone

TABLE 3

| | Resolution (μm) | Exposure margin (%) | Focus depth (μm) |
|---|---|---|---|
| Example | | | |
| 1 | 0.125 | 12.0 | 1.4 |
| 2 | 0.125 | 11.5 | 1.3 |
| 3 | 0.125 | 13.0 | 1.3 |
| 4 | 0.125 | 11.4 | 1.2 |
| 5 | 0.125 | 12.0 | 1.5 |
| 6 | 0.125 | 12.1 | 1.4 |
| 7 | 0.125 | 12.0 | 1.3 |
| 8 | 0.125 | 11.0 | 1.3 |
| 9 | 0.125 | 12.3 | 1.5 |
| 10 | 0.125 | 11.9 | 1.2 |
| 11 | 0.13 | 12.0 | 1.0 |
| 12 | 0.13 | 11.4 | 1.1 |
| 13 | 0.13 | 12.6 | 1.1 |
| 14 | 0.13 | 12.4 | 1.2 |
| 15 | 0.13 | 11.5 | 1.2 |
| 16 | 0.13 | 12.0 | 1.1 |
| 17 | 0.125 | 10.6 | 1.2 |
| 18 | 0.125 | 10.8 | 1.0 |
| 19 | 0.125 | 9.7 | 1.1 |
| 20 | 0.125 | 9.2 | 1.0 |
| 21 | 0.125 | 10.7 | 1.1 |
| 22 | 0.125 | 9.0 | 1.2 |
| 23 | 0.125 | 9.8 | 1.2 |
| 24 | 0.13 | 9.5 | 1.1 |
| 25 | 0.13 | 10.1 | 1.2 |
| 26 | 0.13 | 9.4 | 1.1 |
| 27 | 0.13 | 10.5 | 1.2 |
| 28 | 0.13 | 9.0 | 1.0 |
| 29 | 0.13 | 9.7 | 1.2 |
| 30 | 0.13 | 10.2 | 1.1 |
| Comparative Example | | | |
| 1 | 0.14 | 4.1 | 0.5 |
| 2 | 0.14 | 5.5 | 0.7 |
| 3 | 0.14 | 3.4 | 0.4 |

As can be seen from the data shown in Table 3, each of the resist films formed with the present positive resist compositions in Examples 1 to 30 respectively achieved high resolution, and had a wide exposure margin and a broad focus depth in the pattern formation by exposure to KrF excimer laser as a far ultraviolet ray.

In the cases of the resist films formed with the positive resist compositions not containing the present Component (A) as in Comparative Examples 1 to 3, on the other hand, both exposure margin and focus dept were narrow.

Further, in the experiments for performance evaluations, no development residues were detected on the present resist films formed in Examples 1 to 30.

On the other hand, the resist films formed in Comparative Examples 1 to 3 were unsuccessful in resolving patterns finer than 0.13 μm by occurrence of development residue.

B: Evaluation by Irradiation with Electron Beams

Resist solutions were prepared according to the same formulations as in several (shown in Table 4) of Examples set forth in Tables 1 and 2, except that the total solid concentration was changed to 17%.

Additionally, 1 g of benzoyloxyvinyl ether (vinyloxyethyl benzoate) was further added to each of the compositions in Examples 8, 13 and 23 and Comparative Example 3.

Each of the resist solutions was coated uniformly on a silicon substrate treated with hexamethyldisilazane by means of a spin coater, and dried by heating on a 120° C. hot plate for 60 seconds to form a 0.8 μm-thick resist film. The resist film underwent irradiation with an electron-beam drawing apparatus (acceleration voltage: 50 KeV, beam diameter: 0.20 µm). Immediately after the irradiation, the resist film was baked for 90 seconds on a 110° C. hot plate. The thus baked resist film was developed with a 2.38% aqueous solution of tetramethylammonium hydroxide at 23° C. for 60 seconds, rinsed with purified water for 30 seconds, and then dried.

By use of the patterns thus formed on the silicon substrate, the following performance evaluations were made on each resist. The results obtained are shown in Table 4.

(Image Evaluation)

The 0.2 µm contact hole patterns thus formed were observed under a scanning electron microscope and examined for their respective profiles.

(Sensitivity Evaluation)

The sensitivity was evaluated by the amount of irradiation (µC/cm$^2$) required for reproducing 0.2 µm contact hole patterns.

(Resolution Evaluation)

The resolution was expressed in terms of the limiting resolution achieved under the irradiation reproducing 0.2 µm contact hole patterns.

TABLE 4

| Example (irradiation with electron beam) | Sensitivity (µC/cm$^2$) | Resolution (µm) | Profile |
|---|---|---|---|
| 1 | 7 | 0.8 | rectangular |
| 8 | 5 | 0.8 | rectangular |
| 13 | 9 | 0.8 | rectangular |
| 17 | 7 | 0.8 | rectangular |
| 21 | 7 | 0.8 | rectangular |
| 22 | 5 | 0.8 | rectangular |
| 23 | 9 | 0.8 | rectangular |
| Comparative Example 1 | 8 | 0.9 | somewhat inverted taper |
| Comparative Example 2 | 7 | 0.9 | somewhat inverted taper |
| Comparative Example 3 | 7 | 0.9 | somewhat inverted taper |

As can be seen from the results shown in Table 4, the present compositions achieved highly sensitive and highly resolved pattern formation by electron-beam irradiation, and what is more, ensured a rectangular profile in the resist patterns without providing an inverted taper profile caused by a scattering phenomenon characteristic of electron-beam irradiation.

<Syntheses of Resins>

[Synthesis of Resin (P1), (a1)/(b1)=50/50]

A solution containing 5.0 g of 2-methyl-2-adamantane methacrylate, 4.23 g of mevalonic lactone methacrylate and 0.534 g of a polymerization initiator, 2,2'-azobis(2,4-dimethylvaleronitrile) (V-65, produced by Wako Pure Chemical Industries, Ltd.) in 30.0 g of N,N-dimethylacetamide was added dropwise over a period of 4 hours to 7.0 g of N,N-dimethylacetamide heated at 60° C. under a stream of nitrogen. In this admixture, the reaction was further continued for 2 hours at 60° C. Then, 0.267 g of V-65 was further added, and the reaction was run for additional 2 hours. The reaction mixture was poured into 1,000 ml of ion-exchanged water, and the thus deposited powdery matter was filtered off. The powdery matter was dissolved in THF, and poured into 1,500 ml of hexane. By drying the thus deposited powdery matter, the intended Resin (P1) was obtained.

The resin obtained had a weight average molecular weight of 5,500 and a dispersion degree (Mw/Mn) of 1.9. Additionally, these values of weight average molecular weight and dispersion degree were measured by DSC method and expressed on a polystyrene basis.

[Syntheses of Resins (P2) to (P20)]

Resins (P2) to (P20) shown in Table 5 were each synthesized in similar manner to the above. The molecular weights and dispersion degrees of these resins are shown in Table 5.

TABLE 5

| Resin | Monomers used (ratio) | Molecular weight (Dispersion degree) |
|---|---|---|
| (P1) | a1/b1 (50/50) | 5,500 (1.9) |
| (P2) | a1/b1/methacrylic acid (45/45/10) | 9,000 (1.9) |
| (P3) | a4/b47 (55/45) | 16,700 (1.8) |
| (P4) | a4/b5 (60/40) | 4,600 (2.2) |
| (P5) | a5/b47/methacrylic acid (45/45/10) | 8,700 (2.1) |
| (P6) | a5/b1 (50/50) | 5,600 (1.7) |
| (P7) | a18/b1 (50/50) | 23,000 (2.3) |
| (P8) | a16/b1 (50/50) | 12,300 (2.2) |
| (P9) | a16/b1/methacrylic acid (45/45/10) | 14,100 (1.9) |
| (P10) | b54/maleic anhydride (50/50) | 3,600 (2.0) |
| (P11) | b54/b55/b56/maleic anhydride (15/25/10/50) | 5,400 (1.9) |
| (P12) | a1/b1/diethylene glycol monomethyl ether methacrylate (47.5/47.5/5) | 10,100 (2.4) |
| (P13) | b53/maleic anhydride/t-butyl acrylate (40/40/20) | 11,000 (1.8) |
| (P14) | b53/maleic anhydride/t-butyl acrylate/a20 (36/36/18/10) | 13,000 (1.9) |
| (P15) | b1/b62/a5 (40/30/30) | 11,000 (1.8) |
| (P16) | b53/maleic anhydride/b43/b42 (30/30/30/10) | 11,000 (1.9) |
| (P17) | b54/maleic anhydride/b48/b44 (30/30/10/20) | 13,000 (2.1) |
| (P18) | b53/maleic anhydride/b45 (35/35/30) | 8,500 (1.7) |
| (P19) | b64/b63/a5 (40/30/30) | 11,000 (1.9) |
| (P20) | b64/b63/b65 (40/30/30) | 13,000 (2.2) |

<Resist Preparation>

EXAMPLES 31 TO 71 AND COMPARATIVE EXAMPLES 4 TO 6

Resist solutions having a total solid concentration of 15% were each prepared by dissolving ingredients shown in Tables 6 and 7, and filtered through a 0.1-µm Teflon filter. The thus prepared photosensitive compositions were each evaluated by the following methods. The results obtained are shown in Table 8.

TABLE 6

| Example | Acid generator (g) | Resin (g) | Other component (g) | Base (g) | Surfactant (0.02 g) | Solvent |
|---|---|---|---|---|---|---|
| 31 | A-24 (0.4) | P1 (20) | — | (1) (0.05) | W-2 | PGMEA/PGME (8/2) |

TABLE 6-continued

| Example | Acid generator (g) | Resin (g) | Other component (g) | Base (g) | Surfactant (0.02 g) | Solvent |
|---|---|---|---|---|---|---|
| 32 | A-25 (0.3) | P2 (20) | — | (1) (0.05) | W-2 | PGMEA/PGME (8/2) |
| 33 | A-26 (0.5) | P3 (20) | — | (2) (0.02) | W-2 | PGMEA |
| 34 | A-27 (0.4) | P4 (20) | — | (2) (0.02) | W-4 | PGMEA |
| 35 | A-30 (0.5) | P5 (20) | — | (3) (0.05) | W-4 | EL/EEP |
| 36 | A-38 (0.2) | P6 (20) | — | (3) (0.01) | W-4 | BL |
| 37 | A-39 (0.3) | P7 (20) | — | (1) (0.02) | W-4 | CH |
| 38 | A-92/A-28 (0.4) | P8 (20) | — | (4) (0.01) | W-2 | PGMEA/PGME (8/2) |
| 39 | A-1 (0.2) | P9 (20) | B'-1 (0.1) | (2) (0.005) | W-1 | PGMEA |
| 40 | A-24 (0.3) PAG4-3 (0.05) PAG7-3 (0.5) | P10 (18) | t-Bu cholate (2) | (4) (0.05) | W-4 | PGMEA/PGME (8/2) |
| 41 | A-26 (0.3) | P11 (20) | — | (5) (0.02) | W-3 | PGMEA |
| 42 | A-1 (0.2) A-25 (0.2) | P12 (20) | — | (1) (0.02) | W-2 | PGMEA/PGME (8/2) |
| 43 | A-25 (0.3) PAG4-36 (0.1) | P13 (20) | — | (5) (0.01) | W-1 | PGMEA/PGME (8/2) |
| 44 | A-107 (0.5) | P14 (20) | B'-2 (0.1) | (1) (0.01) (5) (0.01) | W-4 | PGMEA/PGME (8/2) |
| 45 | A-110 (0.3) PAG4-32 (0.2) | P1 (20) | — | (4) (0.05) | W-2 | PGMEA/PGME (8/2) |
| 46 | A-97 (0.3) | P3 (20) | — | (2) (0.02) | W-4 | EL/EEP |
| 47 | A-24 (0.2) PAG4-3 (0.2) PAG7-3 (0.3) | P10 (20) | — | (4) (0.02) | W-4 | PGMEA/PGME (8/2) |
| 48 | A-92 (0.6) | P11 (20) | — | (5) (0.02) | W-2 | PGMEA |
| 49 | A-2 (0.4) PAG4-4 (0.1) | P13 (20) | — | (1) (0.01) | W-3 | PGMEA/PGME (8/2) |
| 50 | A-3 (0.3) | P14 (20) | — | (5) (0.02) | W-1 | PGMEA |
| 51 | A-55 (1) PAG4-5 (0.2) | P15 (20) | — | (1) (0.05) | W-2 | PGMEA/PGME (8/2) |
| 52 | A-33 (0.6) PAG4-4 (0.1) | P15 (20) | — | (1) (0.05) | W-2 | PGMEA/PGME (8/2) |
| 53 | A-54 (1) A-24 (0.2) | P14 (20) | — | (2) (0.02) | W-2 | PGMEA |
| 54 | A-53 (1) PAG4-38 (0.1) | P14 (20) | — | (2) (0.02) | W-4 | PGMEA |

TABLE 7

| Example | Acid generator (g) | Resin (g) | Other component (g) | Base (g) | Surfactant (0.02 g) | Solvent |
|---|---|---|---|---|---|---|
| 55 | A-56 (0.2) Z31 (0.4) | P16 (20) | — | (1) (0.05) | W-2 | PGMEA/PGME (8/2) |

TABLE 7-continued

| | Acid generator (g) | Resin (g) | Other component (g) | Base (g) | Surfactant (0.02 g) | Solvent |
|---|---|---|---|---|---|---|
| 56 | A-58 (0.3) Z21 (0.5) | P17 (20) | — | (1) (0.05) | W-2 | PGMEA/ PGME (8/2) |
| 57 | A-59 (0.4) Z22 (0.4) | P18 (20) | — | (2) (0.02) | W-2 | PGMEA |
| 58 | A-60 (0.8) | P19 (20) | — | (2) (0.02) | W-4 | PGMEA |
| 59 | A-62 (0.8) Z13 (0.3) | P20 (20) | — | (3) (0.05) | W-4 | EL/EEP |
| 60 | A-66 (0.5) Z30 (0.4) | P16 (15) P19 (5) | — | (3) (0.01) | W-4 | BL |
| 61 | A-71 (0.5) Z21 (0.8) | P17 (20) | — | (1) (0.02) | W-4 | CH |
| 62 | A-72 (0.2) Z2 (0.2) Z1 (0.1) | P18 (20) | — | (4) (0.01) | W-2 | PGMEA/ PGME (8/2) |
| 63 | A-76 (0.4) Z6 (0.2) | P17 (5) P19 (15) | — | (2) (0.005) | W-1 | PGMEA |
| 64 | A-66 (0.4) Z31 (0.4) Z21 (0.2) | P16 (8) P20 (8) P6 (2) | — | (4) (0.01) | W-4 | PGMEA/ PGME (8/2) |
| 65 | A-80 (0.2) Z31 (0.2) | P19 (20) | — | (2) (0.02) | W-4 | PGMEA |
| 66 | A-81 (0.1) Z21 (0.5) | P20 (20) | — | (3) (0.05) | W-4 | EL/EEP |
| 67 | A-84 (0.15) z31 (0.2) Z21 (0.3) | P16 (15) P19 (5) | — | (3) (0.01) | W-4 | BL |
| 68 | A-86 (0.4) Z13 (0.1) | P17 (20) | | (1) (0.02) | W-4 | CH |
| 69 | A-87 (0.5) Z14 (0.05) | P18 (20) | | (4) (0.01) | W-2 | PGMEA/ PGME (8/2) |
| 70 | A-90 (0.7) Z3 (0.1) | P17 (5) P19 (15) | — | (2) (0.005) | W-1 | PGMEA |
| 71 | A-80 (0.1) A-91 (0.6) | P16 (8) P20 (8) P6 (2) | — | (4) (0.01) | W-4 | PGMEA/ PGME (8/2) |
| Comparative Example | | | | | | |
| 4 | PAG-A (0.4) | P1 (20) | — | (1) (0.05) | W-2 | PGMEA/ PGME (8/2) |
| 5 | PAG-A (0.3) PAG4-3 (0.05) PAG7-3 (0.5) | P10 (18) | t-Bu cholate (2) | (4) (0.05) | W-4 | PGMEA/ PGME (8/2) |
| 6 | PAG-B (0.3) | P14 (20) | — | (5) (0.02) | W-1 | PGMEA |

(Explanation of Ingredients in Tables 6 and 7)
(1): 1,5-diazabicyclo[4.3.0]-5-nonene
(2): 2,4,5-Triphenylimidazole
(3): Tri-n-butylamine
(4): N-Hydroxyethylpiperidine
(5): Tetrabutylammonium hydroxide
W-1: Megafac F176 (produced by Dai-Nippon Ink & Chemicals, Inc.) (surfactant containing fluorine atoms)
W-2: Megafac R08 (produced by Dai-Nippon Ink & Chemicals, Inc.) (surfactant containing both fluorine and silicon atoms)
W-3: Organosiloxane polymer KP-341 (produced by Shin-Etsu Chemical Industry Co., Ltd.)
W-4: Troysol S-366 (produced by troy Chemical Industried, Inc.) (surfactant containing fluorine atoms)
PGMEA: Propylene glycol monomethyl ether acetate
PGME: Propylene glycol monomethyl ether
EL: Ethyl lactate
EEP: Ethyl ethoxypropionate
BL: γ-Butyrolactone
CH: Cyclohexanone
PAG-A: Triphenylsulfonium perfluorobutanesulfonate
PAG-B: Bis(t-butylphenyl)iodonium perfluorobutane-sulfonate

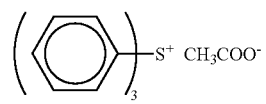

(B'-1)

-continued

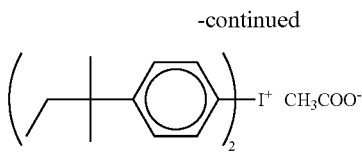
(B'-2)

<Image Evaluations>

Sensitivity, Resolution, Exposure Margin and Scum Evaluations:

DUV-42 (produced by Brewer Science Inc.) was coated in a thickness of 600 angstrom on a silicon substrate treated with hexamethyldisilazane, dried at 100° C. for 90 seconds, and further heated at 190° C. for 240 seconds to form an antireflective film.

On the thus processed silicon substrate, each photosensitive resin composition was coated by means of a spin coater, and dried by heating at 120° C. for 90 seconds to form a 0.50 μm-thick resist film. The resist film was subjected to pattern exposure using a ArF excimer laser stepper (NA=0.6, made by ISI Co., Ltd.) and a mask pattern. Immediately after the exposure, the resist film was baked for 90 seconds on a 120° C. hot plate. The thus baked resist film was developed with a 2.38% aqueous solution of tetramethylammonium hydroxide at 23° C. for 60 seconds, rinsed with purified water for 30 seconds, and then dried, thereby forming resist line patterns.

[Sensitivity]: The sensitivity is expressed in terms of the amount of exposure required for reproducing a 0.16 μm mask pattern.

[Resolution]: The resolution is expressed in terms of the limiting resolution achieved under the amount of exposure required for reproducing a 0.16 μm mask pattern.

[Exposure Margin]: The exposure margin is defined as a value (%) obtained by dividing an exposure range reproducing the line widths of 0.16 μm±10% by an optimum exposure and expressing the quotient as a percentage, wherein the exposure required for reproducing a 0.16 μm line-and-space (1/1) mask pattern is taken as the optimum exposure. The greater the value, the smaller change is caused in line width when a change in exposure occurs.

[Scum]: The following are evaluation criteria.
 ○; No scum was observed.
 Δ; Scum was observed on patterns having line widths in the vicinity of the limiting resolution.
 X; Scum was observed on patterns having line widths wider than the limiting resolution.

TABLE 8

| Example | Sensitivity (mJ/cm²) | Resolution (μm) | Exposure margin (%) | Scum |
|---|---|---|---|---|
| 31 | 7 | 0.11 | 10.0 | ○ |
| 32 | 6 | 0.115 | 12.0 | ○ |
| 33 | 8 | 0.12 | 11.5 | ○ |
| 34 | 10 | 0.115 | 10.4 | ○ |
| 35 | 12 | 0.12 | 12.0 | ○ |
| 36 | 8 | 0.12 | 11.0 | ○ |
| 37 | 9 | 0.115 | 12.5 | ○ |
| 38 | 10 | 0.12 | 10.4 | ○ |
| 39 | 7 | 0.115 | 11.0 | ○ |
| 40 | 12 | 0.12 | 10.3 | ○ |
| 41 | 12 | 0.12 | 10.0 | ○ |
| 42 | 10 | 0.115 | 10.5 | ○ |
| 43 | 11 | 0.115 | 12.0 | ○ |

TABLE 8-continued

| Example | Sensitivity (mJ/cm²) | Resolution (μm) | Exposure margin (%) | Scum |
|---|---|---|---|---|
| 44 | 8 | 0.115 | 11.4 | ○ |
| 45 | 9 | 0.12 | 10.5 | ○ |
| 46 | 10 | 0.12 | 10.0 | ○ |
| 47 | 7 | 0.115 | 12.2 | ○ |
| 48 | 12 | 0.12 | 11.0 | ○ |
| 49 | 11 | 0.115 | 10.9 | ○ |
| 50 | 8 | 0.12 | 10.0 | ○ |
| 51 | 10 | 0.11 | 10.8 | ○ |
| 52 | 5 | 0.11 | 12.0 | ○ |
| 53 | 12 | 0.11 | 13.0 | ○ |
| 54 | 9 | 0.11 | 12.5 | ○ |
| 55 | 9 | 0.11 | 12.3 | ○ |
| 56 | 10 | 0.11 | 13.0 | ○ |
| 57 | 12 | 0.11 | 12.2 | ○ |
| 58 | 8 | 0.11 | 13.1 | ○ |
| 59 | 10 | 0.11 | 12.8 | ○ |
| 60 | 7 | 0.11 | 13.5 | ○ |
| 61 | 9 | 0.11 | 11.9 | ○ |
| 62 | 11 | 0.11 | 12.0 | ○ |
| 63 | 12 | 0.11 | 13.3 | ○ |
| 64 | 7 | 0.11 | 14.0 | ○ |
| 65 | 12 | 0.11 | 12.5 | ○ |
| 66 | 11 | 0.11 | 13.1 | ○ |
| 67 | 9 | 0.11 | 14.0 | ○ |
| 68 | 10 | 0.11 | 13.3 | ○ |
| 69 | 12 | 0.11 | 14.0 | ○ |
| 70 | 12 | 0.11 | 12.9 | ○ |
| 71 | 10 | 0.11 | 13.0 | ○ |
| Compar. Ex. 4 | 12 | 0.12 | 8.2 | Δ |
| Compar. Ex. 5 | 14 | 0.125 | 4.9 | Δ |
| Compar. Ex. 6 | 14 | 0.13 | 7.0 | X |

As can be seen from the results shown in Table 8, each of the resist films formed with the compositions prepared in Examples 31 to 71 respectively had excellent sensitivity, resolution and exposure margin, and developed no scum.

On the other hand, each of the resist films formed with the compositions prepared in Comparative Examples 4 to 6 respectively were inferior in sensitivity, resolution, exposure margin or scum development to those with the compositions prepared in Examples.

In the lithography utilizing an exposure light source of short wavelengths enabling superfine processing and positive chemical amplification resist, the positive photosensitive compositions according to the present invention can achieve elevation of resolution, reduction of development residues, and improvements in processing latitudes, such as exposure margin and focus depth.

Further, the present photosensitive compositions can deliver excellent performances even in the case of using electron beams as energy beams for irradiation.

What is claimed is:

1. A positive photosensitive composition comprising:
 (A) a compound capable of generating a sulfonic acid represented by the following formula upon irradiation with one of an actinic ray and radiation; and
 (B) a resin which contains at least one of a monocyclic alicyclic structure and a polycyclic alicyclic structure and which is capable of decomposing under the action of an acid to increase the solubility in an alkali developer:

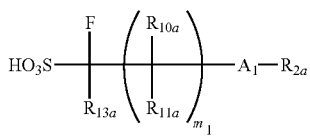

wherein $m_1$ is an integer of 0 to 3, $A_l$ represents a single bond, —CONR— or —COO, wherein R represents a hydrogen atom, or an alkyl group having 1 to 10 carbon atoms, which may be substituted with a halogen atom, a hydroxyl group or an alkoxy group, $R_{10a}$, $R_{11a}$ and $R_{13a}$ each represents a hydrogen atom, an alkyl group, a haloalkyl group, a halogen atom or a hydroxyl group, and $R_{2a}$ represents an alkyl group or a hydroxyl group.

2. The positive photosensitive composition as claimed in claim 1, wherein $m_1$ is 0 or 1.

3. The positive photosensitive composition as claimed in claim 1, wherein the resin (B) contains a lactone structure.

4. A pattern forming method comprising:
  forming a resist film with the positive photosensitive composition as claimed in claim 1;
  exposing the resist film; and
  developing the resist film.

* * * * *